(12) United States Patent
Hennequin et al.

(10) Patent No.: US 7,659,279 B2
(45) Date of Patent: Feb. 9, 2010

(54) QUINAZOLINE DERIVATIVES AND THEIR USE IN THE TREATMENT OF CANCER

(75) Inventors: Laurent Francois Andre Hennequin, Reims (FR); Alleyn Plowright, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 603 days.

(21) Appl. No.: 10/555,085

(22) PCT Filed: Apr. 27, 2004

(86) PCT No.: PCT/GB2004/001799

§ 371 (c)(1),
(2), (4) Date: Oct. 31, 2005

(87) PCT Pub. No.: WO2004/096226

PCT Pub. Date: Nov. 11, 2004

(65) Prior Publication Data

US 2006/0211714 A1 Sep. 21, 2006

(30) Foreign Application Priority Data

Apr. 30, 2003 (GB) ................................ 0309850.6

(51) Int. Cl.
*A61K 31/517* (2006.01)
*C07D 239/88* (2006.01)

(52) U.S. Cl. .................................. 514/266.2; 544/293
(58) Field of Classification Search .............. 514/266.2; 544/293
See application file for complete search history.

(56) References Cited

U.S. PATENT DOCUMENTS

| | | | |
|---|---|---|---|
| 4,322,420 A | 3/1982 | Kobayashi et al. | 514/266.4 |
| 4,335,127 A | 6/1982 | Vandenberk et al. | 514/266.22 |
| 4,640,920 A | 2/1987 | Boyle et al. | 514/248 |
| 4,921,863 A | 5/1990 | Sugimoto et al. | 514/319 |
| 5,405,843 A | 4/1995 | Fukazawa et al. | 514/183 |
| 5,457,105 A | 10/1995 | Barker | 514/234.5 |
| 5,616,582 A | 4/1997 | Barker | 514/234.5 |
| 5,721,237 A | 2/1998 | Myers et al. | 514/266.1 |
| 5,747,498 A | 5/1998 | Schnur et al. | 514/266.4 |
| 5,770,599 A | 6/1998 | Gibson | 514/228.2 |
| 5,929,080 A | 7/1999 | Frost | 514/266.4 |
| 5,962,458 A | 10/1999 | Lohmann et al. | 514/266.21 |
| 6,004,967 A | 12/1999 | McMahon et al. | 514/266.4 |
| 6,046,206 A | 4/2000 | Pamukcu et al. | 514/266.21 |
| 6,117,433 A | 9/2000 | Edens et al. | 424/400 |
| 6,297,258 B1 | 10/2001 | Wissner et al. | 514/313 |
| 6,313,130 B1 | 11/2001 | Uckun et al. | 514/266.24 |
| 6,326,373 B1 | 12/2001 | Uckun et al. | 514/266.1 |
| 6,384,223 B1 | 5/2002 | Gletsos | 544/293 |
| 6,562,319 B2 | 5/2003 | Mishani et al. | 424/1.81 |
| 6,617,329 B2 | 9/2003 | Himmelsbach et al. | 514/252.14 |
| 6,972,288 B1 | 12/2005 | Himmelsbach et al. | 514/234.8 |

(Continued)

FOREIGN PATENT DOCUMENTS

| | | |
|---|---|---|
| DE | 19908567 | 8/2000 |
| DE | 10040527 | 2/2002 |

(Continued)

OTHER PUBLICATIONS

Voskoglou-Nomikos et. al., "Clinical Predictive Value of the in-Vitro Cell Line, . . . " Clinical Cancer Research, Sep. 15, 2003, vol. 9, pp. 4227-4239.*
Barker et al. "Studies leading to the identification of ZD1839 (Iressa™): an orally active, selective eipdermal growth factor receptor tyrosine kinase inhibitor targeted to the treatment of cancer" Bioorganic and Medicinal Chemistry Letters 11(14):1911-1914 (2001).
Bridges et al. "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor" J. Med. Chem. 39(1):267-276 (1996).
Denny et al. "Structure-activity relationships for 4-anilinoquinazolines as potent inhibitors at the ATP binding site for the epidermal growth factor receptor in vitro" Clinical and Experimental Pharmacology and Physiology 23:424-427 (1996).
Hennequin et al. "Novel 4-Anilinoquinazolines with C-7 Basic Side Chains: Design and Structure Activity Relationship of a Series of Potent, Orally Active, VEGF Receptor Tyrosine Kinase Inhibitors" J. Med. Chem. 45 (6):1300-1312 (2002).
Rewcastle et al. "Tyrosine kinase inhibitors. 5. Synthesis and structure-activity relationships for 4-[(phenylmethyl)amino]- and 4-(phenylamino)quinazolines as potent adenoisine 5'-triphosphate binding site inhibitors of the tyrosine kinase domain of the epidermal growth factor receptor" J. Med. Chem. 38:3482-3487 (1995).
Stamos et al. "Structure of the Epidermal Growth Factor Receptor Kinase Domain Alone and in Complex with a 4-Anilinoquinazoline Inhibitor" J. Biol. Chem. 277(48):46265-46272 (2002).

(Continued)

Primary Examiner—James O Wilson
Assistant Examiner—Tamthom N Truong
(74) Attorney, Agent, or Firm—Morgan, Lewis & Bockius LLP

(57) ABSTRACT

The invention concerns quinazoline derivatives of the formula: (I); wherein $X^1$, $Q^1$, Z, $R^1$, $R^2$, Y, a and m are as defined in the description, which are erbB tyrosine kinase inhibitors, particularly EGFR tyrosine kinase inhibitors. Also claimed are processes for their preparation; pharmaceutical compositions containing them; and their use as therapeutic agents in the treatment of erbB tyrosine kinase mediated diseases such as cancer.

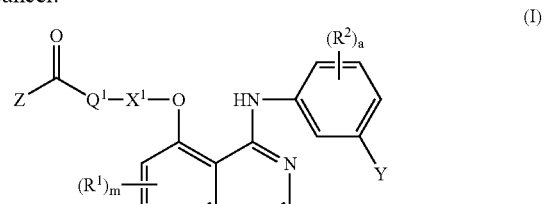

(I)

16 Claims, No Drawings

U.S. PATENT DOCUMENTS

| | | |
|---|---|---|
| 7,148,230 B2 | 12/2006 | Bradbury et al. |
| 2002/0082270 A1 | 6/2002 | Himmelsbach et al. ... 514/266.2 |
| 2002/0128553 A1 | 9/2002 | Mishani et al. ............. 600/431 |
| 2002/0177601 A1 | 11/2002 | Himmelsbach et al. ... 514/266.2 |
| 2004/0176361 A1 | 9/2004 | Fujio et al. ............... 514/224.2 |
| 2005/0043336 A1 | 2/2005 | Hennequin et al. ....... 514/266.4 |
| 2005/0054662 A1 | 3/2005 | Hennequin et al. ..... 514/266.22 |
| 2005/0215574 A1 | 9/2005 | Bradbury et al. |
| 2006/0287295 A1 | 12/2006 | Barlaam et al. |
| 2007/0015743 A1* | 1/2007 | Bradbury et al. ........ 514/210.21 |
| 2007/0032508 A1* | 2/2007 | Bradbury et al. ........ 514/255.05 |
| 2007/0032513 A1 | 2/2007 | Hennequin et al. |
| 2007/0037837 A1 | 2/2007 | Hennequin et al. |
| 2007/0043009 A1 | 2/2007 | Hennequin et al. |
| 2007/0043010 A1 | 2/2007 | Bradbury et al. |
| 2007/0082921 A1 | 4/2007 | Hennequin et al. |
| 2007/0088044 A1 | 4/2007 | Hennequin et al. |
| 2007/0099943 A1 | 5/2007 | Bradbury et al. |
| 2007/0149546 A1 | 6/2007 | Bradbury et al. |
| 2007/0232607 A1 | 10/2007 | Bradbury et al. |
| 2007/0244136 A1 | 10/2007 | Hennequin et al. |
| 2007/0293490 A1 | 12/2007 | Delouvrie et al. |

FOREIGN PATENT DOCUMENTS

| | | |
|---|---|---|
| EP | 0 288 563 | 5/1994 |
| EP | 0 607 439 | 7/1994 |
| EP | 0 566 226 | 11/1995 |
| EP | 0 602 851 | 10/1996 |
| EP | 0 520 722 | 12/1996 |
| EP | 0 787 722 | 8/1997 |
| EP | 0 837 063 | 4/1998 |
| EP | 0 326 330 | 7/2002 |
| EP | 1 230 919 | 8/2002 |
| EP | 1 369 418 | 12/2003 |
| GB | 2295387 | 5/1996 |
| JP | 08-003144 | 1/1996 |
| JP | 11-189586 | 7/1999 |
| WO | WO 88/02365 | 4/1988 |
| WO | WO 92/20642 | 11/1992 |
| WO | WO 93/08170 | 4/1993 |
| WO | WO 93/17682 | 9/1993 |
| WO | WO 95/15758 | 6/1995 |
| WO | 96/09294 A | 3/1996 |
| WO | WO 96/09294 | 3/1996 |
| WO | 96/15118 A | 5/1996 |
| WO | WO 96/15118 | 5/1996 |
| WO | WO 96/16960 | 6/1996 |
| WO | WO 96/30347 | 10/1996 |
| WO | WO 96/33977 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/11692 | 4/1997 |
| WO | WO 97/22596 | 6/1997 |
| WO | WO 97/30034 | 8/1997 |
| WO | WO 97/30035 | 8/1997 |
| WO | WO 97/30044 | 8/1997 |
| WO | WO 97/38983 | 10/1997 |
| WO | WO 98/02434 | 1/1998 |
| WO | WO 98/13354 | 4/1998 |
| WO | WO 98/38984 | 9/1998 |
| WO | WO 98/50038 | 11/1998 |
| WO | WO 98/50370 | 11/1998 |
| WO | WO 99/06378 | 2/1999 |
| WO | WO 99/09016 | 2/1999 |
| WO | WO 99/24037 | 5/1999 |
| WO | WO 99/35132 | 7/1999 |
| WO | WO 99/61428 | 12/1999 |
| WO | WO 00/00202 | 1/2000 |
| WO | WO 00/06555 | 2/2000 |
| WO | WO 00/09481 | 2/2000 |
| WO | WO 00/10981 | 3/2000 |
| WO | WO 00/18740 | 4/2000 |
| WO | WO 00/20402 | 4/2000 |
| WO | WO 00/24718 | 5/2000 |
| WO | WO 00/44728 | 8/2000 |
| WO | WO 00/47212 | 8/2000 |
| WO | WO 00/51587 | 9/2000 |
| WO | WO 00/51991 | 9/2000 |
| WO | WO 00/55141 | 9/2000 |
| WO | WO 00/73260 | 12/2000 |
| WO | WO 01/07432 | 2/2001 |
| WO | WO 01/12227 | 2/2001 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/32632 | 5/2001 |
| WO | WO 01/45641 | 6/2001 |
| WO | WO 01/77085 | 10/2001 |
| WO | 01/94341 A | 12/2001 |
| WO | WO 01/94341 | 12/2001 |
| WO | WO 01/98277 | 12/2001 |
| WO | WO 02/16352 | 2/2002 |
| WO | WO 02/18370 | 3/2002 |
| WO | WO 02/18372 | 3/2002 |
| WO | WO 02/24684 | 3/2002 |
| WO | WO 02/30924 | 4/2002 |
| WO | WO 02/34744 | 5/2002 |
| WO | WO 02/44166 | 6/2002 |
| WO | WO 02/48117 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |
| WO | WO 02/092577 | 11/2002 |
| WO | WO 02/092578 | 11/2002 |
| WO | WO 02/097490 | 12/2002 |
| WO | 03/040108 A | 5/2003 |
| WO | WO 03/040108 | 5/2003 |
| WO | WO 03/040109 | 5/2003 |
| WO | WO 03/049740 | 6/2003 |
| WO | WO 03/082831 | 10/2003 |
| WO | WO 2004/064718 | 8/2004 |
| WO | WO 2004/093880 | 11/2004 |
| WO | WO 2005/012290 | 2/2005 |
| WO | WO 2005/013998 | 2/2005 |
| WO | WO 2005/026150 | 3/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | WO 2005/030757 | 4/2005 |
| WO | WO 2005/030765 | 4/2005 |
| WO | WO 2005/051923 | 6/2005 |
| WO | WO 2005/075439 | 8/2005 |
| WO | WO 2005/118572 | 12/2005 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |
| WO | WO 2006/117521 | 11/2006 |
| WO | WO 2006/117523 | 11/2006 |
| WO | WO 2007/034143 | 3/2007 |
| WO | WO 2007/034144 | 3/2007 |
| WO | WO 2007/063291 | 6/2007 |

| | | | |
|---|---|---|---|
| WO | WO 2007/063293 | 6/2007 | |

OTHER PUBLICATIONS

Traxler et al. "Protein tyrosine kinase inhibitors in cancer treatment" Exp. Opin. Ther. Patents 7(6):571-588 (1997).

Traxler et al. "Tyrosine kinase inhibitors in cancer treatment (Part II)" Exp. Opin. Ther. Patents 8(12):1599-1625 (1998).

Tsou et al. "6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity" J. Med. Chem. 44:2719-2734 (2001).

Vema et al. "Design of EGFR kinase inhibitors: a ligand-based approach and its confirmation with structure-based studies" Bioorg Med Chem. 11(21):4643-4653 (2003).

Ballard et al. "Inhibitors of epidermal growth factor receptor tyrosine kinase: Novel C-5 substituted anilinoquinazolines designed to target the ribose pocket" Bioorg Med Chem Lett. 16(6):1633-1637 (2006).

Ballard et al. "5-Substituted 4-anilinoquinazolines as potent, selective and orally active inhibitors of erbB2 receptor tyrosine kinase" Bioorg Med Chem Lett. 15(19):4226-4229 (2005).

Ballard et al. "Inhibitors of epidermal growth factor receptor tyrosine kinase: optimisation of potency and in vivo pharmacokinetics" Bioorg Med Chem Lett. 16(18):4908-4912 (2006).

Harris et al. "Facile synthesis of 7-amino anilinoquinazolines via direct amination of the quinazoline core" Tetrahedron letters 46(43):7381-7384 (2005).

Harris et al. "Selective alkylation of a 6,7-dihydroxyquinazoline" Tetrahedron letters 46(45):7715-7719 (2005).

Hennequin et al. "Novel 4-anilinoquinazolines with C-6 carbon-linked side chains: synthesis and structure-activity relationship of a series of potent, orally active, EGF receptor tyrosine kinase inhibitors" Bioorg Med Chem Lett. 16(10):2672-2676 (2006).

Poster No. P044, Barlaam et al, "Indazolylamino/Anilinoquinazolines Bearing a C-5 Substitution As erbB2 Kinase Inhibitors: Structure-Activity Relationships and Identification of a Candidate Drug" presented at EFMC-ISMC Vienna, Aug. 31-Sep. 4, 2008.

Poster, Ballard et al "Developing a small molecule erbB2 inhibitor:challenges with optimising DMPK properties" presented at DMDG Cambridge Feb. 2008.

Harris et al,"Systematic Variation of a Key Quinazoline Core" presented at the XXII European Colloquium on Heterocyclic Chemistry (XXII ECHC-2006) will be organized in Bari, Italy, on Sep. 2-6, 2006.

Barlaam et al "Indazolylamino/Anilinoquinazolines Bearing a C-5 Substitution As erbB2 Kinase Inhibitors: Structure-Activity Relationships and Identification of a Candidate Drug" at AACR in 2007.

* cited by examiner

QUINAZOLINE DERIVATIVES AND THEIR USE IN THE TREATMENT OF CANCER

CROSS-REFERENCE TO RELATED APPLICATIONS

The present application is a U.S. National Phase Application of International Application No. PCT/GB2004/001799 (filed Apr. 27, 2004) which claims the benefit of GB Application 0309850.6 (filed Apr. 30, 2003).

The invention concerns certain novel quinazoline derivatives, or pharmaceutically-acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol*, 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al, Biochimica et Biophysica Acta, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases e.g. EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to 20 receptor tyrosine kinase and 10 non-receptor tyrosine kinase subfamilies (Robinson et al, *Oncogene*, 2000, 19, 5548-5557).

The receptor tyrosine kinases are of particular importance in the transmission of mitogenic signals that initiate cellular replication. These large glycoproteins, which span the plasma membrane of the cell possess an extracellular binding domain for their specific ligands (such as Epidermal Growth Factor (EGF) for the EGF Receptor). Binding of ligand results in the activation of the receptor's kinase enzymatic activity that is encoded by the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.*, 2000, 19, 3159). One mechanism in which this can be accomplished is by over expression of the receptor at the protein level, generally as a result of gene amplification. This has been observed in many common human cancers (reviewed in Klapper et al., *Adv. Cancer Res.*, 2000, 77, 25) such as breast cancer (Sainsbury et al., *Brit. J. Cancer*, 1988, 58, 458; Guerin et al., *Oncogene Res.*, 1988, 3, 21; Slamon et al., *Science*, 1989, 244, 707; Klijn et al., *Breast Cancer Res. Treat.*, 1994, 29, 73 and reviewed in Salomon et al., *Crit. Rev. Oncol. Hematol.*, 1995, 19, 183), non-small cell lung cancers (NSCLCs) including adenocarcinomas (Cerny et al., *Brit. J. Cancer*, 1986, 54, 265; Reubi et al., *Int. J. Cancer*, 1990, 45, 269; Rusch et al, *Cancer Research*, 1993, 53, 2379; Brabender et al, *Clin. Cancer Res.*, 2001, 7, 1850) as well as other cancers of the lung (Hendler et al., *Cancer Cells*, 1989, 7, 347; Ohsaki et al., *Oncol. Rep.*, 2000, 7, 603), bladder cancer (Neal et al, *Lancet*, 1985, 366; Chow et al, *Clin. Cancer Res.*, 2001, 7, 1957, Zhau et al., *Mol Carcinog.*, 3, 254), oesophageal cancer (Mukaida et al., *Cancer*, 1991, 68, 142), gastrointestinal cancer such as colon, rectal or stomach cancer (Bolen et al., *Oncogene Res.*, 1987, 1, 149; Kapitanovic et al., *Gastroenterology*, 2000, 112, 1103; Ross et al. *Cancer Invest.*, 2001, 19, 554), cancer of the prostate (Visakorpi et al., *Histochem. J.*, 1992, 24, 481; Kumar et al., 2000, 32, 73; Scher et al., *J. Natl. Cancer Inst.*, 2000, 92, 1866), leukaemia (Konaka et al., *Cell* 1984, 37, 1035, Martin-Subero et al., *Cancer Genet Cytoenet.*, 2001, 127, 174), ovarian (Hellstrom et al., *Cancer Res.*, 2001, 61, 2420), head and neck (Shiga et al., *Head Neck*, 2000, 22, 599) or pancreatic cancer (Ovotny et al., *Neoplasma*, 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors, it is widely believed that many tumours become clinically more aggressive and so correlate with a poorer prognosis for the patient (Brabender et al, *Clin. Cancer Res.*, 2001, 7, 1850; Ross et al, *Cancer Investigation*, 2001, 19, 554, Yu et al., *Bioessays*, 2000, 22.7, 673). In addition to these clinical findings, a wealth of pre-clinical information suggests that the erbB family of receptor tyrosine kinases are involved in cellular transformation. This includes the observations that many tumour cell lines over express one or more of the erbB receptors and that EGFR or erbB2 when transfected into non-tumour cells have the ability to transform these cells. This tumorigenic potential has been further verified as transgenic mice that over express erbB2 spontaneously develop tumours in the mammary gland. In addition to this, a number of pre-clinical studies have demonstrated that antiproliferative effects can be induced by knocking out one or more erbB activities by small molecule inhibitors, dominant negatives or inhibitory antibodies (reviewed in Mendelsohn et al., *Oncogene*, 2000, 19, 6550). Thus it has been recognised that inhibitors of these receptor tyrosine kinases should be of value as a selective inhibitor of the proliferation of mammalian cancer cells (Yaish et al. *Science*, 1988, 242, 933, Kolibaba et al, Biochimica et Biophysica Acta, 1997, 133, F217-F248; Al-Obeidi et al, 2000, *Oncogene*, 19, 5690-5701; Mendelsohn et al, 2000, *Oncogene*, 19, 6550-6565). In addition to this pre-clinical data, findings using inhibitory antibodies against EGFR and erbB2 (c-225 and trastuzumab respectively) have proven to be beneficial in the clinic for the treatment of selected solid tumours (reviewed in Mendelsohn et al, 2000, *Oncogene*, 19, 6550-6565).

Amplification and/or activity of members of the erbB type receptor tyrosine kinases have been detected and so have been implicated to play a role in a number of non-malignant proliferative disorders such as psoriasis (Ben-Bassat, *Curr. Pharm. Des.*, 2000, 6, 933; Elder et al., Science, 1989, 243, 811), benign prostatic hyperplasia (BPH) (Kumar et al, *Int. Urol. Nephrol.*, 2000, 32, 73), atherosclerosis and restenosis (Bokemeyer et al., *Kidney Int.*, 2000, 58, 549). It is therefore expected that inhibitors of erbB type receptor tyrosine kinases will be useful in the treatment of these and other non-malignant disorders of excessive cellular proliferation. International Patent Applications WO 96/33977, WO 96/33978, WO 96/33979, WO 96/33980 and WO 96/33981 disclose that certain quinazoline derivatives which bear an anilino substituent at the 4-position possess receptor tyrosine kinase inhibitory activity.

A review of the structure activity relationship of various quinazoline derivatives is disclosed by G. W. Rewcastle et al (J. Med. Chem. 1995, 38, 3428-3487), including a number of 5-substituted compounds. However, such 5-substituted compounds are stated to have low in-vitro activity as EGFR tyrosine kinase inhibitors compared to quinazolines substituted at the 6- and 7-positions.

WO 96/09294 discloses 4-anilinoquinazoline derivatives, including 5-chloro and 5-methoxy substituted quinazoline derivatives as protein tyrosine kinase inhibitors.

WO96/15118 discloses certain 4-anilinoquinazoline derivatives that are substituted on the aniline by certain aryl or heteroaryl groups. The compounds are stated to be Class 1 receptor tyrosine kinase inhibitors. International Patent Application WO 97/03069 also discloses certain 4-substituted quinazoline derivatives and states that the compounds are erbB2 tyrosine kinase inhibitors.

WO97/30034 describes 4-anilinoquinazoline derivatives that are substituted on the aniline by certain aryl or heteroaryl groups and which are also substituted at the 6-position on the quinazoline by certain aryl or heteroaryl groups. These compounds are also Class I receptor tyrosine kinase inhibitors.

WO01/21596 discloses the use of 4-anilinoquinazoline derivatives as aurora 2 kinase inhibitors.

There is no disclosure in WO96/15118, WO 97/03069, WO97/30034 or WO01/21596 of any compounds substituted at the 5-position on the quinazoline ring.

International Patent Application WO01/94341 discloses that certain quinazoline derivatives which carry a 5-substituent are inhibitors of the Src family of non-receptor tyrosine kinases, such as c-Src, c-Yes and c-Fyn.

None of the prior art discloses 4-anilinoquinazolines which are substituted at the 5-position by a pyrrolidinylmethoxy substituent, which is substituted on a ring nitrogen atom by an optionally substituted alkanoyl group.

Surprisingly we have now found that certain 5-substituted quinazoline derivatives possess potent anti-tumour activity. In particular the compounds of the present invention are possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of inhibition of EGFR and/or erbB2 receptor tyrosine kinases.

Generally the compounds of the present invention possess potent inhibitory activity against the erbB receptor tyrosine kinase family, for example by inhibition of EGFR and/or erbB2 and/or erbB4 receptor tyrosine kinases, whilst possessing less potent inhibitory activity against other kinases. Furthermore, many of the compounds of the present invention possess substantially better potency against the EGFR over that of the erbB2 tyrosine kinase. This has the advantage of allowing highly selective EGFR tyrosine kinase inhibition, even within the erbB family of receptors. The invention also includes compounds that are active against all or a combination of EGFR, erbB2 and erbB4 receptor tyrosine kinases, thus potentially providing treatments for conditions mediated by one or more of these receptor tyrosine kinases.

Generally the compounds of the present invention exhibit favourable physical properties such as a high solubility whilst retaining high antiproliferative activity.

According to a first aspect of the invention there is provided a quinazoline derivative of the formula I:

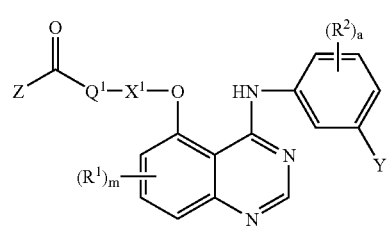

wherein:

$X^1$ is $C(R^3)_2$, wherein each $R^3$, which may be the same or different, is selected from hydrogen and (1-4C)alkyl;

$Q^1$ is pyrrolidinyl;

and wherein $Q^1$ is linked to the group $X^1$—O by a ring carbon atom, and wherein $Q^1$ is substituted at the I-position by the group of the formula ZC(O);

Z is selected from (1-4C)alkyl, halogeno-(1-4C)alkyl, hydroxy-(1-4C)alkyl, (1-4C)alkoxy-(1-4C)alkyl, amino-(1-4C)alkyl, (1-4C)alkylamino-(1-4C)alkyl and di-[(1-4C)alkyl]amino-(1-4C)alkyl, or Z is $Q^2$, wherein $Q^2$ is heterocyclyl or heterocyclyl-(1-4C)alkyl, and wherein any $CH_2$ or $CH_3$ group within a Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, formyl, mercapto, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within $Q^1$ or Z optionally bears one or more (for example 1, 2 or 3) substituents, which may be the same or different selected from halogeno, trifluoromethyl, cyano, nitro, hydroxy, amino, carboxy, carbamoyl, sulfamoyl, formyl, mercapto, (1-6C)alkyl, (2-6C)alkenyl, (2-6C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, and N-(1-6C)alkyl-(1-6C)alkanesulfonylamino, or from a group of the formula:

$$-X^2-R^4$$

wherein $X^2$ is a direct bond or is selected from O, CO and $N(R^5)$, wherein $R^5$ is hydrogen or (1-6C)alkyl, and $R^4$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl, (2-6C)alkanoyloxy-(1-6C)alkyl and (1-6C)alkoxycarbonyl-(1-6C)alkyl, and wherein any heterocyclyl group within $Q^1$ or Z optionally bears 1 or 2 oxo or thioxo substituents;

m is 0, 1 or 2 and $R^1$ when present is located at the 6- and/or 7-position;

each $R^1$ group, which may be the same or different, is selected from hydroxy, (1-6C)alkoxy, (2-6C)alkenyloxy, (2-6C)alkynyloxy, or from a group of the formula:

$$Q^3-X^3-$$

wherein $X^3$ is a direct bond or is O, and $Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, or $(R^1)_m$ is (1-3C)alkylenedioxy, and wherein adjacent carbon atoms in any (2-6C)alkylene chain within a $R^1$ substituent are optionally separated by the insertion into the chain of a group selected from O, S, SO, $SO_2$, $N(R^6)$, CO, $CH(OR^6)$, $CON(R^6)$, $N(R^6)CO$, $SO_2N(R^6)$, $N(R^6)SO_2$, CH=CH and C≡C wherein $R^6$ is hydrogen or (1-6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^4-X^4-$$

wherein $X^4$ is a direct bond or is selected from CO and $N(R^7)CO$, wherein $R^7$ is hydrogen or (1-6C)alkyl, and $Q^4$ is heterocyclyl or heterocyclyl-(1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$-X^5-Q^5$$

wherein $X^5$ is a direct bond or is selected from O, S, SO, $SO_2$, $N(R^8)$, CO, $CH(OR^8)$, $CON(R^8)$, $N(R^8)CO$, $SO_2N(R^8)$, $N(R^8)SO_2$, $C(R^8)_2O$, $C(R^8)_2S$ and $C(R^8)_2N(R^8)$, wherein $R^8$ is hydrogen or (1-6C)alkyl, and $Q^5$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein any heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, and N-(1-6C)alkyl-(1-6C)alkanesulfonylamino, or from a group of the formula:

$$-X^6-R^9$$

wherein $X^6$ is a direct bond or is selected from O, $N(R^{10})$ and C(O), wherein $R^{10}$ is hydrogen or (1-6C)alkyl, and $R^9$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, and wherein any heterocyclyl group within a substituent on $R^1$ optionally bears 1 or 2 oxo or thioxo substituents;

Y is selected from halogeno, cyano, trifluoromethyl, (1-6C)alkyl, (2-6C)alkenyl, (2-6C)alkynyl and (1-6C)alkoxy;

each $R^2$, which may be the same or different, is selected from halogeno, cyano, nitro, hydroxy, amino, carboxy, carbamoyl, sulfamoyl, trifluoromethyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, N-(1-6C)alkylsulfamoyl, N,N-di-[(1-6C)alkyl]sulfamoyl; and a is 0, 1, 2, 3 or 4;

or a pharmaceutically acceptable salt thereof.

According to another aspect of the invention there is provided a quinazoline derivative of the formula I as hereinbefore defined wherein $X^1$, $Q^1$, $R^1$, $R^2$, a, m and Y are as hereinbefore defined; and Z is selected from halogeno-(1-4C)alkyl, hydroxy-(1-4C)alkyl, (1-4C)alkoxy-(1-4C)alkyl, amino-(1-4C)alkyl, (1-4C)alkylamino-(1-4C)alkyl and di-[(1-4C)alkyl]amino-(1-4C)alkyl, or Z is $Q^2$, wherein $Q^2$ is heterocyclyl or heterocyclyl-(1-4C)alkyl, and wherein the heterocyclyl in $Q^2$ contains at least 1 nitrogen heteroatom, and optionally 1 or 2 further heteroatoms selected from oxygen, nitrogen and sulfur, and wherein any $CH_2$ or $CH_3$ group within a Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, formyl, mercapto, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within $Q^1$ or Z optionally bears one or more (for example 1, 2 or 3) substituents, which may be the same or different selected from halogeno, trifluoromethyl, cyano, nitro, hydroxy, amino, carboxy, carbamoyl, sulfamoyl, formyl, mercapto, (1-6C)alkyl, (2-6C)alkenyl, (2-6C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, and N-(1-6C)alkyl-(1-6C)alkanesulfonylamino, or from a group of the formula:

—$X^2$—$R^4$ wherein $X^2$ is a direct bond or is selected from O, CO and N($R^5$), wherein $R^5$ is hydrogen or (1-6C)alkyl, and $R^4$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl, (2-6C)alkanoyloxy-(1-6C)alkyl and (1-6C)alkoxycarbonyl-(1-6C)alkyl, and wherein any heterocyclyl group within $Q^1$ or Z optionally bears 1 or 2 oxo or thioxo substituents;

or a pharmaceutically acceptable salt thereof.

In this specification the generic term "alkyl" includes both straight-chain and branched-chain alkyl groups such as propyl, isopropyl and tert-butyl, and (3-7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes methoxy, ethoxy, cyclopropyloxy and cyclopentyloxy, (1-6C)alkylamino includes methylamino, ethylamino, cyclobutylamino and cyclohexylamino, and di-[(1-6Calkyl]amino includes dimethylamino, diethylamino, N-cyclobutyl-N-methylamino and N-cyclohexyl-N-ethylamino.

It is to be understood that, insofar as certain of the compounds of formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that the present invention includes in its definition any and all tautomeric forms of the compounds of the formula I which possess the above mentioned activity.

It is also to be understood that in so far as certain compounds of the formula I may exist in solvated forms as well as unsolvated forms, for example, hydrated forms, the present invention includes any and all such solvated forms, which possess the above mentioned activity.

Suitable values for the generic radicals referred to above include those set out below.

A suitable value for any one of the 'Q' groups ($Q^3$ and $Q^5$) when it is (3-7C)cycloalkyl or for the (3-7C)cycloalkyl group within a 'Q' group is, for example, cyclopropyl, cyclobutyl, cyclopentyl, cyclohexyl, cycloheptyl or bicyclo[2.2.1]heptyl and a suitable value for any one of the 'Q' groups ($Q^3$ and $Q^5$) when it is (3-7C)cycloalkenyl or for the (3-7C)cycloalkenyl group within a 'Q' group is, for example, cyclobutenyl, cyclopentenyl, cyclohexenyl or cycloheptenyl.

A suitable value for any one of the 'Q' groups ($Q^2$ to $Q^5$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulfur, which, unless specified otherwise, may be carbon or nitrogen linked. Examples of suitable values of "heterocyclyl" include oxiranyl, oxetanyl, azetidinyl, tetrahydrofuranyl, tetrahydropyranyl, oxepanyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl, decahydroisoquinolinyl or decahydroquinolinyl, particularly tetrahydrofuranyl, tetrahydropyranyl, pyrrolidinyl, morpholinyl, 1,4-oxazepanyl, thiomorpholinyl 1,1-dioxotetrahydro-4-H-1,4-thiazinyl, piperidinyl or piperazinyl, more particularly tetrahydrofuran-3-yl, tetrahydropyran-4-yl, tetrahydrothien-3-yl, tetrahydrothiopyran-4-yl, pyrrolidin-1-yl, pyrrolidin-2-yl, pyrrolidin-3-yl, morpholino, morpholin-2-yl, morpholin-3-yl, 1,1-dioxotetrahydro-4H-1,4-thiazin-4-yl, piperidino, piperidin-4-yl, piperidin-3-yl, piperidin-2-yl, piperazin-1-yl or piperazin-2-yl. A nitrogen or sulfur atom within a heterocyclyl group may be oxidized to give the corresponding N or S oxide, for example 1,1-dioxotetrahydrothienyl, 1-oxotetrahydrothienyl, 1,1-dioxotetrahydrothiopyranyl or 1-oxotetrahydrothiopyranyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

Particular values for $Q^1$ is pyrrolidin-2-yl and pyrrolidin-3-yl.

Particular values for $Q^2$ when it is heterocyclyl containing at least 1 nitrogen atom and optionally 1 or 2 further heteroatoms selected from oxygen, nitrogen and sulfur, include the heterocycles above containing at least 1 nitrogen atom, particularly a fully saturated 4, 5, 6 or 7-membered monocyclic or bicyclic (particularly monocyclic) heterocyclyl group containing 1 nitrogen heteroatom and optionally 1 further heteroatom selected from oxygen, nitrogen and sulfur, particularly such groups that are linked by a ring nitrogen atom to the alkyl or carbonyl in formula I. When $Q^2$ is linked via a ring nitrogen this nitrogen atom is not quaternised, i.e. a neutral compound is formed. Suitable values represented by $Q^2$ include the heterocyclyl groups listed above, more particularly pyrrolidinyl, piperidinyl, piperazinyl or morpholinyl, still more particularly pyrrolidin-1-yl, piperidino, piperazin-1-yl or morpholino.

A suitable value for a 'Q' group when it is heterocyclyl-(1-6C)alkyl is, for example, heterocyclylmethyl, 2-heterocyclylethyl and 3-heterocyclylpropyl. The invention comprises corresponding suitable values for 'Q' groups when, for example, rather than a heterocyclyl-(1-6C)alkyl group, an (3-7C)cycloalkyl-(1-6C)alkyl or (3-7C)cycloalkenyl-(1-6C)alkyl group is present. It is to be understood that when a 'Q' group, for example $Q^2$ is heterocyclyl-(1-4C)alkyl, $Q^2$ is attached to the carbonyl group in formula I via the (1-4C)alkyl portion of the heterocyclyl-(1-4C)alkyl group. For example when $Q^2$ is morpholinomethyl, the group Z—C(O)— in formula I so formed is a morpholinoacetyl group.

Suitable values for any of the 'R' groups ($R^1$ to $R^{10}$), or for various groups within an $R^1$ substituent, or for various groups within $Q^1$, or for Z or for various groups within Z, or for Y include:—

| | |
|---|---|
| for halogeno | fluoro, chloro, bromo and iodo; |
| for (1-6C)alkyl: | methyl, ethyl, propyl, isopropyl and tert-butyl; |
| for (2-8C)alkenyl: | vinyl, isopropenyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulfinyl: | methylsulfinyl and ethylsulfinyl; |
| for (1-6C)alkylsulfonyl: | methylsulfonyl and ethylsulfonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl and propionyl; |
| for (2-6C)alkanoyloxy: | acetoxy and propionyloxy; |
| for (2-6C)alkanoylamino: | acetamido and propionamido; |
| for N-(1-6C)alkyl-(2-6C)alkanoylamino: | N-methylacetamido and N-methylpropionamido; |
| for amino(2-6C)alkanoyl: | aminoacetyl and 2-aminopropionyl; |
| for N-(1-6C)alkylamino(2-6C)alkanoyl: | N-methylaminoacetyl and 2-(N-methylaminopropionyl; |
| for N,N-di-[(1-6C)alkyl]amino(2-6C)alkanoyl: | N,N-di-methylaminoacetyl; |
| for N-(1-6C)alkylsulfamoyl: | N-methylsulfamoyl and N-ethylsulfamoyl; |
| for N,N-di-[(1-6C)alkyl]sulfamoyl: | N,N-dimethylsulfamoyl; |
| for (1-6C)alkanesulfonylamino: | methanesulfonylamino and ethanesulfonylamino; |
| for N-(1-6C)alkyl-(1-6C)alkanesulfonylamino: | N-methylmethanesulfonylamino and N-methylethanesulfonylamino; |
| for (3-6C)alkenoylamino: | acrylamido, methacrylamido and crotonamido; |
| for N-(1-6C)alkyl-(3-6C)alkenoylamino: | N-methylacrylamido and N-methylcrotonamido; |
| for (3-6C)alkynoylamino: | propiolamido; |
| for N-(1-6C)alkyl-(3-6C)alkynoylamino: | N-methylpropiolamido; |
| for amino-(1-6C)alkyl: | aminomethyl, 2-aminoethyl, 1-aminoethyl and 3-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |

| | |
|---|---|
| for di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl; |
| for halogeno-(1-6C)alkyl: | chloromethyl, 2-chloroethyl, 1-chloroethyl and 3-chloropropyl; |
| for hydroxy-(1-6C)alkyl: | hydroxymethyl, 2-hydroxyethyl, 1-hydroxyethyl and 3-hydroxypropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for cyano-(1-6C)alkyl: | cyanomethyl, 2-cyanoethyl, 1-cyanoethyl and 3-cyanopropyl; |
| for carboxy-(1-6C)alkyl: | carboxymethyl, 2-carboxyethyl, 1-carboxyethyl and 3-carboxypropyl; |
| for (2-6C)alkanoylamino-(1-6C)alkyl: | acetamidomethyl, propionamidomethyl and 2-acetamidoethyl; |
| for (1-6C)alkoxycarbonyl-(1-6C)alkyl: | methoxycarbonylmethyl, 2-methoxycarbonylethyl and 2-ethoxycarbonylethyl; |
| for (2-6C)alkanoyl-(1-6C)alkyl: | acetylmethyl and 2-acetylethyl; |
| for (2-6C)alkanoyloxy-(1-6C)alkyl: | acetoxymethyl, 2-acetoxyethyl, propionyloxymethyl and 2-propionyloxyethyl; |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl; |
| for carbamoyl-(1-6C)alkyl: | carbamoylmethyl, 1-carbamoylethyl, 2-carbamoylethyl and 3-carbamoylpropyl; |
| for N-(1-6C)alkylcarbamoyl-(1-6C)alkyl: | N-methylcarbamoylmethyl, N-ethylcarbamoylmethyl, N-propylcarbamoymethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; and |
| for N,N-di[(1-6C)alkyl]carbamoyl-(1-6C)alkyl: | N,N-dimethylcarbamoylmethyl, N,N-diethylcarbamoylmethyl 2-(N,N-dimethylcarbamoyl)ethyl, and 3-(N,N-dimethylcarbamoyl)propyl. |

A suitable value for $(R^1)_m$ when it is a (1-3C)alkylenedioxy group is, for example, methylenedioxy or ethylenedioxy and the oxygen atoms thereof occupy adjacent ring positions.

When in this specification reference is made to a (1-4C) alkyl group it is to be understood that such groups refer to alkyl groups containing up to 4 carbon atoms. A skilled person will realise that representative examples of such groups are those listed above under (1-6C)alkyl that contain up to 4 carbon atoms, such as methyl, ethyl, propyl and butyl. Similarly, reference to a (1-3C)alkyl group refers to alkyl groups containing up to 3 carbon atoms such as methyl, ethyl and propyl. A similar convention is adopted for the other groups listed above such as (1-4C)alkoxy, (2-4C)alkenyl, (2-4C) alkynyl and (2-4C)alkanoyl.

When, as defined hereinbefore, a $CH_3$ group within a $R^1$ substituent bears a group of the formula —$X^5$—$Q^5$ and, for example, $X^5$ is a $C(R^8)_2O$ linking group, it is the carbon atom, not the oxygen atom, of the $C(R^8)_2O$ linking group which is attached to the $CH_3$ group and the oxygen atom is linked to the $Q^5$ group. Similarly when, as defined hereinbefore, a terminal $CH_2$= group within a $R^1$ substituent bears a group of the formula $Q^4$—$X^4$— and, for example, $X^4$ is $N(R^7)CO$, it is the carbonyl group of the $N(R^7)CO$ group which is attached to the $CH_2$= group and the $N(R^7)$ group which is attached to $Q^4$.

As defined hereinbefore, adjacent carbon atoms in any (2-6C)alkylene chain within a $R^1$ substituent may be optionally separated by the insertion into the chain of a group such as O, $CON(R^5)$, $N(R^5)$ or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group. It is to be understood that the term (2-6C)alkylene chain refers to any $CH_2CH_2$ group within $R^1$ and includes, for example alkylene chains within a (1-6C)alkyl, (1-6C)alkoxy, (2-8C)alkenyl, (2-8C)alkenyloxy, (2-8C)alkynyl and (2-8C)alkynyloxy group. For example the insertion of a $N(CH_3)$ group between the third and fourth carbon atoms in a hex-5-enyloxy group in $R^1$ gives rise to a 3-(N-methyl-N-alkylamino)propoxy group.

When, as defined hereinbefore, any $CH_2$=CH— or HC≡C— group within a $R^1$ substituent optionally bears at the terminal $CH_2$= or HC≡ position a substituent such as a group of the formula $Q^4$—$X^4$— wherein $X^4$ is, for example, NHCO and $Q^4$ is a heterocyclyl-(1-6C)alkyl group, suitable $R^1$ substituents so formed include, for example, N-[heterocyclyl-(1-6C)alkyl]carbamoylvinyl groups such as N-(2-pyrrolidin-1-ylethyl)carbamoylvinyl or N-[heterocyclyl-(1-6C)alkyl]carbamoylethynyl groups such as N-(2-pyrrolidin-1-ylethyl)carbamoylethynyl.

When, as defined hereinbefore, any $CH_2$ or $CH_3$ group within a $R^1$ substituent optionally bears on each said $CH_2$ or $CH_3$ group one or more halogeno or (1-6C)alkyl substituents, there are suitably 1 or 2 halogeno or (1-6C)alkyl substituents present on each said $CH_2$ group and there are suitably 1, 2 or 3 such substituents present on each said $CH_3$ group.

When, as defined hereinbefore, any $CH_2$ or $CH_3$ group within a $R^1$ substituent optionally bears on each said $CH_2$ or $CH_3$ group a substituent as defined hereinbefore, suitable $R^1$ substituents so formed include, for example, hydroxy-substituted heterocyclyl-(1-6C)alkoxy groups such as 2-hydroxy- 3-piperidinopropoxy and 2-hydroxy-3-morpholinopropoxy, hydroxy-substituted amino-(2-6C)alkoxy groups such as 3-amino-2-hydroxypropoxy, hydroxy-substituted (1-6C)alkylamino-(2-6C)alkoxy groups such as 2-hydroxy-3-methylaminopropoxy, hydroxy-substituted di-[(1-6C)alkyl]amino-(2-6C)alkoxy groups such as 3-dimethylamino-2-hydroxypropoxy, hydroxy-substituted (1-6C)alkoxy groups such as 2-hydroxyethoxy, (1-6C)alkoxy-substituted (1-6C)alkoxy groups such as 2-methoxyethoxy and 3-ethoxypropoxy, (1-6C)alkylsulfonyl-substituted (1-6C)alkoxy groups such as 2-methylsulfonylethoxy and heterocyclyl-substituted (1-6C)alkylamino-(1-6C)alkoxy groups such as 2-(2-morpholinoethylamino)ethoxy, 2-(2-piperazin-1-ylethylamino)ethoxy and 2-(3-morpholinopropylamino)ethoxy.

Similar considerations apply to the attachments and substitutions within the Z, $Q^1$ and $X^1$ groups.

It is to be understood that the 2- and 8-positions on the quinazoline ring are unsubstituted.

A suitable pharmaceutically-acceptable salt of a compound of the formula I is, for example, an acid-addition salt of a compound of the formula I, for example an acid-addition salt with an inorganic or organic acid such as hydrochloric, hydrobromic, sulfuric, trifluoroacetic, citric or maleic acid; or, for example, a salt of a compound of the formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinazoline derivatives of the formula I, or pharmaceutically-acceptable salts thereof, wherein, unless otherwise stated, each of $R^1$, $R^2$, Y, Z, $Q^1$, $X^1$, m and a has any of the meanings defined hereinbefore or in paragraphs (a) to (zzz) hereinafter:—

(a) each $R^1$ group, which may be the same or different, is selected from hydroxy, (1-6C)alkoxy, (2-6C)alkenyloxy, (2-6C)alkenyloxy, or from a group of the formula:

$$Q^3—X^3—$$

wherein $X^3$ is a direct bond or is O, and $Q^3$ is (3-7C)cycloalkyl, (3-7C)cycloalkyl-(1-6C)alkyl, heterocyclyl or heterocyclyl-(1-6C)alkyl, and wherein adjacent carbon atoms in any (2-6C)alkylene chain within a $R^1$ substituent are optionally separated by the insertion into the chain of a group selected from O, N($R^6$), CON($R^6$), N($R^6$)CO, CH=CH and C≡C wherein $R^6$ is hydrogen or (1-6C)alkyl, and wherein any $CH_2$=CH— or HC≡C— group within a $R^1$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^4—X^4—$$

wherein $X^4$ is a direct bond or is selected from CO and N($R^7$)CO, wherein $R^7$ is hydrogen or (1-6C)alkyl, and $Q^4$ is heterocyclyl or heterocyclyl-(1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)alkylamino, di-[(1-6C)alkyl]amino, N-(1-6C)alkylcarbamoyl and N,N-di-[(1-6C)alkyl]carbamoyl, or from a group of the formula:

$$—X^5—Q^5$$

wherein $X^5$ is a direct bond or is selected from O, N($R^8$), CON($R^8$), N($R^8$)CO and C($R^8$)$_2$O, wherein $R^8$ is hydrogen or (1-6C)alkyl, and $Q^5$ is heterocyclyl or heterocyclyl-(1-6C)alkyl, and wherein any heterocyclyl group within a substituent on $R^1$ optionally bears 1, 2 or 3 substituents, which may be the same or different, selected from halogeno, trifluoromethyl, cyano, nitro, hydroxy, amino, carbamoyl, (1-6C)alkyl, (2-8C)alkenyl, (2-8C)alkynyl, (1-6C)alkoxy, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, or from a group of the formula:

$$—X^6—R^9$$

wherein $X^6$ is a direct bond or is selected from O and N($R^{10}$), wherein $R^{10}$ is hydrogen or (1-6C)alkyl, and $R^9$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl and N,N-di-[(1-6C)alkyl]carbamoyl-(1-6C)alkyl, and wherein any heterocyclyl group within a substituent on $R^1$ optionally bears 1 or 2 oxo substituents;

(b) each $R^1$ group, which may be the same or different, is selected from hydroxy, (1-6C)alkoxy, (2-6C)alkenyloxy, (2-6C)alkynyloxy, or from a group of the formula:

$$Q^3—X^3—$$

wherein $X^3$ is a direct bond or is O, and $Q^3$ is heterocyclyl or heterocyclyl-(1-6C)alkyl, and wherein adjacent carbon atoms in any (2-6C)alkylene chain within a $R^1$ substituent are optionally separated by the insertion into the chain of a group selected from O, N($R^6$), CON($R^6$), N($R^6$)CO, CH=CH and C≡C wherein $R^6$ is hydrogen or (1-6C)alkyl, and wherein any $CH_2$=CH— or HC≡C— group within a $R^1$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)alkylamino, di-[(1-6C)alkyl]amino, N-(1-6C)alkylcarbamoyl and N,N-di-[(1-6C)alkyl]carbamoyl, or from a group of the formula:

$$—X^5—Q^5$$

wherein $X^5$ is a direct bond or is selected from O, N($R^8$), CON($R^8$), N($R^8$)CO and C($R^8$)$_2$O, wherein $R^5$ is hydrogen or (1-6C)alkyl, and $Q^5$ is heterocyclyl or heterocyclyl-(1-6C)alkyl, and wherein any heterocyclyl group within a substituent on $R^1$ optionally bears 1, 2 or 3 substituents, which may be the same or different, selected from halogeno, trifluoromethyl, hydroxy, amino, carbamoyl, (1-6C)alkyl, (2-8C)alkenyl, (2-8C)alkynyl, (1-6C)alkylsulfonyl, (1-6C)alkylamino, di-[(1-6C)alkyl]amino, $\underline{N}$-(1-6C)alkylcarbamoyl, $\underline{N}$,$\underline{N}$-di-[(1-6C)alkyl]carbamoyl, (2-6C)alkanoyl, or from a group of the formula:

—$X^6$—$R^9$ wherein $X^6$ is a direct bond or is selected from O and N($R^{10}$), wherein $R^{10}$ is hydrogen or (1-6C)alkyl, and $R^9$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl, and wherein any heterocyclyl group within a substituent on $R^1$ optionally bears 1 or 2 oxo substituents;

(c) each $R^1$ group, which may be the same or different, is selected from hydroxy, (1-6C)alkoxy, (2-6C)alkenyloxy and (2-6C)alkynyloxy, and wherein adjacent carbon atoms in any (2-6C)alkylene chain within a $R^1$ substituent are optionally separated by the insertion into the chain of a group selected from O, N($R^6$), CON($R^6$), N($R^6$)CO, CH=CH and C≡C wherein $R^6$ is hydrogen or (1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)alkylamino, di-[(1-6C)alkyl]amino, $\underline{N}$-(1-6C)alkylcarbamoyl and $\underline{N}$,$\underline{N}$-di-[(1-6C)alkyl]carbamoyl;

(d) each $R^1$ which may be the same or different, are selected from hydroxy, methoxy, ethoxy, propoxy, isopropyloxy, 2-hydroxyethoxy, 2-fluoroethoxy, cyclopropylmethoxy, 2-cyclopropylethoxy, vinyloxy, alkyloxy, ethynyloxy, 2-propynyloxy, tetrahydrofurfuryloxy, 2-(tetrahydrofuran-2-yl)ethoxy, 3-(tetrahydrofuran-2-yl)propoxy, 2-(tetrahydrofuran-3-yl)ethoxy, 3-(tetrahydrofuran-3-yl)propoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4$\underline{H}$-1,4-thiazin-4-yl)ethoxy, 3-(1,1-dioxotetrahydro-4$\underline{H}$-1,4-thiazinyl)propoxy, 2-piperidinoethoxy, 3-piperidinopropoxy, piperidin-3-yloxy, piperidinyloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, pyrrolidin-1-yl, morpholino, piperidino and piperazin-1-yl, and wherein adjacent carbon atoms in any (2-6C)alkylene chain within a $R^1$ substituent are optionally separated by the insertion into the chain of a group selected from O, NH, N($CH_3$), CH=CH and C≡C, and when $R^1$ is a vinyloxy, alkyloxy, ethynyloxy or 2-propynyloxy group, the $R^1$ substituent optionally bears at the terminal $CH_2$= or HC≡ position a substituent selected from $\underline{N}$-(2-dimethylaminoethyl)carbamoyl, $\underline{N}$-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$Q^4$—$X^4$— wherein $X^4$ is a direct bond or is NHCO or N($CH_3$)CO and $Q^4$ is pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-1-ylethyl, piperazin-1-ylmethyl, 2-piperazin-1-ylethyl, 3-piperazin-1-ylpropyl or 4-piperazin-1-ylbutyl, and wherein any $CH_2$ group which is attached to 2 carbon atoms (other than a $CH_2$ group within a heterocyclyl ring) or any $CH_3$ group which is attached to a carbon atom within a $R^1$ substituent optionally bears on each said $CH_2$ or $CH_3$ group a substituent selected from hydroxy, amino, methoxy, ethoxy, methylsulfonyl, methylamino and dimethylamino, and wherein any heterocyclyl group within a substituent on $R^1$ optionally bears 1 or 2 substituents, which may be the same or different, selected from fluoro, chloro, trifluoromethyl, hydroxy, amino, methylamino, ethylamino, dimethylamino, diethylamino, carbamoyl, methyl, ethyl, n-propyl, isopropyl and methoxy, and any piperidin-3-ylmethyl, piperidin-4-ylmethyl, 2-piperazin-1-ylethylamino, 3-piperazin-1-ylpropylamino, or piperazin-1-yl group within a $R^1$ substituent is optionally $\underline{N}$-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, acetyl or propionyl, and wherein any heterocyclyl group within a substituent on $R^1$ optionally bears 1 or 2 oxo substituents;

(e) m is 1 and the $R^1$ group is located at the 7-position and is selected from hydroxy, methoxy, ethoxy, propoxy, butoxy, and wherein adjacent carbon atoms in any (2-6C)alkylene chain within a $R^1$ substituent are optionally separated by the insertion into the chain of a group selected from O, NH, N($CH_3$), CO, CONH and NHCO, and wherein any $CH_2$ group which is attached to 2 carbon atoms (other than a $CH_2$ group within a heterocyclyl ring) or any $CH_3$ group which is attached to a carbon atom within a $R^1$ substituent optionally bears on each said $CH_2$ or $CH_3$ group a substituent selected from hydroxy, methoxy, ethoxy and methylsulfonyl, or from a group of the formula:

—$X^5$—$Q^5$ wherein $X^5$ is a direct bond or is selected from O, NH and N($CH_3$) and $Q^5$ is selected from pyrrolidin-1-yl, pyrrolidin-2-yl, pyrrolidin-3-yl, morpholino, piperidino, piperidin-3-yl, piperidin-4-yl, homopiperidin-1-yl, piperazin-1-yl and homopiperazin-1-yl, and wherein any heterocyclyl group within a substituent on $R^1$ optionally bears 1 or 2 substituents, which may be the same or different, selected from fluoro, chloro, trifluoromethyl, hydroxy, methyl, ethyl, n-propyl, isopropyl, methoxy, ethoxy, 2-methoxyethoxy, 2-hydroxyethoxy, 3-hydroxypropoxy, 3-methoxypropoxy, acetyl and methylsulfonyl, and wherein any heterocyclyl group within a substituent on $R^1$ optionally bears 1 or 2 oxo substituents;

(f) m is 1 and the $R^1$ group is located at the 7-position and is selected from hydroxy, methoxy, ethoxy, propoxy, butoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy or 3-homopiperazin-1-ylpropoxy, and wherein adjacent carbon atoms in any (2-6C)alkylene chain within a $R^1$ substituent are optionally separated by the insertion into the chain of a group selected from O, NH, N(CH$_3$), CH=CH and C≡C, and wherein any CH$_2$ group which is attached to 2 carbon atoms (other than a CH$_2$ group within a heterocyclyl ring) or any CH$_3$ group which is attached to a carbon atom within a $R^1$ substituent optionally bears on each said CH$_2$ or CH$_3$ group a substituent selected from hydroxy, methoxy and methylsulfonyl, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylamino and dimethylamino, and wherein any heterocyclyl group within a substituent on $R^1$ optionally bears 1 or 2 oxo substituents;

(g) m is 1 and the $R^1$ group is located at the 7-position and is selected from hydroxy, methoxy, ethoxy, isopropyloxy, propoxy, butoxy, 2-pyrrolidin-1-ylethoxy, 3-pyrrolidin-1-ylpropoxy, 2-piperidinoethoxy, 3-piperidinopropoxy, 2-piperidin-3-ylethoxy, 3-piperidin-3-ylpropoxy, 2-piperidin-4-ylethoxy, 3-piperidin-4-ylpropoxy, 2-piperazin-1-ylethoxy, 3-piperazin-1-ylpropoxy, 2-morpholinoethoxy, 3-morpholinopropoxy, 2-homopiperidinoethoxy, 3-homopiperidinopropoxy, 2-homopiperazin-1-ylethoxy and 3-homopiperazin-1-ylpropoxy, and wherein any terminal CH$_3$ group within a (1-6C) alkoxy chain in a $R^1$ substituent optionally bears on the terminal CH$_3$ group 1, 2 or 3 fluoro substituents or a substituent selected from hydroxy and methoxy, and wherein any CH$_2$ group which is attached to 2 carbon atoms (other than a CH$_2$ group within a heterocyclyl ring) within a $R^1$ substituent optionally bears on each said CH$_2$ a hydroxy substituent, and wherein any heterocyclyl group within a $R^1$ substituent optionally bears one or more substituents (for example 1, 2 or 3 substituents) selected from fluoro and chloro, or a substituent selected from hydroxy, methyl, ethyl, isopropyl, 2-hydroxyethyl and 2-methoxyethyl;

(h) m is 1 and $R^1$ is located at the 7-position and is selected from methoxy, ethoxy, propoxy, isopropyloxy, cyclopropylmethoxy, 2-hydroxyethoxy, 2-fluoroethoxy, 2-methoxyethoxy, 2-ethoxyethoxy, 2,2-difluoroethoxy, 2,2,2-trifluoroethoxy and 3-hydroxy-3-methylbutoxy;

(i) m is 1 and $R^1$ is located at the 7-position and is selected from (1-4C)alkoxy, hydroxy-(1-4C)alkoxy and (1-4C)alkoxy (1-4C)alkoxy;

(j) m is 1 and $R^1$ is located at the 7-position and is selected from methoxy, ethoxy, propoxy, isopropoxy, 2-hydroxyethoxy, 2-methoxyethoxy 2-ethoxyethoxy, 3-hydroxypropoxy, 2-hydroxypropoxy, 3-methoxypropoxy and 2-methoxypropoxy;

(k) m is 1 and $R^1$ is located at the 7-position and is selected from methoxy, ethoxy, 2-methoxyethoxy and 2-ethoxyethoxy;

(l) m is 1 and $R^1$ is located at the 7-position and is (1-4C) alkoxy (particularly methoxy);

(m) m is 0;

(n) m is 1 and $R^1$ is located at the 7-position and $R^1$ has any of the values defined in (a) to (d) above;

(o) $X^1$ is C(R$^3$)$_2$, wherein each R$^3$, which may be the same or different, is selected from hydrogen and methyl;

(p) $X^1$ is CH$_2$;

(q) $Q^1$ is selected from pyrrolidin-2-yl and pyrrolidin-3-yl, and wherein the group of the formula ZC(O) is attached at the 1-position on $Q^1$, and wherein $Q^1$ optionally bears one or more (for example 1, 2 or 3) substituents, which may be the same or different selected from halogeno, trifluoromethyl, hydroxy, carbamoyl, (1-4C)alkyl, (1-4C)alkoxy, N-(1-4C)alkylcarbamoyl and N, N-di-[(1-4C)alkyl]carbamoyl, and wherein $Q^1$ optionally bears an oxo substituent;

(r) $Q^1$ is selected from pyrrolidin-2-yl and pyrrolidin-3-yl, and wherein the group of the formula ZC(O) is attached at the 1-position on $Q^1$, and wherein $Q^1$ optionally bears one or more (for example 1, 2 or 3) substituents, which may be the same or different selected from fluoro, chloro, hydroxy, carbamoyl, (1-4C) alkyl, (1-4C)alkoxy, N-(1-4C)alkylcarbamoyl and N, N-di-[(1-4C)alkyl]carbamoyl, and wherein $Q^1$ optionally bears an oxo substituent;

(s) $Q^1$ is pyrrolidin-2-yl, and wherein the group of the formula ZC(O) is attached at the I-position in $Q^1$, and wherein $Q^1$ optionally bears one or more (for example 1, 2 or 3) substituents, which may be the same or different selected from fluoro, chloro, hydroxy, carbamoyl, (1-4C) alkyl, (1-4C)alkoxy, N-(1-4C)alkylcarbamoyl and N, N-di-[(1-4C)alkyl]carbamoyl, and wherein $Q^1$ optionally bears an oxo substituent;

(t) $Q^1$ is pyrrolidin-3-yl, and wherein the group of the formula ZC(O) is attached at the 1-position in $Q^1$, and wherein $Q^1$ optionally bears one or more (for example 1, 2 or 3) substituents, which may be the same or different selected from fluoro, chloro, hydroxy, carbamoyl, (1-4C) alkyl, (1-4C)alkoxy, N-(1-4C)alkylcarbamoyl and N, N-di-[(1-4C)alkyl]carbamoyl, and wherein $Q^1$ optionally bears an oxo substituent;

and wherein $Q^1$ optionally bears an oxo substituent;

(u) $Q^1$ is selected from pyrrolidin-2-yl and pyrrolidin-3-yl, and wherein the group of the formula ZC(O) is attached at the 1-position in $Q^1$, and wherein $Q^1$ optionally bears 1 or 2 substituents, which may be the same or different selected from hydroxy, (1-4C) alkyl and (1-4C)alkoxy, and wherein $Q^1$ optionally bears an oxo substituent;

(v) $Q^1$ is pyrrolidin-2-yl, and wherein the group of the formula ZC(O) is attached at the 1-position in $Q^1$, and wherein $Q^1$ optionally bears 1 or 2 substituents, which may be the same or different, selected from hydroxy, (1-4C) alkyl, (1-4C)alkoxy, hydroxy-(1-4C)alkyl, (1-4C)alkoxy-(1-4C)alkyl, hydroxy-(1-4C)alkoxy, (1-4C)alkoxy-(1-4C) alkoxy, and wherein $Q^1$ optionally bears an oxo substituent;

(w) $Q^1$ is pyrrolidin-2-yl,
and wherein the group of the formula ZC(O) is attached at the 1-position in $Q^1$,
and wherein $Q^1$ optionally bears 1 or 2 substituents, which may be the same or different selected from hydroxy, (1-4C) alkyl and (1-4C)alkoxy,
and wherein $Q^1$ optionally bears an oxo substituent;

(x) $Q^1$ is pyrrolidin-2-yl,
and wherein the group of the formula ZC(O) is attached at the 1-position in $Q^1$,
and wherein $Q^1$ optionally bears an oxo substituent;

(y) $Q^1$ is pyrrolidin-3-yl,
and wherein the group of the formula ZC(O) is attached at the 1-position in $Q^1$,
and wherein $Q^1$ optionally bears an oxo substituent;

(z) $Q^1$—$X^1$ is selected from pyrrolidin-2-ylmethyl and pyrrolidin-3-ylmethyl,
and wherein $Q^1$ optionally bears one or more (for example 1, 2 or 3) substituents, which may be the same or different selected from fluoro, chloro, hydroxy, carbamoyl, methyl, methoxy, N-methylcarbamoyl and N,N-dimethylcarbamoyl,
and wherein any heterocyclyl group within $Q^1$ optionally bears an oxo substituent,
and wherein the group of the formula ZC(O) is attached at the 1-position in $Q^1$;

(aa) $Q^1$—$X^1$ is selected from pyrrolidin-2-ylmethyl and pyrrolidin-2-ylmethyl,
and wherein $Q^1$ optionally bears one or more (for example 1, 2 or 3) substituents, which may be the same or different selected from fluoro, chloro, hydroxy, methyl and methoxy,
and wherein $Q^1$ optionally bears an oxo substituent,
and wherein the group of the formula ZC(O) is attached at the 1-position in $Q^1$;

(bb) $Q^1$—$X^1$ is pyrrolidin-2-ylmethyl
and wherein $Q^1$ optionally bears one or more (for example 1, 2 or 3) substituents, which may be the same or different selected from hydroxy, (1-4C)alkyl and (1-4C)alkoxy (particularly hydroxy, methyl and methoxy),
and wherein $Q^1$ optionally bears an oxo substituent,
and wherein the group of the formula ZC(O) is attached at the 1-position in $Q^1$;

(cc) $Q^1$—$X^1$ is pyrrolidin-2-ylmethyl
and wherein $Q^1$ optionally bears one or more (for example 1 or 2, particularly 1) substituents, which may be the same or different selected from hydroxy, methyl, ethyl, methoxy, ethoxy, hydroxymethyl, methoxymethyl, 2-hydroxyethoxy and 2-methoxyethoxy (particularly $Q^1$ optionally bears one of the hereinabove defined substituents at the 4-position on the pyrrolidinyl ring, more particularly $Q^1$ optionally bears a substituent at the 4-position selected from hydroxy, methyl and methoxy),
and wherein the group of the formula ZC(O) is attached at the 1-position in $Q^1$;

(dd) $Q^1$—$X^1$ is (2R)-pyrrolidin-2-ylmethyl,
and wherein $Q^1$ optionally bears one or more (for example 1, 2 or 3) substituents, which may be the same or different selected from halogeno, hydroxy, (1-4C)alkyl and (1-4C) alkoxy (particularly hydroxy, methyl and methoxy),
and wherein $Q^1$ optionally bears an oxo substituent,
and wherein the group of the formula ZC(O) is attached at the 1-position in $Q^1$;

(ee) $Q^1$—$X^1$ is (2S)-pyrrolidin-2-ylmethyl,
and wherein $Q^1$ optionally bears one or more (for example 1, 2 or 3) substituents, which may be the same or different selected from halogeno, hydroxy, (1-4C)alkyl and (1-4C) alkoxy (particularly hydroxy, methyl and methoxy),
and wherein $Q^1$ optionally bears an oxo substituent,
and wherein the group of the formula ZC(O) is attached at the 1-position in $Q^1$;

(ff) $Q^1$—$X^1$ is (2R)-pyrrolidin-2-ylmethyl,
and wherein the pyrrolidinyl group optionally bears one or two substituents, which may be the same or different selected from fluoro, chloro, hydroxy, carbamoyl, (1-3C)alkyl (particularly methyl), (1-3C)alkoxy (particularly methoxy), N-methylcarbamoyl and N,N-dimethylcarbamoyl,
and wherein the pyrrolidinyl group optionally bears an oxo substituent,
and wherein the group of the formula ZC(O) is attached at the 1-position of the pyrrolidinyl group;

(gg) $Q^1$—$X^1$ is (2S)-pyrrolidin-2-ylmethyl,
and wherein the pyrrolidinyl group optionally bears one or two substituents, which may be the same or different selected from fluoro, chloro, hydroxy, carbamoyl, (1-3C)alkyl (particularly methyl), (1-3C)alkoxy (particularly methoxy), N-methylcarbamoyl and N,N-dimethylcarbamoyl,
and wherein the pyrrolidinyl group optionally bears an oxo substituent,
and wherein the group of the formula ZC(O) is attached at the 1-position of the pyrrolidinyl group;

(hh) $Q^1$—$X^1$ is selected from (3S)-pyrrolidin-3-ylmethyl and (3R)-pyrrolidin-3-ylmethyl,
and wherein the pyrrolidinyl group optionally bears one or two substituents, which may be the same or different selected from fluoro, chloro, hydroxy, carbamoyl, (1-3C)alkyl (particularly methyl), (1-3C)alkoxy (particularly methoxy), N-methylcarbamoyl and N,N-dimethylcarbamoyl,
and wherein the pyrrolidinyl group optionally bears an oxo substituent,
and wherein the group of the formula ZC(O) is attached at the 1-position of the pyrrolidinyl group;

(ii) Z is selected from halogeno-(1-2C)alkyl, hydroxy-(1-2C) alkyl, (1-4C)alkoxy-(1-2C)alkyl, amino-(1-2C)alkyl, (1-4C) alkylamino-(1-2C)alkyl and di-[(1-4C)alkyl]amino-(1-2C) alkyl,
or Z is $Q^2$, wherein $Q^2$ is heterocyclyl or heterocyclyl-(1-2C)alkyl, and wherein the heterocyclyl in $Q^2$ contains at least 1 nitrogen heteroatom, and optionally 1 or 2 further heteroatoms selected from oxygen, nitrogen and sulfur,
and wherein $Q^2$ is linked to the (1-2C)alkyl or C(O) group by a ring nitrogen,
and wherein any $CH_2$ or $CH_3$ group within a Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carbamoyl, formyl, mercapto, (2-6C) alkenyl, (2-6C)alkyl, (1-6C)alkoxy, (1-6C)alkylthio, (1-6C) alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino and N-(1-6C)alkyl-(2-6C)alkanoylamino,
and wherein any heterocyclyl group within Z optionally bears one or more (for example 1, 2 or 3) substituents, which may be the same or different selected from halogeno, trifluoromethyl, cyano, nitro, hydroxy, amino, carbamoyl, formyl, (1-6C)alkyl, (2-6C)alkenyl, (2-6C)alkynyl, (1-6C)alkoxy, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, N-(1-6C)alkylsulfamoyl and N,N-di-[(1-6C)alkyl]sulfamoyl, or from a group of the formula:

—$X^2$—$R^4$ wherein $X^2$ is a direct bond or is selected from O, CO and N($R^5$), wherein $R^5$ is hydrogen or (1-6C)alkyl, and $R^4$ is halogeno-(1-6C)alkyl, hydroxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl and N,N-di-[(1-6C)alkyl]carbamoyl-(1-6C)alkyl, and wherein any heterocyclyl group within Z optionally bears 1 or 2 oxo substituents;

(jj) Z is selected from halogeno-(1-2C)alkyl, hydroxy-(1-2C)alkyl, (1-4C)alkoxy-(1-2C)alkyl, amino-(1-2C)alkyl, (1-4C)alkylamino-(1-2C)alkyl and di-[(1-4C)alkyl]amino-(1-2C)alkyl, or Z is $Q^2$, wherein $Q^2$ is heterocyclyl or heterocyclyl-(1-2C)alkyl, and wherein the heterocyclyl in $Q^2$ is a fully saturated 4, 5, 6 or 7 membered monocyclic heterocyclyl group which contains at least 1 nitrogen heteroatom, and optionally 1 or 2 further heteroatoms selected from oxygen, nitrogen and sulfur, and wherein $Q^2$ is linked to the (1-2C)alkyl or C(O) group by a ring nitrogen, and wherein any $CH_2$ or $CH_3$ group within a Z group, other than a $CH_2$ group within a heterocyclyl ring, optionally bears on each said $CH_2$ or $CH_3$ group one or more (1-4C)alkyl substituents or a substituent selected from cyano, carbamoyl, formyl, (2-6C)alkenyl, (2-6C)alkynyl, N-(1-6C)alkylcarbamoyl, N,N-di-[(1-6C)alkyl]carbamoyl and (2-6C)alkanoyl, and wherein any $CH_2$ which is attached to 2 carbon atoms or a $CH_3$ group which is attached to a carbon atom within a Z group, other than a $CH_2$ group within a heterocyclyl ring, optionally bears on each said $CH_2$ or $CH_3$ group one or more halogeno substituents or a substituent selected from hydroxy, amino, mercapto, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyloxy, (2-6C)alkanoylamino and N-(1-6C)alkyl-(2-6C)alkanoylamino, and wherein any heterocyclyl group within Z optionally bears one or more (for example 1, 2 or 3) substituents, which may be the same or different selected from halogeno, trifluoromethyl, cyano, nitro, hydroxy, amino, carbamoyl, formyl, (1-6C)alkyl, (2-6C)alkenyl, (2-6C)alkynyl, (1-6C)alkoxy, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, N-(1-6C)alkylsulfamoyl and N,N-di-[(1-6C)alkyl]sulfamoyl, or from a group of the formula:

—$X^2$—$R^4$ wherein $X^2$ is a direct bond or is selected from O, CO and N($R^5$), wherein $R^5$ is hydrogen or (1-4C)alkyl, and $R^4$ is halogeno-(1-6C)alkyl, hydroxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl and N,N-di-[(1-6C)alkyl]carbamoyl-(1-6C)alkyl, and wherein any heterocyclyl group within Z optionally bears 1 or 2 oxo substituents;

(kk) Z is selected from hydroxy-(1-2C)alkyl, (1-4C)alkoxy-(1-2C)alkyl, amino-(1-2C)alkyl, (1-4C)alkylamino-(1-2C)alkyl and di-[(1-4C)alkyl]amino-(1-2C)alkyl, or Z is $Q^2$, wherein $Q^2$ is heterocyclyl or heterocyclyl-(1-2C)alkyl, and wherein the heterocyclyl in $Q^2$ is a fully saturated 4, 5, 6 or 7 membered monocyclic heterocyclyl group which contains at least 1 nitrogen heteroatom, and optionally 1 or 2 further heteroatoms selected from oxygen, nitrogen and sulfur, and wherein $Q^2$ is linked to the (1-2C)alkyl or C(O) group by a ring nitrogen, and wherein any $CH_2$ or $CH_3$ group within a Z group, other than a $CH_2$ group within a heterocyclyl ring, optionally bears on each said $CH_2$ or $CH_3$ group one or more (1-4C)alkyl substituents or a substituent selected from cyano, carbamoyl, formyl, (2-6C)alkenyl, (2-6C)alkynyl, N-(1-6C)alkylcarbamoyl, N,N-di-[(1-6C)alkyl]carbamoyl and (2-6C)alkanoyl, and wherein any $CH_2$ which is attached to 2 carbon atoms or a $CH_3$ group which is attached to a carbon atom within a Z group, other than a $CH_2$ group within a heterocyclyl ring, optionally bears on each said $CH_2$ or $CH_3$ group one or more halogeno substituents or a substituent selected from hydroxy, amino, mercapto, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyloxy, (2-6C)alkanoylamino and N-(1-6C)alkyl-(2-6C)alkanoylamino, and wherein any heterocyclyl group within Z optionally bears one or more (for example 1, 2 or 3) substituents, which may be the same or different selected from halogeno, trifluoromethyl, cyano, nitro, hydroxy, amino, carbamoyl, formyl, (1-6C)alkyl, (2-6C)alkenyl, (2-6C)alkynyl, (1-6C)alkoxy, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, N-(1-6C)alkylsulfamoyl and N,N-di-[(1-6C)alkyl]sulfamoyl, or from a group of the formula:

—$X^2$—$R^4$ wherein $X^2$ is a direct bond or is selected from O, CO and N($R^5$), wherein $R^5$ is hydrogen or (1-4C)alkyl, and $R^4$ is halogeno-(1-6C)alkyl, hydroxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl and N,N-di-[(1-6C)alkyl]carbamoyl-(1-6C)alkyl, and wherein any heterocyclyl group within Z optionally bears 1 or 2 oxo substituents;

(ll) Z is selected from halogeno-(1-2C)alkyl, hydroxy-(1-2C)alkyl, (1-4C)alkoxy-(1-2C)alkyl, amino-(1-2C)alkyl, (1-4C)alkylamino-(1-2C)alkyl and di-[(1-4C)alkyl]amino-(1-2C)alkyl, or Z is $Q^2$, wherein $Q^2$ is heterocyclyl or heterocyclyl-(1-2C)alkyl, and wherein the heterocyclyl in $Q^2$ is selected from azetidin-1-yl, pyrrolidin-1-yl, piperidino, piperazin-1-yl, morpholino, homopiperidin-1-yl and homopiperazin-1-yl, and wherein $Q^2$ is linked to the (1-2C)alkyl or C(O) group by a ring nitrogen, and wherein any $CH_2$ or $CH_3$ group within a Z group, other than a $CH_2$ group within a heterocyclyl ring, optionally bears on each said $CH_2$ or $CH_3$ group one or more (1-4C)alkyl substituents or a substituent selected from cyano, carbamoyl, (2-6C)alkenyl, (2-6C)alkynyl, N-(1-6C)alkylcarbamoyl, N,N-di-[(1-6C)alkyl]carbamoyl and (2-6C)alkanoyl, and wherein any $CH_2$ which is attached to 2 carbon atoms or a $CH_3$ group which is attached to a carbon atom within a Z group, other than a $CH_2$ group within a heterocyclyl ring, optionally bears on each said $CH_2$ or $CH_3$ group one or more halogeno substituents or a substituent selected from hydroxy, amino, (1-6C)alkoxy, (1-6C)alkylsulfonyl, (1-6C)alkylamino and di-[(1-6C)alkyl]amino, and wherein any heterocyclyl group within Z optionally bears one or more (for example 1, 2 or 3) substituents, which may be the same or different selected from halogeno, trifluoromethyl, cyano, hydroxy, amino, carbamoyl, (1-6C)alkyl, (1-6C)alkoxy, (1-6C)alkylsulfonyl, (1-6C)alkylamino, di-[(1-6C)alkyl]amino, N-(1-6C)alkylcarbamoyl, N,N-di-[(1-6C)alkyl]carbamoyl and (2-6C)alkanoyl, or from a group of the formula:

$$-X^2-R^4$$

wherein $X^2$ is a direct bond or is selected from O, CO and $N(R^5)$, wherein $R^5$ is hydrogen or (1-4C)alkyl, and $R^4$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl, N,N-di-[(1-4C)alkyl]amino-(1-4C)alkyl, carbamoyl-(1-4C)alkyl, N-(1-4C)alkylcarbamoyl-(1-4C)alkyl and N,N-di-[(1-4C)alkyl]carbamoyl-(1-4C)alkyl, and wherein any heterocyclyl group within Z optionally bears 1 or 2 oxo substituents;

(mm) Z is selected from halogeno-(1-2C)alkyl, hydroxy-(1-2C)alkyl, (1-4C)alkoxy-(1-2C)alkyl, amino-(1-2C)alkyl, (1-4C)alkylamino-(1-2C)alkyl and di-[(1-4C)alkyl]amino-(1-2C)alkyl, or Z is $Q^2$, wherein $Q^2$ is heterocyclyl or heterocyclyl-(1-2C)alkyl, and wherein the heterocyclyl in $Q^2$ is selected from pyrrolidin-1-yl, piperidino, piperazin-1-yl, morpholino, homopiperidin-1-yl and homopiperazin-1-yl and wherein $Q^2$ is linked to the (1-2C)alkyl or C(O) group by a ring nitrogen, and wherein any $CH_2$ or $CH_3$ group within a Z group, other than a $CH_2$ group within a heterocyclyl ring, optionally bears on each said $CH_2$ or $CH_3$ group a substituent selected from (2-6C)alkenyl and (2-6C)alkynyl, and wherein any $CH_2$ which is attached to 2 carbon atoms or a $CH_3$ group which is attached to a carbon atom within a Z group, other than a $CH_2$ group within a heterocyclyl ring, optionally bears on each said $CH_2$ or $CH_3$ group one or more halogeno substituents or a substituent selected from hydroxy, amino, (1-4C)alkoxy, (1-4C)alkylamino and di-[(1-4C)alkyl]amino, and wherein any heterocyclyl group within Z optionally bears one or more (for example 1, 2 or 3) substituents, which may be the same or different selected from fluoro, chloro, cyano, hydroxy, amino, carbamoyl, (1-4C)alkyl, (1-4C)alkoxy, (1-4C)alkylamino, di-[(1-4C)alkyl]amino, N-(1-4C)alkylcarbamoyl, N,N-di-[(1-4C)alkyl]carbamoyl and (2-6C)alkanoyl, or from a group of the formula:

$$-X^2-R^4$$

wherein $X^2$ is a direct bond or is selected from O, CO and $N(R^5)$, wherein $R^5$ is hydrogen or (1-4C)alkyl, and $R^4$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within Z optionally bears an oxo substituent;

(nn) Z is selected from hydroxy-(1-2C)alkyl, (1-4C)alkoxy-(1-2C)alkyl, amino-(1-2C)alkyl, (1-4C)alkylamino-(1-2C)alkyl and di-[(1-4C)alkyl]amino-(1-2C)alkyl, or Z is $Q^2$, wherein $Q^2$ is heterocyclyl or heterocyclyl-(1-2C)alkyl, and wherein the heterocyclyl in $Q^2$ is selected from pyrrolidin-1-yl, piperidino, piperazin-1-yl, morpholino, homopiperidin-1-yl and homopiperazin-1-yl and wherein $Q^2$ is linked to the (1-2C)alkyl or C(O) group by a ring nitrogen, and wherein any $CH_2$ or $CH_3$ group within a Z group, other than a $CH_2$ group within a heterocyclyl ring, optionally bears on each said $CH_2$ or $CH_3$ group a substituent selected from (2-6C)alkenyl and (2-6C)alkynyl, and wherein any $CH_2$ which is attached to 2 carbon atoms or a $CH_3$ group which is attached to a carbon atom within a Z group, other than a $CH_2$ group within a heterocyclyl ring, optionally bears on each said $CH_2$ or $CH_3$ group one or more halogeno substituents or a substituent selected from hydroxy, amino, (1-4C)alkoxy, (1-4C)alkylamino and di-[(1-4C)alkyl]amino, and wherein any heterocyclyl group within Z optionally bears one or more (for example 1, 2 or 3) substituents, which may be the same or different selected from fluoro, chloro, cyano, hydroxy, amino, carbamoyl, (1-4C)alkyl, (1-4C)alkoxy, (1-4C)alkylamino, di-[(1-4C)alkyl]amino, N-(1-4C)alkylcarbamoyl, N,N-di-[(1-4C)alkyl]carbamoyl and (2-6C)alkanoyl, or from a group of the formula:

$$-X^2-R^4$$

wherein $X^2$ is a direct bond or is selected from O, CO and $N(R^5)$, wherein $R^5$ is hydrogen or (1-4C)alkyl, and $R^4$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within Z optionally bears an oxo substituent;

(oo) Z is selected from (1-2C)alkyl, hydroxy-(1-2C)alkyl, amino-(1-2C)alkyl, (1-4C)alkylamino-(1-2C)alkyl and di-[(1-4C)alkyl]amino-(1-2C)alkyl, or Z is $Q^2$, wherein $Q^2$ is heterocyclyl-(1-2C)alkyl, and wherein the heterocyclyl in $Q^2$ is selected from pyrrolidin-1-yl, piperidino and piperazin-1-yl (particularly pyrrolidin-1-yl), and wherein $Q^2$ is linked to the (1-2C)alkyl group by a ring nitrogen, and wherein any heterocyclyl group within Z optionally bears one or more (for example 1, 2 or 3) substituents, which may be the same or different selected from fluoro, chloro, hydroxy, (1-3C)alkyl, (1-3C)alkoxy, or from a group of the formula:

$$-X^2-R^4$$

wherein $X^2$ is a direct bond or is O, and $R^4$ is halogeno-(1-3C)alkyl, hydroxy-(1-3C)alkyl or (1-3C)alkoxy-(1-3C)alkyl, and wherein any heterocyclyl group within Z optionally bears an oxo substituent;

(pp) Z is selected from fluoromethyl, hydroxymethyl, (1-4C)alkoxy-methyl, aminomethyl, (1-4C)alkylaminomethyl, di-[(1-4C)alkyl]aminomethyl, pyrrolidin-1-ylmethyl, piperidinomethyl, piperazin-1-ylmethyl, morpholinomethyl, homopiperidin-1-ylmethyl and homopiperazin-1-ylmethyl and wherein any CH$_2$ or CH$_3$ group within a Z group, other than a CH$_2$ group within a heterocyclyl ring, optionally bears on each said CH$_2$ or CH$_3$ group a substituent selected from vinyl and ethynyl, and wherein any CH$_2$ which is attached to 2 carbon atoms or a CH$_3$ group which is attached to a carbon atom within a Z group, other than a CH$_2$ group within a heterocyclyl ring, optionally bears on each said CH$_2$ or CH$_3$ group one or more halogeno substituents or a substituent selected from hydroxy, amino, (1-4C)alkoxy, (1-4C)alkylamino and di-[(1-4C)alkyl]amino, and wherein any heterocyclyl group within Z optionally bears one or more (for example 1, 2 or 3) substituents, which may be the same or different selected from fluoro, chloro, cyano, hydroxy, amino, carbamoyl, (1-4C)alkyl, (1-4C)alkoxy, (1-4C)alkylamino, di-[(1-4C)alkyl]amino, N-(1-4C)alkylcarbamoyl, N,N-di-[(1-4C)alkyl]carbamoyl and (2-6C)alkanoyl, or from a group of the formula:

—X$^2$—R$^4$ wherein X$^2$ is a direct bond or is selected from O, CO and N(R$^5$), wherein R$^5$ is hydrogen or (1-4C)alkyl, and R$^4$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl, and wherein any heterocyclyl group within Z optionally bears an oxo substituent;

(qq) Z is selected from hydroxymethyl, (1-4C)alkoxy-methyl, aminomethyl, (1-4C)alkylaminomethyl, N-alkylaminomethyl, N-(2-propynyl)aminomethyl, di-[(1-4C)alkyl]aminomethyl, N-allyl-N-[(1-4C)alkyl]aminomethyl, N-(2-propynyl)-N-[(1-4C)alkyl]aminomethyl, pyrrolidin-1-ylmethyl, piperidinomethyl, piperazin-1-ylmethyl, morpholinomethyl, homopiperidin-1-ylmethyl and homopiperazin-1-ylmethyl and wherein any CH$_2$ which is attached to 2 carbon atoms or a CH$_3$ group which is attached to a carbon atom within a Z group, other than a CH$_2$ group within a heterocyclyl ring, optionally bears on each said CH$_2$ or CH$_3$ group one or more substituents selected from fluoro and chloro, or a substituent selected from hydroxy and (1-4C)alkoxy, and wherein any heterocyclyl group within Z optionally bears one or more (for example 1, 2 or 3) substituents, which may be the same or different selected from fluoro, chloro, cyano, hydroxy, amino, carbamoyl, (1-4C)alkyl, (1-4C)alkoxy, (1-4C)alkylamino, di-[(1-4C)alkyl]amino, N-(1-4C)alkylcarbamoyl, N,N-di-[(1-4C)alkyl]carbamoyl, acetyl, propionyl, 2-fluoroethyl, 2-hydroxyethyl, 2-methoxyethyl, cyanomethyl, hydroxyacetyl, aminoacetyl, methylaminoacetyl, ethylaminoacetyl, dimethylaminoacetyl, N-methyl-N-ethylaminoacetyl and fluoroacetyl, and wherein any heterocyclyl group within Z optionally bears an oxo substituent;

(rr) Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)alkyl]-N-[(1-4C)alkyl]aminomethyl, pyrrolidin-1-ylmethyl, piperidinomethyl, piperazin-1-ylmethyl, morpholinomethyl, homopiperidin-1-ylmethyl and homopiperazin-1-ylmethyl, and wherein any heterocyclyl group within Z optionally bears one or more (for example 1, 2 or 3) substituents, which may be the same or different selected from fluoro, chloro, cyano, hydroxy, amino, (1-4C)alkyl, (1-4C)alkoxy, (1-4C)alkylamino and di-[(1-4C)alkyl]amino, and wherein any heterocyclyl group within Z optionally bears an oxo substituent;

(ss) Z is selected from hydroxymethyl, methoxymethyl, ethoxymethyl, aminomethyl, methylaminomethyl, ethylaminomethyl, N-(2-hydroxyethyl)aminomethyl, N-(2-methoxyethyl)aminomethyl, dimethylaminomethyl, N-methyl-N-ethylaminomethyl, di-ethylaminomethyl, N-(2-hydroxyethyl)-N-methylaminomethyl, N-(2-hydroxyethyl)-N-ethylaminomethyl, N,N-di-(2-hydroxyethyl)aminomethyl, N-(2-methoxyethyl)-N-methylaminomethyl, N-(2-methoxyethyl)-N-ethylaminomethyl, pyrrolidin-1-ylmethyl, piperidinomethyl, piperazin-1-ylmethyl and morpholinomethyl, and wherein any heterocyclyl group within Z optionally bears 1 or 2 substituents, which may be the same or different, selected from fluoro, chloro, hydroxy, (1-4C)alkyl and (1-4C)alkoxy;

(tt) Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl and N-[methoxy-(2-4C)alkyl]-N-[(1-4C)alkyl]aminomethyl;

(uu) Z is selected from pyrrolidin-1-ylmethyl, piperidinomethyl, piperazin-1-ylmethyl, morpholinomethyl, homopiperidin-1-ylmethyl, homopiperazin-1-ylmethyl, 2-pyrrolidin-1-ylethyl, 2-piperidinoethyl, 2-piperazin-1-ylethyl, 2-morpholinoethyl, 2-homopiperidin-1-ylethyl and 2-homopiperazin-1-ylethyl (particularly Z is selected from pyrrolidin-1-ylmethyl, piperidinomethyl, piperazin-1-ylmethyl and morpholinomethyl, and wherein the heterocyclyl group within Z optionally bears one or more (for example 1, 2 or 3) substituents, which may be the same or different selected from fluoro, chloro, cyano, hydroxy, amino, carbamoyl, (1-4C)alkyl, (1-4C)alkoxy, (1-4C)alkylamino, di-[(1-4C)alkyl]amino, N-(1-4C)alkylcarbamoyl, N,N-di-[(1-4C)alkyl]carbamoyl, acetyl, propionyl, 2-fluoroethyl, 2-hydroxyethyl, 2-methoxyethyl, cyanomethyl, hydroxyacetyl, aminoacetyl, methylaminoacetyl, ethylaminoacetyl, dimethylaminoacetyl, N-methyl-N-ethylaminoacetyl and fluoroacetyl, (vv) Z is selected from methyl, hydroxymethyl, (1-3C)alkoxymethyl, aminomethyl, (1-3C)alkylaminomethyl, N-di-[(1-3C)alkyl]aminomethyl and pyrrolidin-1-ylmethyl, and wherein any heterocyclyl group within Z optionally bears one or more (for example 1, 2 or 3) substituents, which may be the same or different selected from fluoro, chloro, hydroxy, (1-3C)alkyl and (1-3C)alkoxy;

(ww) Q$^1$—X$^1$ is selected from (2R)-pyrrolidin-2-ylmethyl and (2S)-pyrrolidin-2-ylmethyl, and wherein the group of the formula ZC(O) is attached at the I-position of the pyrrolidinyl group, Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)alkyl]-N-[(1-4C)alkyl]aminomethyl, pyrrolidin-1-ylmethyl, piperidinomethyl, piperazin-1-ylmethyl, morpholinomethyl, homopiperidin-1-ylmethyl and homopiperazin-1-ylmethyl, and wherein any heterocyclyl group within Z optionally bears one or more (for example 1, 2 or 3) substituents, which may be the same or different selected from fluoro, chloro, hydroxy, (1-4C)alkyl and (1-4C)alkoxy, and wherein any heterocyclyl group within Z optionally bears an oxo substituent;

(xx) $Q^1$—$X^1$ is selected from (3R)-pyrrolidin-3-ylmethyl and (3S)-pyrrolidin-3-ylmethyl, and wherein the group of the formula ZC(O) is attached at the 1-position of the pyrrolidinyl group, Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)alkyl]-N-[(1-4C)alkyl]aminomethyl, pyrrolidin-1-ylmethyl, piperidinomethyl, piperazin-1-ylmethyl, morpholinomethyl, homopiperidin-1-ylmethyl and homopiperazin-1-ylmethyl, and wherein any heterocyclyl group within Z optionally bears one or more (for example 1, 2 or 3) substituents, which may be the same or different selected from fluoro, chloro, hydroxy, (1-4C)alkyl and (1-4C)alkoxy, and wherein any heterocyclyl group within Z optionally bears an oxo substituent;

(yy) $Q^1$—$X^1$ is selected from (2R)-pyrrolidin-2-ylmethyl and (2S)-pyrrolidin-2-ylmethyl, and wherein the group of the formula ZC(O) is attached at the 1-position of the pyrrolidinyl group, Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)alkyl]-N-[(1-4C)alkyl]aminomethyl, pyrrolidin-1-ylmethyl, piperidinomethyl, piperazin-1-ylmethyl, morpholinomethyl, homopiperidin-1-ylmethyl and homopiperazin-1-ylmethyl, and wherein any heterocyclyl group within Z optionally bears one or more (for example 1, 2 or 3) substituents, which may be the same or different selected from fluoro, chloro, hydroxy, (1-4C)alkyl and (1-4C)alkoxy, and wherein any heterocyclyl group within Z optionally bears an oxo substituent;

(zz) $Q^1$—$X^1$ is selected from (2R)-pyrrolidin-2-ylmethyl and (2S)-pyrrolidin-2-ylmethyl particularly $Q^1$—$X^1$ is (2R)-pyrrolidin-2-ylmethyl), and wherein the group of the formula ZC(O) is attached at the 1-position of the pyrrolidin-2-yl group, Z is selected from methyl, hydroxymethyl, aminomethyl, (1-2C)alkylaminomethyl, di-[(1-2C)alkyl]aminomethyl and pyrrolidin-1-ylmethyl, and wherein any heterocyclyl group within Z or $Q^1$ optionally bears one or more (for example 1, 2 or 3) substituents, which may be the same or different selected from hydroxy, (1-3C)alkyl and (1-3C)alkoxy, and wherein any heterocyclyl group within Z optionally bears an oxo substituent;

(aaa) $Q^1$—$X^1$ is selected from (2R)-pyrrolidin-2-ylmethyl and (2S)-pyrrolidin-2-ylmethyl (particularly $Q^1$—$X^1$ is (2R)-pyrrolidin-2-ylmethyl), and wherein the group of the formula ZC(O) is attached at the 1-position of the pyrrolidin-2-yl group, Z is selected from hydroxymethyl, aminomethyl, (1-2C)alkylaminomethyl, di-[(1-2C)alkyl]aminomethyl and pyrrolidin-1-ylmethyl, and wherein any heterocyclyl group within Z or $Q^1$ optionally bears one or more (for example 1, 2 or 3) substituents, which may be the same or different selected from hydroxy, (1-3C)alkyl and (1-3C)alkoxy;

(bbb) $Q^1$—$X^1$ is selected from (2R)-pyrrolidin-2-ylmethyl and (2S)-pyrrolidin-2-ylmethyl (particularly $Q^1$—$X^1$ is (2R)-pyrrolidin-2-ylmethyl), and wherein the group of the formula ZC(O) is attached at the 1-position of the pyrrolidin-2-yl group, Z is methyl, and wherein $Q^1$ optionally bears one or more (for example 1, 2 or 3) substituents, which may be the same or different selected from hydroxy, (1-3C)alkyl and (1-3C)alkoxy;

(ccc) Y is selected from halogeno, cyano, (1-6C)alkyl, (1-6C)alkoxy and (2-6C)alkynyl;

(ddd) Y is selected from fluoro, chloro, bromo, iodo, cyano, methyl, ethyl, isopropyl, methoxy, ethoxy, vinyl, alkyl, ethynyl, 1-propynyl and 2-propynyl;

(eee) Y is selected from fluoro, chloro, bromo, methyl and ethynyl;

(fff) Y is halogeno (particularly fluoro, chloro or bromo);

(ggg) Y is methyl;

(hhh) Y is ethynyl;

(iii) each $R^2$, which may be the same or different, is selected from halogeno, cyano, nitro, hydroxy, amino, carboxy, carbamoyl, trifluoromethyl, (1-6C)alkyl, (2-8C)alkenyl, (2-8C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl and N,N-di-[(1-6C)alkyl]carbamoyl;

(jjj) each $R^2$, which may be the same or different, is selected from fluoro, chloro, bromo, iodo, cyano, hydroxy, amino, carbamoyl, trifluoromethyl, (1-4C)alkyl, (2-4C)alkenyl, (2-4C)alkynyl, (1-4C)alkoxy, (1-4C)alkylthio, (1-4C)alkylsulfinyl, (1-4C)alkylsulfonyl, (1-4C)alkylamino, di-[(1-4C)alkyl]amino, (1-4C)alkoxycarbonyl, N-(1-4C)alkylcarbamoyl, N,N-di-[(1-4C)alkyl]carbamoyl;

(kkk) each $R^2$, which may be the same or different, is selected from fluoro, chloro, bromo, iodo, cyano, hydroxy, trifluoromethyl, (1-4C)alkyl, (2-4C)alkenyl, (2-4C)alkynyl and (1-4C)alkoxy;

(lll) each $R^2$, which may be the same or different, is selected from fluoro, chloro, bromo, iodo, cyano, carbamoyl, hydroxy, trifluoromethyl, methyl, ethyl, isopropyl, methoxy, ethoxy, vinyl, alkyl, ethynyl, 1-propynyl, 2-propynyl, N-methylcarbamoyl, N-ethylcarbamoyl and N,N-dimethylcarbamoyl;

(mmm) each $R^2$, which may be the same or different, is selected from fluoro, chloro, bromo, iodo, cyano, hydroxy, trifluoromethyl, methyl, ethyl, isopropyl, methoxy, ethoxy, vinyl, alkyl, ethynyl, 1-propynyl, and 2-propynyl;

(nnn) each $R^2$, which may be the same or different, is selected from fluoro, chloro, bromo, cyano, hydroxy, trifluoromethyl, methyl, ethyl, methoxy, ethoxy and ethynyl;

(ooo) each $R^2$, which may be the same or different, is selected from halogeno (particularly fluoro, chloro and bromo);

(ppp) a is 0, 1, 2 or 3, each $R^2$ is as defined in any of (iii) to (ooo) above and at least 1 $R^2$ is in an ortho position to the NH group;

(qqq) a is 0, 1 or 2, each $R^2$ is as defined in any of (iii) to (ooo) above and wherein $R^2$ is not in an ortho position to the NH group;

(rrr) a is 1, $R^2$ is in an ortho position to the NH group and is selected from halogeno (particularly fluoro, chloro or bromo);

(sss) a is 1, $R^2$ is in the para position to the NH group and is selected from halogeno (particularly fluoro, chloro or bromo);

(ttt) a is 1, $R^2$ is in the 2-position on the anilino group and is selected from halogeno (particularly fluoro, chloro or bromo, more particularly fluoro), and Y is halogeno (particularly fluoro, chloro or bromo);

(uuu) a is 1, $R^2$ is in the para to the NH group and is selected from halogeno (particularly fluoro, chloro or bromo), and Y is halogeno (particularly fluoro, chloro or bromo);

(vvv) a is 0 and Y is as defined in any of (ccc) to (hhh);

(www) Y is selected from fluoro, chloro, bromo, iodo, methyl, ethyl, isopropyl, methoxy, ethoxy, vinyl, alkyl, ethynyl, 1-propynyl and 2-propynyl, a is 0, 1, 2 or 3, and each $R^2$, which may be the same or different, is selected from fluoro, chloro, bromo, iodo, cyano, trifluoromethyl, methyl, ethyl, isopropyl, methoxy, ethoxy, vinyl, alkyl, ethynyl, 1-propynyl and 2-propynyl;

(xxx) the aniline at the 4-position in the quinazoline ring in formula I is selected from 3-chloro-4-fluoroanilino, 3-chloro-2-fluoroanilino, 2-fluoro-5-chloroanilino, 3-bromoanilino, 3-methylanilino and 3-ethynylanilino;

(yyy) the aniline at the 4-position in the quinazoline ring in formula I is 3-chloro-2-fluoroanilino; and (zzz) the aniline at the 4-position in the quinazoline ring in formula I is 3-chloro-4-fluoroanilino.

A particular embodiment of the present invention is a quinazoline derivative of the formula I wherein:

m is 1 and $R^1$ is located at the 7-position and is selected from (1-4C)alkoxy, hydroxy-(1-4C)alkoxy and (1-4C)alkoxy (1-4C)alkoxy;

$X^1$ is $C(R^3)_2$, wherein each $R^3$, which may be the same or different, is selected from hydrogen and (1-4C)alkyl;

$Q^1$ is selected from pyrrolidin-2-yl and pyrrolidin-3-yl, and wherein the group of the formula ZC(O) is attached at the 1-position in $Q^1$, and wherein $Q^1$ optionally bears one or more (for example 1, 2 or 3) substituents, which may be the same or different selected from fluoro, chloro, hydroxy, carbamoyl, (1-4C)alkyl, (1-4C)alkoxy, N-(1-4C)alkylcarbamoyl and N,N-di-[(1-4C)alkyl]carbamoyl, and wherein $Q^1$ optionally bears an oxo substituent;

Z is selected from halogeno-(1-2C)alkyl, hydroxy-(1-2C)alkyl, (1-4C)alkoxy-(1-2C)alkyl, amino-(1-2C)alkyl, (1-4C)alkylamino-(1-2C)alkyl and di-[(1-4C)alkyl]amino-(1-2C)alkyl, or Z is $Q^2$, wherein $Q^2$ is heterocyclyl or heterocyclyl-(1-2C)alkyl, and wherein the heterocyclyl in $Q^2$ is selected from azetidin-1-yl, pyrrolidin-1-yl, piperidino, piperazin-1-yl, morpholino, homopiperidin-1-yl and homopiperazin-1-yl, and wherein $Q^2$ is linked to the (1-2C)alkyl or C(O) group by a ring nitrogen, and wherein any $CH_2$ or $CH_3$ group within a Z group, other than a $CH_2$ group within a heterocyclyl ring, optionally bears on each said $CH_2$ or $CH_3$ group one or more (1-4C)alkyl substituents or a substituent selected from cyano, carbamoyl, (2-6C)alkenyl, (2-6C)alkynyl, N-(1-6C)alkylcarbamoyl, N,N-di-[(1-6C)alkyl]carbamoyl and (2-6C)alkanoyl, and wherein any $CH_2$ which is attached to 2 carbon atoms or a $CH_3$ group which is attached to a carbon atom within a Z group, other than a $CH_2$ group within a heterocyclyl ring, optionally bears on each said $CH_2$ or $CH_3$ group one or more halogeno substituents or a substituent selected from hydroxy, amino, (1-6C)alkoxy, (1-6C)alkylsulfonyl, (1-6C)alkylamino and di-[(1-6C)alkyl]amino, and wherein any heterocyclyl group within Z optionally bears one or more (for example 1, 2 or 3) substituents, which may be the same or different selected from halogeno, trifluoromethyl, cyano, hydroxy, amino, carbamoyl, (1-6C)alkyl, (1-6C)alkoxy, (1-6C)alkylsulfonyl, (1-6C)alkylamino, di-[(1-6C)alkyl]amino, N-(1-6C)alkylcarbamoyl, N,N-di-[(1-6C)alkyl]carbamoyl and (2-6C)alkanoyl, or from a group of the formula:

$$-X^2-R^4$$

wherein $X^2$ is a direct bond or is selected from O, CO and $N(R^5)$, wherein $R^5$ is hydrogen or (1-4C)alkyl, and $R^4$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl, N,N-di-[(1-4C)alkyl]amino-(1-4C)alkyl, carbamoyl-(1-4C)alkyl, N-(1-4C)alkylcarbamoyl-(1-4C)alkyl and N,N-di-[(1-4C)alkyl]carbamoyl-(1-4C)alkyl, and wherein any heterocyclyl group within Z optionally bears 1 or 2 oxo substituents;

Y is selected from halogeno, cyano, trifluoromethyl, (1-6C)alkyl, (1-6C)alkoxy and (2-6C)alkynyl;

each $R^2$, which may be the same or different, is selected from halogeno, cyano, nitro, hydroxy, amino, carboxy, carbamoyl, trifluoromethyl, (1-6C)alkyl, (2-8C)alkenyl, (2-8C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl and N,N-di-[(1-6C)alkyl]carbamoyl; and a is 0, 1 or 2;

or a pharmaceutically acceptable salt thereof.

A further embodiment of the invention is a quinazoline derivative of the formula I wherein:

m is 1 and $R^1$ is located at the 7-position and is selected from (1-4C)alkoxy, hydroxy-(1-4C)alkoxy, methoxy-(1-4C)alkoxy and ethoxy-(1-4C)alkoxy (particularly $R^1$ is (1-4C)alkoxy, more particularly methoxy);

$Q^1$—$X^1$ is selected from pyrrolidin-2-ylmethyl and pyrrolidin-3-ylmethyl, and wherein $Q^1$ optionally bears one or more (for example 1, 2 or 3) substituents, which may be the same or different selected from fluoro, chloro, hydroxy, carbamoyl, (1-3C)alkyl, (1-3C)alkoxy, N-methylcarbamoyl and N,N-dimethylcarbamoyl, and wherein $Q^1$ optionally bears an oxo substituent, and wherein the group of the formula ZC(O) is attached at the 1-position in $Q^1$;

Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)

alkyl]-N-[(1-4C)alkyl]aminomethyl, pyrrolidin-1-ylmethyl, piperidinomethyl, piperazin-1-ylmethyl and morpholinomethyl, and wherein any heterocyclyl group within Z optionally bears one or more (for example 1, 2 or 3) substituents, which may be the same or different selected from fluoro, chloro, cyano, hydroxy, amino, carbamoyl, (1-4C)alkyl, (1-4C)alkoxy, (1-4C)alkylamino, di-[(1-4C)alkyl]amino, N-(1-4C)alkylcarbamoyl, N,N-di-[(1-4C)alkyl]carbamoyl, acetyl, propionyl, 2-fluoroethyl, 2-hydroxyethyl, 2-methoxyethyl, cyanomethyl, hydroxyacetyl, aminoacetyl, methylaminoacetyl, ethylaminoacetyl, dimethylaminoacetyl, N-methyl-N-ethylaminoacetyl and fluoroacetyl, and wherein any heterocyclyl group within Z optionally bears an oxo substituent;

Y is selected from fluoro, chloro, bromo, iodo, cyano, trifluoromethyl, methyl, ethyl, isopropyl, methoxy, ethoxy, vinyl, alkyl, ethynyl, 1-propynyl and 2-propynyl;

each $R^2$, which may be the same or different, is selected from fluoro, chloro, bromo, iodo, cyano, hydroxy, trifluoromethyl, (1-4C)alkyl, (2-4C)alkynyl and (1-4C)alkoxy; and a is 0, 1 or 2 (particularly 0 or 1);

or a pharmaceutically acceptable salt thereof.

A further embodiment of the invention is a quinazoline derivative of the formula I wherein:

m is 1 and $R^1$ is located at the 7-position and is selected from (1-4C)alkoxy, hydroxy-(1-4C)alkoxy, methoxy-(1-4C)alkoxy and ethoxy-(1-4C)alkoxy (particularly $R^1$ is (1-4C)alkoxy, more particularly methoxy);

$Q^1$—$X^1$ is selected from pyrrolidin-2-ylmethyl and pyrrolidin-3-ylmethyl, and wherein $Q^1$ optionally bears one or more (for example 1, 2 or 3) substituents, which may be the same or different selected from hydroxy and (1-3C)alkoxy, and wherein $Q^1$ optionally bears an oxo substituent, and wherein the group of the formula ZC(O) is attached at the 1-position in $Q^1$;

Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)alkyl]-N-[(1-4C)alkyl]aminomethyl, pyrrolidin-1-ylmethyl, piperidinomethyl, piperazin-1-ylmethyl and morpholinomethyl, and wherein any heterocyclyl group within Z optionally bears one or more (for example 1, 2 or 3) substituents, which may be the same or different selected from hydroxy, amino, carbamoyl, (1-4C)alkyl, (1-4C)alkoxy, (1-4C)alkylamino, di-[(1-4C)alkyl]amino, N-(1-4C)alkylcarbamoyl and N,N-di-[(1-4C)alkyl]carbamoyl and wherein any heterocyclyl group within Z optionally bears an oxo substituent;

Y is selected from fluoro, chloro, bromo, cyano, methyl, methoxy and ethynyl;

each $R^2$, which may be the same or different, is selected from fluoro, chloro, bromo, cyano, hydroxy, trifluoromethyl, methyl, ethyl, methoxy, ethoxy and ethynyl; and a is 0, 1 or 2 (particularly 0 or 1);

or a pharmaceutically acceptable salt thereof.

A further embodiment of the invention is a quinazoline derivative of the formula I wherein:

m is 1 and $R^1$ is located at the 7-position and is selected from (1-4C)alkoxy, hydroxy-(1-4C)alkoxy, methoxy-(1-4C)alkoxy and ethoxy-(1-4C)alkoxy (particularly $R^1$ is (1-4C)alkoxy, 2-hydroxyethoxy or 2-methoxyethoxy more particularly $R^1$ is methoxy);

$Q^1$—$X^1$ is pyrrolidin-2-ylmethyl, and wherein $Q^1$ optionally bears one or more (for example 1, 2 or 3) substituents, which may be the same or different selected from hydroxy and (1-3C)alkoxy, and wherein $Q^1$ optionally bears an oxo substituent, and wherein the group of the formula ZC(O) is attached at the 1-position in $Q^1$;

Z is selected from hydroxymethyl, methoxymethyl, aminomethyl, methylaminomethyl, di-methylaminomethyl, pyrrolidin-1-ylmethyl, piperidinomethyl and morpholinomethyl (particularly Z is selected from hydroxymethyl, aminomethyl, methylaminomethyl, di-methylaminomethyl and pyrrolidin-1-ylmethyl), and wherein any heterocyclyl group within Z optionally bears 1 or 2 substituents, which may be the same or different selected from hydroxy, amino, methyl, ethyl, methoxy, methylamino and di-methylamino;

Y is halogeno (particularly fluoro, chloro or bromo);

each $R^2$, which may be the same or different, is selected from halogeno (particularly fluoro, chloro or bromo); and a is 0, 1 or 2 (particularly 0 or 1);

or a pharmaceutically acceptable salt thereof.

A further embodiment of the invention is a quinazoline derivative of the formula I wherein:

m is 1 and $R^1$ is located at the 7-position and is selected from (1-4C)alkoxy, hydroxy-(1-4C)alkoxy, (1-4C)alkoxy-(1-4C)alkoxy (particularly $R^1$ is (1-4C)alkoxy-(1-4C)alkoxy or (1-4C)alkoxy more particularly $R^1$ methoxy, 2-methoxyethoxy or 2-ethoxyethoxy);

$Q^1$—$X^1$ is selected pyrrolidin-2-ylmethyl, and wherein $Q^1$ optionally bears one or more (for example 1, 2 or 3) substituents, which may be the same or different selected from hydroxy, (1-3C)alkyl, (1-3C)alkoxy, hydroxy-(1-3C)alkoxy and (1-3C)alkoxy-(1-3C)alkoxy;

and wherein $Q^1$ optionally bears an oxo substituent, and wherein the group of the formula ZC(O) is attached at the 1-position in $Q^1$;

Z is selected from hydroxymethyl, methoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)alkyl]-N-[(1-4C)alkyl]aminomethyl, pyrrolidin-1-ylmethyl, piperidinomethyl, piperazin-1-ylmethyl and morpholinomethyl, and wherein any heterocyclyl group within Z optionally bears one or more (for example 1, 2 or 3) substituents, which may be the same or different selected from halogeno for example fluoro or chloro), hydroxy, (1-4C)alkyl and (1-4C)alkoxy, and wherein any heterocyclyl group within Z optionally bears an oxo substituent;

Y is selected from fluoro, chloro, bromo, cyano, methyl, methoxy and ethynyl;

each $R^2$, which may be the same or different, is selected from fluoro, chloro, bromo, cyano, hydroxy, trifluoromethyl, methyl, ethyl, methoxy, ethoxy and ethynyl; and a is 0, 1 or 2 (particularly 0 or 1);

or a pharmaceutically acceptable salt thereof.

A further embodiment of the invention is a quinazoline derivative of the formula I wherein:

m is 1 and $R^1$ is located at the 7-position and is selected from (1-4C)alkoxy, 2-hydroxyethoxy and 2-methoxyethoxy (particularly $R^1$ is methoxy);

$Q^1$—$X^1$ is (2R)-pyrrolidin-2-ylmethyl, and wherein the group of the formula ZC(O) is attached at the 1-position of the pyrrolidinyl group, Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)alkyl]-N-[(1-4C)alkyl]aminomethyl, pyrrolidin-1-ylmethyl, piperidinomethyl, piperazin-1-ylmethyl, morpholinomethyl, homopiperidin-1-ylmethyl and homopiperazin-1-ylmethyl, and wherein any heteroocyclyl group within Z optionally bears one or more (for example 1, 2 or 3) substituents, which may be the same or different selected from fluoro, chloro, hydroxy, (1-4C)alkyl and (1-4C)alkoxy, and wherein any heterocyclyl group within Z optionally bears an oxo substituent;

Y is selected from fluoro, chloro, bromo, cyano, methyl, ethyl, isopropyl, methoxy, ethoxy, vinyl, alkyl, ethynyl, 1-propynyl and 2-propynyl (particularly Y is selected from fluoro, chloro and bromo);

each $R^2$, which may be the same or different, is selected from fluoro, chloro, bromo, cyano, hydroxy, trifluoromethyl, (1-4C)alkyl, (2-4C)alkynyl and (1-4C)alkoxy (particularly each $R^2$, which may be the same or different is selected from fluoro, chloro and bromo); and a is 0, 1 or 2 (particularly 0 or 1);

or a pharmaceutically acceptable salt thereof.

A further embodiment of the invention is a quinazoline derivative of the formula I wherein:

m is 1 and $R^1$ is located at the 7-position and is selected from (1-4C)alkoxy, 2-hydroxyethoxy and 2-methoxyethoxy (particularly $R^1$ is methoxy);

$Q^1$—$X^1$ is (2S)-pyrrolidin-2-ylmethyl, and wherein the group of the formula ZC(O) is attached at the 1-position of the pyrrolidinyl group, Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)alkyl]-N-[(1-4C)alkyl]aminomethyl, pyrrolidin-1-ylmethyl, piperidinomethyl, piperazin-1-ylmethyl, morpholinomethyl, homopiperidin-1-ylmethyl and homopiperazin-1-ylmethyl, and wherein any heteroocyclyl group within Z optionally bears one or more (for example 1, 2 or 3) substituents, which may be the same or different selected from fluoro, chloro, hydroxy, (1-4C)alkyl and (1-4C)alkoxy, and wherein any heterocyclyl group within Z optionally bears an oxo substituent;

Y is selected from fluoro, chloro, bromo, cyano, methyl, ethyl, isopropyl, methoxy, ethoxy, vinyl, alkyl, ethynyl, 1-propynyl and 2-propynyl (particularly Y is selected from fluoro, chloro and bromo);

each $R^2$, which may be the same or different, is selected from fluoro, chloro, bromo, cyano, hydroxy, trifluoromethyl, (1-4C)alkyl, (2-4C)alkynyl and (1-4C)alkoxy (particularly each $R^2$, which may be the same or different is selected from fluoro, chloro and bromo); and a is 0, 1 or 2 (particularly 0 or 1);

or a pharmaceutically acceptable salt thereof.

A further embodiment of the invention is a quinazoline derivative of the formula I wherein:

m is 1 and $R^1$ is located at the 7-position and is selected from (1-4C)alkoxy, 2-hydroxyethoxy and 2-methoxyethoxy (particularly $R^1$ is methoxy);

$Q^1$—$X^1$ is selected from (3R)-pyrrolidin-3-ylmethyl and (3S)-pyrrolidin-3-ylmethyl, and wherein the group of the formula ZC(O) is attached at the 1-position of the pyrrolidinyl group, Z is selected from hydroxymethyl, methoxymethyl, ethoxymethyl, aminomethyl, (1-4C)alkylaminomethyl, N-[hydroxy-(2-4C)alkyl]-aminomethyl, N-[methoxy-(2-4C)alkyl]-aminomethyl, di-[(1-4C)alkyl]aminomethyl, N-[hydroxy-(2-4C)alkyl]-N-[(1-4C)alkyl]aminomethyl, N,N-di-[hydroxy-(2-4C)alkyl]-aminomethyl, N-[methoxy-(2-4C)alkyl]-N-[(1-4C)alkyl]aminomethyl, pyrrolidin-1-ylmethyl, piperidinomethyl, piperazin-1-ylmethyl, morpholinomethyl, homopiperidin-1-ylmethyl and homopiperazin-1-ylmethyl, and wherein any heteroocyclyl group within Z optionally bears one or more (for example 1, 2 or 3) substituents, which may be the same or different selected from fluoro, chloro, hydroxy, (1-4C)alkyl and (1-4C)alkoxy, and wherein any heterocyclyl group within Z optionally bears an oxo substituent;

Y is selected from fluoro, chloro, bromo, cyano, methyl, ethyl, isopropyl, methoxy, ethoxy, vinyl, alkyl, ethynyl, 1-propynyl and 2-propynyl (particularly Y is selected from fluoro, chloro and bromo);

each $R^2$, which may be the same or different, is selected from fluoro, chloro, bromo, cyano, hydroxy, trifluoromethyl, (1-4C)alkyl, (2-4C)alkynyl and (1-4C)alkoxy (particularly each $R^2$, which may be the same or different is selected from fluoro, chloro and bromo); and a is 0, 1 or 2 (particularly 0 or 1);

or a pharmaceutically acceptable salt thereof.

A further embodiment of the invention is a quinazoline derivative of the formula I of the formula Ia:

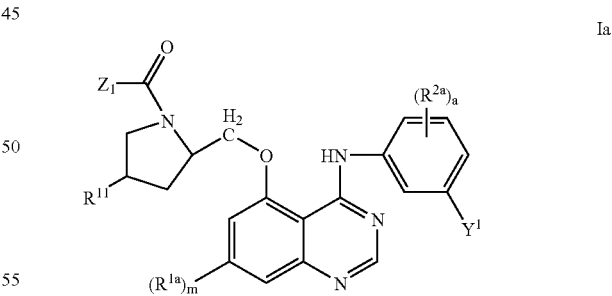

Ia wherein:

m is 0 or m is 1 and $R^{1a}$ is selected from (1-4C)alkoxy, hydroxy-(1-4C)alkoxy and (1-4C)alkoxy(1-4C)alkoxy;

$R^{11}$ is selected from hydrogen, hydroxy, (1-4C)alkyl, (1-4C)alkoxy, hydroxy-(1-4C)alkyl, (1-4C)alkoxy-(1-4C)alkyl, hydroxy-(1-4C)alkoxy and (1-4C)alkoxy-(1-4C)alkoxy;

$Z^1$ is selected from (1-2C)alkyl, hydroxy-(1-2C)alkyl, (1-2C)alkoxy-(1-2C)alkyl, amino-(1-2C)alkyl, (1-4C)alkylamino-(1-2C)alkyl and di-[(1-4C)alkyl]amino-(1-2C)alkyl, or $Z^1$ is $Q^2$, wherein $Q^2$ is pyrrolidinyl-(1-2C)alkyl (particularly pyrrolidin-1-yl-(1-2C)alkyl)), and wherein any pyrrolidinyl group within $Z^1$ optionally bears one or more (for example 1, 2 or 3) substituents, which may be the same or different selected from fluoro, chloro, hydroxy, (1-3C)alkyl, (1-3C)alkoxy, or from a group of the formula:

—$X^2$—$R^4$ wherein $X^2$ is a direct bond or is O, and $R^4$ is halogeno-(1-3C)alkyl, hydroxy-(1-3C)alkoxy-(1-3C)alkyl, and wherein any pyrrolidinyl group within $Z^1$ optionally bears an oxo substituent;

$Y^1$ is selected from fluoro, chloro, bromo, cyano, methyl, ethyl, isopropyl, methoxy, ethoxy, vinyl, alkyl, ethynyl, 1-propynyl and 2-propynyl (particularly $Y^1$ is selected from fluoro, chloro, bromo and ethynyl);

each $R^{2a}$, which may be the same or different, is selected from fluoro, chloro, bromo, cyano, hydroxy, trifluoromethyl, (1-4C)alkyl, (2-4C)alkynyl and (1-4C)alkoxy (particularly each $R^{2a}$, which may be the same or different is selected from fluoro, chloro and bromo); and a is 0, 1 or 2 (particularly 0 or 1);

or a pharmaceutically acceptable salt thereof.

A further embodiment of the invention is a quinazoline derivative of the formula I of the formula Ia as hereinabove defined wherein $Z^1$ is selected from (1-2C)alkyl, hydroxy-(1-2C)alkyl, amino-(1-2C)alkyl, (1-4C)alkylamino-(1-2C)alkyl and di-[(1-4C)alkyl]amino-(1-2C)alkyl, or $Z^1$ is $Q^2$, wherein $Q^2$ is pyrrolidinyl-(1-2C)alkyl (particularly pyrrolidin-1-yl-(1-2C)alkyl)), and wherein the pyrrolidinyl group within $Z^1$ optionally bears one or more (for example 1, 2 or 3) substituents, which may be the same or different selected from fluoro, chloro, hydroxy, (1-3C)alkyl, (1-3C)alkoxy, or from a group of the formula:

—$X^2$—$R^4$ wherein $X^2$ is a direct bond or is O, and $R^4$ is halogeno-(1-3C)alkyl, hydroxy-(1-3C)alkyl or (1-3C)alkoxy-(1-3C)alkyl, and wherein any the pyrrolidinyl group within $Z^1$ optionally bears an oxo substituent; and wherein $R^{1a}$, m, $R^{11}$, $Z^1$, $Y^1$, $R^{2a}$ and a are as defined above; or a pharmaceutically acceptable salt thereof.

A further embodiment of the invention is a quinazoline derivative of the formula I of the formula Ia as hereinabove defined wherein m is 1 and $R^{1a}$ is selected from (1-4C)alkoxy, hydroxy-(1-4C)alkoxy and (1-4C)alkoxy(1-4C)alkoxy; and $R^{11}$, $Z^1$, $Y^1$, $R^{2a}$ and a are as defined above; or a pharmaceutically acceptable salt thereof.

A further embodiment of the invention is a quinazoline derivative of the formula I of the formula Ia as hereinabove defined wherein $R^{11}$ is selected from hydrogen, hydroxy and (1-3C)alkoxy (particularly, $R^{11}$ is selected from hydrogen, hydroxy and methoxy, more particularly $R^{11}$ is hydrogen or hydroxy); and m, $R^{1a}$, $Z^1$, $Y^1$, $R^{2a}$ and a are as defined above; or a pharmaceutically acceptable salt thereof.

A further embodiment of the invention is a quinazoline derivative of the formula I of the formula Ia as hereinabove defined wherein the aniline of the formula:

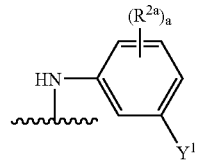

is selected from 3-chloro-4-fluoroanilino, 3-chloro-2-fluoroanilino, 2-fluoro-5-chloroanilino, 3-bromoanilino, 3-methylanilino and 3-ethynylanilino (particularly the aniline is 3-chloro-4-fluoroanilino or 3-chloro-2-fluoroanilino, more particularly 3-chloro-4-fluoroanilino); and m, $Z^1$, $R^{1a}$ and $R^{11}$ are as defined above; or a pharmaceutically acceptable salt thereof.

A further embodiment of the invention is a quinazoline derivative of the formula I of the formula Ia as hereinabove defined wherein the pyrrolidin-2-ylmethoxy group at the 5-position in the quinazoline ring in formula Ia is the (2R)-pyrrolidin-2-ylmethoxy enantiomer and m, $R^1$a, $R^{11}$, $Z^1$, $Y^1$, $R^{2a}$ and a are as defined above; or a pharmaceutically acceptable salt thereof.

A further embodiment of the invention is a quinazoline derivative of the formula I of the formula Ia as hereinabove defined wherein:

m is 1 and $R^{1a}$ is selected from methoxy, ethoxy, 2-hydroxyethoxy, 2-methoxyethoxy and 2-ethoxyethoxy;

$R^{11}$ is selected from hydrogen, hydroxy or methoxy (particularly hydrogen or hydroxy);

$Z^1$ is selected from methyl, hydroxymethyl, aminomethyl, methylaminomethyl, dimethylaminomethyl and pyrrolidin-1-ylmethyl (particularly $Z^1$ is selected from methyl, hydroxymethyl, dimethylaminomethyl and pyrrolidin-1-ylmethyl);

$Y^1$ is selected from fluoro, chloro, bromo and ethynyl (particularly $Y^1$ is fluoro or chloro);

$R^{2a}$ is selected from fluoro, chloro and bromo (particularly $R^{2a}$ is fluoro or chloro); and a is 0 or 1;

or a pharmaceutically acceptable salt thereof.

In this embodiment a preferred aniline at the 4-position in the quinazoline ring in formula Ia is 3-chloro-4-fluoroanilino or 3-chloro-2-fluoroanilino (particularly 3-chloro-4-fluoroanilino).

A further embodiment of the invention is a quinazoline derivative of the formula I of the formula Ia as hereinabove defined wherein:

m is 1 and $R^{1a}$ is selected from methoxy, ethoxy, 2-hydroxyethoxy, 2-methoxyethoxy and 2-ethoxyethoxy (particularly $R^{1a}$ is selected from methoxy, and 2-ethoxyethoxy);

$R^{11}$ is selected from hydrogen or hydroxy;

$Z^1$ is selected from methyl or hydroxymethyl;

$Y^1$ is selected from fluoro, chloro, bromo and ethynyl (particularly $Y^1$ is fluoro or chloro);

$R^{2a}$ is selected from fluoro, chloro and bromo particularly $R^{2a}$ is fluoro or chloro); and a is 0 or 1;

or a pharmaceutically acceptable salt thereof.

In this embodiment a preferred aniline at the 4-position in formula Ia is 3-chloro-4-fluoroanilino or 3-chloro-2-fluoroanilino (particularly 3-chloro-4-fluoroanilino).

A particular compound of the invention is, for example, a quinazoline derivative of the formula I selected from:

2-{(2R)-2-[({4-[3-Chloro-4-fluoroanilino]-7-methoxyquinazolin-5-yl}oxy)methyl]pyrrolidin-1-yl}-2-oxoethanol;

N-(3-chloro-4-fluorophenyl)-5-({(2R)-1-[(dimethylamino)acetyl]pyrrolidin-2-yl}methoxy)-7-methoxyquinazolin-4-amine;

N-(3-chloro-4-fluorophenyl)-7-methoxy-5-{[(2S)-1-(pyrrolidin-1-ylacetyl)pyrrolidin-2-yl]methoxy}quinazolin-4-amine;

(3S,5S)-5-[({4-[3-chloro-fluoroanilino]-7-methoxyquinazolin-5-yl}oxy)methyl]-1-(N,N-dimethylglycyl)pyrrolidin-3-ol;

(3S,5R)-5-[({4-[3-chloro-4-fluoroanilino]-7-methoxyquinazolin-5-yl}oxy)methyl]-1-(N,N-glycoloylpyrrolidin-3-ol;

(3R,5R)-5-[({4-[3-chloro-4-fluoroanilino]-7-methoxyquinazolin-5-yl}oxy)methyl]-1-glycoloylpyrrolidin-3-ol;

(3R,5R)-5-[({4-[3-chloro-4-fluoroanilino]-7-methoxyquinazolin-5-yl}oxy)-methyl]dimethylglycyl)pyrrolidin-3-ol;

(3S,5R)-1-acetyl-5-[({4-[3-chloro-4-fluoroanilino]-7-methoxyquinazolin-5-yl}oxy)methyl]pyrrolidin-3-ol;

2-[(2R)-2-({[4-[3-chloro-4-fluoroanilino]-7-(2-hydroxyethoxy)quinazolin-5-yl]oxy}methyl)pyrrolidin-1-yl]-2-oxoethanol;

2-[(2R)-2-({[4-[3-chloro-4-fluoroanilino]-7-(2-ethoxyethoxy)quinazolin-5-yl]oxy}methyl)pyrrolidin-1-yl]-2-oxoethanol;

2-{(2R)-2-[({4-[3-chloro-4-fluoroanilino]-7-ethoxyquinazolin-5-yl}oxy)methyl]-pyrolidin-1-yl}-2-oxoethanol; and N-(3-chloro-4-fluorophenyl)-7-methoxy-5-{[(2R)-1-(methoxyacetyl)pyrrolidin-2-yl]methoxy}quinazolin-4-amine;

or a pharmaceutically acceptable salt thereof.

A further particular compound of the invention is, for example, a quinazoline derivative of the formula I selected from:

2-{(2R)-2-[({-[3-Chloro-4-fluoroanilino]-7-methoxyquinazolin-5-yl}oxy)methyl]pyrrolidin-1-yl}-2-oxoethanol;

N-(3-Chloro-4-fluorophenyl)-5-({(2R)-1-[(dimethylamino)acetyl]pyrrolidin-2-yl}methoxy)-7-methoxyquinazolin-4-amine; and N-(3-Chloro-4-fluorophenyl)-7-methoxy-5-{[(2S)-1-(pyrrolidin-1-ylacetyl)pyrrolidin-2-yl]methoxy}quinazolin-4-amine;

or a pharmaceutically acceptable salt thereof.

A quinazoline derivative of the formula I, or a pharmaceutically-acceptable salt thereof, may be prepared by any process known to be applicable to the preparation of chemically-related compounds. Suitable processes include, for example, those illustrated in European Patent Applications Nos. 0520722, 0566226, 0602851, 0635507 and 0635498, and International Patent Applications WO 96/15118, WO 96/16960 and WO01/94341. Such processes, when used to prepare a quinazoline derivative of the formula I are provided as a further feature of the invention and are illustrated by the following representative process variants in which, unless otherwise stated, $R^1$, $R^2$, $X^1$, $Y$, $Q^1$, $Z$ a and m have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

Process (a) The coupling, conveniently in the presence of a suitable base, of a quinazoline of the formula II:

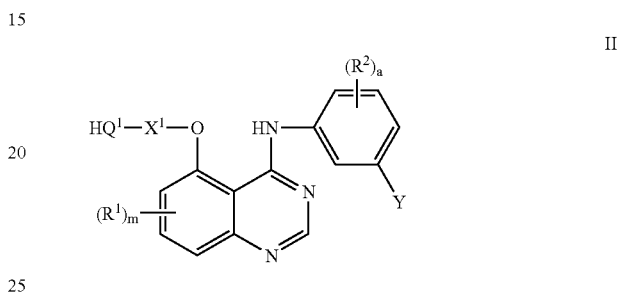

II wherein $R^1$, $R^2$, $X^1$, $Y$, $Q^1$, a and m have any of the meanings defined hereinbefore except that any functional group is protected if necessary, with a carboxylic acid of the formula Z—COOH, or a reactive derivative thereof, wherein Z has any of the meanings defined hereinbefore except that any functional group is protected if necessary;

or

Process (b): for the preparation of those compounds of the formula I wherein Z is selected from amino-(1-4C)alkyl, (1-4C)alkylamino-(1-4C)alkyl, di-[(1-4C)alkyl]amino-(1-4C)alkyl, or Z is $Q^2$, wherein $Q^2$ is heterocyclyl-(1-4C)alkyl, and wherein the heterocyclyl in $Q^2$ contains at least 1 nitrogen heteroatom, and optionally 1 or 2 further heteroatoms selected from oxygen, nitrogen and sulfur, and wherein $Q^2$ is attached by a ring nitrogen atom, the reaction of a quinazoline of the formula III:

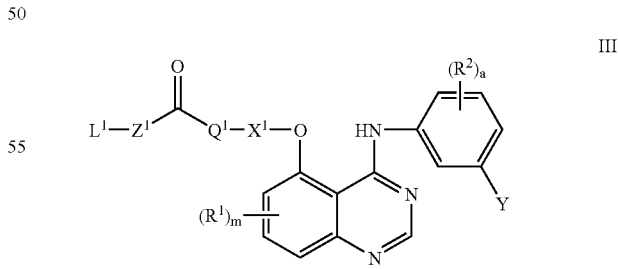

III wherein $R^1$, $R^2$, $X^1$, $Y$, $Q^1$, a and m have any of the meanings defined hereinbefore except that any functional group is protected if necessary, $Z^1$ is a direct bond or (1-4C)alkyl and $L^1$ is a displaceable group, with an amine or a compound of the formula Q²H wherein Q² has any of the meanings defined hereinbefore except that any functional group is protected if necessary;

or

Process (c): for the preparation of those compounds of the formula I wherein $R^1$ is a hydroxy group, the cleavage of a quinazoline derivative of the formula I wherein $R^1$ is a (1-6C) alkoxy;

or

Process (d): for the preparation of those compounds of the formula I wherein m is 1 and $R^1$ is optionally substituted (1-6C)alkoxy, optionally substituted (2-6C)alkenyloxy, optionally substituted (2-6C)alkynyloxy or a group of the formula:

$Q^3$—$X^3$— wherein $X^3$ is O, and $Q^3$ is as hereinbefore defined except that any functional group is protected if necessary, and the optional substituents on $R^1$ are those that may be present on $R^1$ as hereinbefore defined in relation to formula I, the reaction, conveniently in the presence of a suitable base, of a quinazoline of the formula IV:

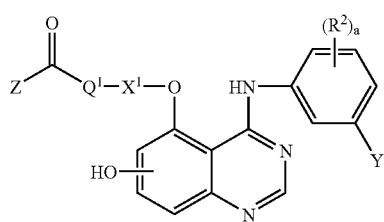

wherein $R^2$, $X^1$, Y, $Q^1$, Z and a have any of the meanings defined hereinbefore except that any functional group is protected if necessary, with a compound of the formula $R^{1a}$—$L^1$ or $Q^3$—$L^1$ wherein $Q^3$ is as hereinbefore defined except any functional group is protected if necessary, $R^{1a}$ is selected from optionally substituted (1-6C)alkyl, optionally substituted (2-6C)alkenyl and optionally substituted (2-6C)alkynyl and $L^1$ is a displaceable group, and wherein the optional substituents on $R^{1a}$ are the same as those that may be present on the corresponding groups on $R^1$ as hereinbefore defined in relation to formula I;

or

Process (e): for the preparation of those compounds of the formula I wherein m is 1 and $R^1$ is optionally substituted (1-6C)alkoxy, optionally substituted (2-6C)alkenyloxy, optionally substituted (2-6C)alkynyloxy or a group of the formula:

$Q^3$—$X^3$— wherein $X^3$ is O, and $Q^3$ is as hereinbefore defined and the optional substituents on $R^1$ are those that may be present on $R^1$ as hereinbefore defined in relation to formula I, the coupling of the a quinazoline of the formula IV as hereinbefore defined with an alcohol of the formula $R^{1a}$OH or $Q^3$OH wherein $Q^3$ is as hereinbefore defined except any functional group is protected if necessary and $R^{1a}$ is as hereinbefore defined in process (d);

and thereafter, if necessary:

(i) converting a quinazoline derivative of the formula I into another quinazoline derivative of the formula I;

(ii) removing any protecting group that is present by conventional means;

(iii) forming a pharmaceutically acceptable salt.

Specific conditions for the above reactions are as follows:

Process (a)

The coupling reaction is conveniently carried out in the presence of a suitable coupling agent, such as a carbodiimide, or a suitable peptide coupling agent, for example O-(7-azabenzotriazol-1-yl)-N,N,N',N'-tetramethyluronium hexafluoro-phosphate or 4-(4,6-dimethoxy[1.3.5]triazin-2-yl)-4-methylmorpholinium chloride, or a carbodiimide such as dicyclohexylcarbodiimide, optionally in the presence of a catalyst such as dimethylaminopyridine or 4-pyrrolidinopyridine.

The coupling reaction is conveniently carried out in the presence of a suitable base. A suitable base is, for example, an organic amine base such as, for example, pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate, for example sodium carbonate, potassium carbonate, cesium carbonate, calcium carbonate, or, for example, an alkali metal hydride, for example sodium hydride.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 120° C., particularly at or near ambient temperature.

By the term "reactive derivative" of the carboxylic acid of the formula Z—COOH is meant a carboxylic acid derivative that will react with the quinazoline of formula II to give the corresponding amide. A suitable reactive derivative of a carboxylic acid of the formula ZCCOH is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate, an alcohol such as methanol, ethanol, isopropanol, butanol or N-hydroxybenzotriazole, or an active ester formed by the reaction of the acid and an activated triazine such as 4-(4,6-dimethoxy[1.3.5]triazin-2-yl)-4-methylmorpholinium chloride hydrate; or an acyl azide, for example an azide formed by the reaction of the acid and azide such as diphenylphosphoryl azide; an acyl cyanide, for example a cyanide formed by the reaction of an acid and a cyanide such as diethylphosphoryl cyanide. The reaction of these reactive derivatives of carboxylic acid with amines (such as a compound of the formula II) is well known in the art, for Example they may be reacted in the presence of a base, such as those described above, and in a suitable solvent, such as those described above. The reaction may conveniently be performed at a temperature as described above.

The quinazoline of the formula II may be obtained by conventional procedures. For example, a quinazoline derivative of the formula II wherein m is 1 and $R^1$ is optionally substituted (1-6C)alkoxy and is located at the 7-position may be prepared according to Reaction Scheme 1:

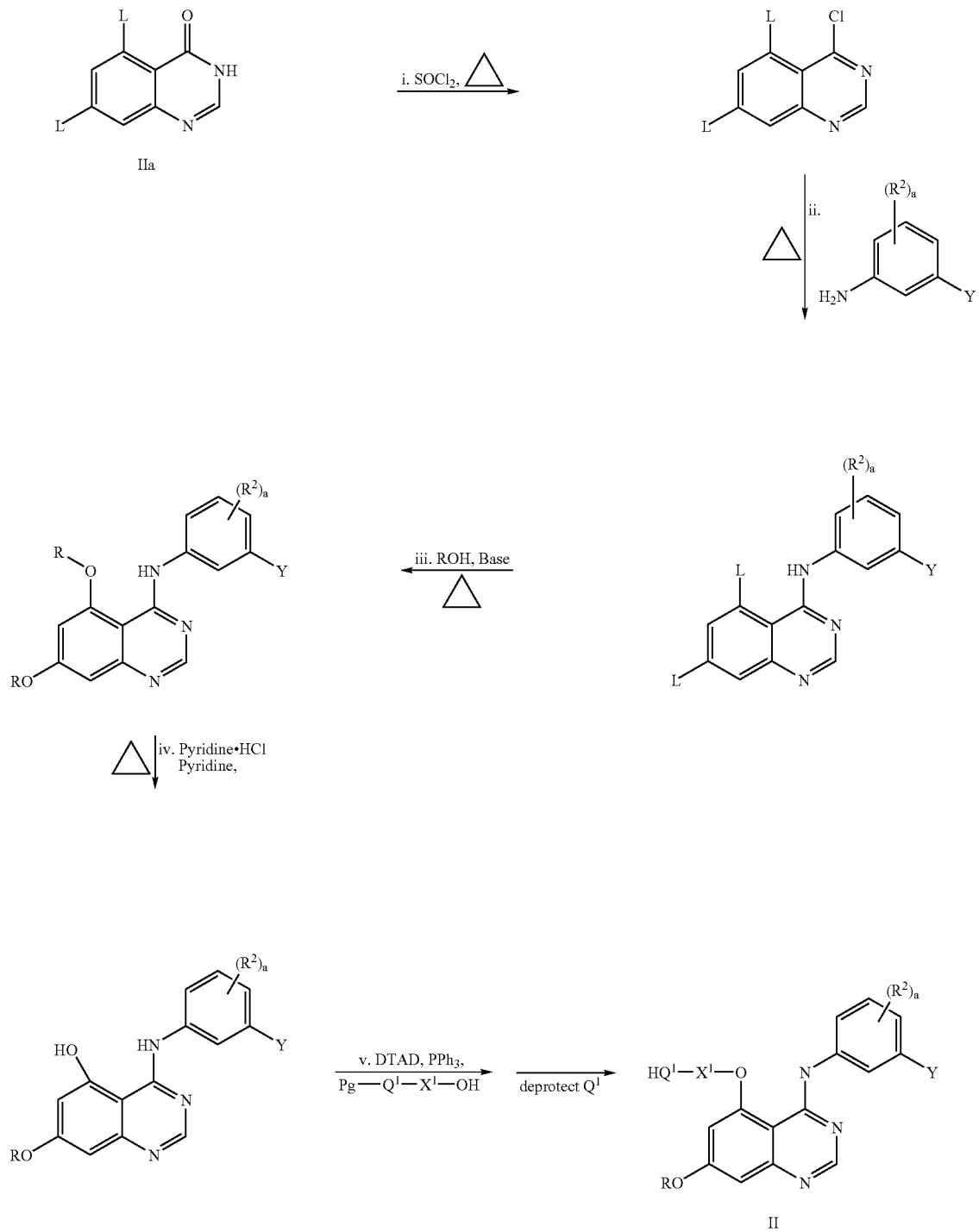

Notes for Reaction Scheme 1:

L is a suitable displaceable group;

R is optionally substituted (1-6C)alkyl;

Pg is a protecting group; and $R^2$, $X^1$, Y, $Q^1$, Z and a have any of the meanings defined hereinbefore, except any functional group is protected if necessary and any protecting groups present are removed either following a particular reaction step or at the end of Reaction Scheme 1 to give the compound of formula II.

Step (i)

A suitable displaceable group represented by L includes, for example a halogeno or a sulfonyloxy group, for example fluoro, chloro, methylsulfonyloxy or toluene-4-sulfonyloxy group. A particular group L is fluoro or chloro, more particularly fluoro.

The halogenation reaction (chlorination shown) may be carried out using a suitable chlorinating agent such as thionyl chloride (as shown), phosphoryl chloride or a mixture of carbon tetrachloride and triphenylphosphine.

The halogenation reaction is conveniently carried out in a suitable solvent, for example 1,2-dichloroethane or N,N-dimethylformamide conveniently in the presence of an base such as an organic base, for example di-isopropylethylamine. The reaction is conveniently carried out at a temperature in the range, for example, 0 to 150° C., preferably at or near the reflux temperature.

Compounds of the formula IIa are commercially available compounds or they are known in the literature, or they can be can be prepared by standard processes known in the art. For example when each L in the compound of formula IIa is fluoro, the 5,7-difluoro-3,4-dihydroquinazolin-4-one starting material may be prepared using the method described in WO01/94341, example 4, footnote [5].

Step (ii):

The reaction is conveniently carried out in the presence of an acid. Suitable acids include, for example hydrogen chloride gas (conveniently dissolved in diethyl ether or dioxane) or hydrochloric acid.

Alternatively, the reaction may be carried out in the presence of a suitable base. A suitable base is, for example, an organic amine base such as, for example, one of the bases described above in relation to process (a).

Alternatively the quinazoline derivative may be reacted with the aniline in the absence of an acid or a base. In this reaction displacement of the chloro leaving group results in the formation of the hydrochloric acid in-situ and the autocatalysis of the reaction.

The reaction in step (ii) is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulfoxide. The above reaction is conveniently carried out at a temperature in the range, for example, 0 to 250° C., conveniently in the range 40 to 80° C. or, preferably, at or near the reflux temperature of the solvent when used. Conveniently, the above reaction may be performed in the presence of a suitable catalyst, for example a crown ether.

The anilines used as a starting material in step (ii) are commercially available compounds or they are known in the literature, or they can be can be prepared by standard processes known in the art.

Step (iii)

A suitable base for the reaction the quinazoline and the alcohol of the formula ROH includes, for example a strong non-nucleophilic base such as an alkali metal hydride, for example sodium hydride, an alkali metal amide, for example lithium di-isopropylamide (LDA) or an alkali metal alkoxide such as potassium tert-butoxide or sodium tert-butoxide.

The reaction is conveniently carried out in the presence of a suitable inert solvent or diluent, for example a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range of, for example, from 10 to 250° C., preferably in the range of from 40 to 150° C.

Step (iv)

Cleavage of the (1-6C)alkoxy group may be performed using an analogous procedure to that described for process (c) below, for example by reaction with pyridine hydrochloride as shown in Reaction Scheme 1.

Step (v)

Coupling reaction under Mitsunobu conditions. The coupling of alcohols using the Mitsunobu coupling reaction is well known in the art and is discussed in detail in, for example, Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164. For example suitable Mitsunobu conditions include, reaction in the presence of a suitable tertiary phosphine and a di-alkylazodicarboxylate, conveniently in the presence of a suitable organic solvent. A suitable tertiary phosphine includes for example tri-n-butylphosphine or tri-phenylphosphine (as shown). A suitable di-alkylazodicarboxylate includes for example diethyl azodicarboxylate (DEAD) or di-tert-butyl azodicarboxylate (DTAD, as shown in Reaction Scheme 1). Conveniently the reaction is carried out in an organic solvent, for example a halogenated solvent such as methylene chloride, or an ether such as tetrahydrofuran. The reaction is suitably carried out in the temperature range of from 0° C. to 60° C., suitably at ambient temperature.

Alcohols of the formula $HQ^1$—$X^1$—OH used as the starting material in step (ii) (prior to protecting with the protecting group Pg) are commercially available compounds or they are known in the literature, or they can be can be prepared by standard processes known in the art. The protecting group Pg is present on the NH group in $Q^1$ to which the group of the formula ZC(O) is attached in the quinazoline of the formula I. The protecting group is a suitable amine protecting group as described herein, for example a tert-butoxycarbonyl protecting group (BOC). When $Q^1$ carries other functional groups, for example a hydroxy group, it may be necessary to protect such groups with additional suitable protecting groups for such functional groups as described herein. For example if additional hydroxy groups are present, a suitable hydroxy protecting group is tert-butyl(dimethyl)silyloxy group. The protecting groups present may be removed following the Mitsunobu coupling, for example by treatment with a suitable acid such as trifluoroacetic acid.

Compounds of the formula II wherein $R^1$ is at the 7-position may also be prepared according to Reaction Scheme 1a:

Reaction Scheme 1a

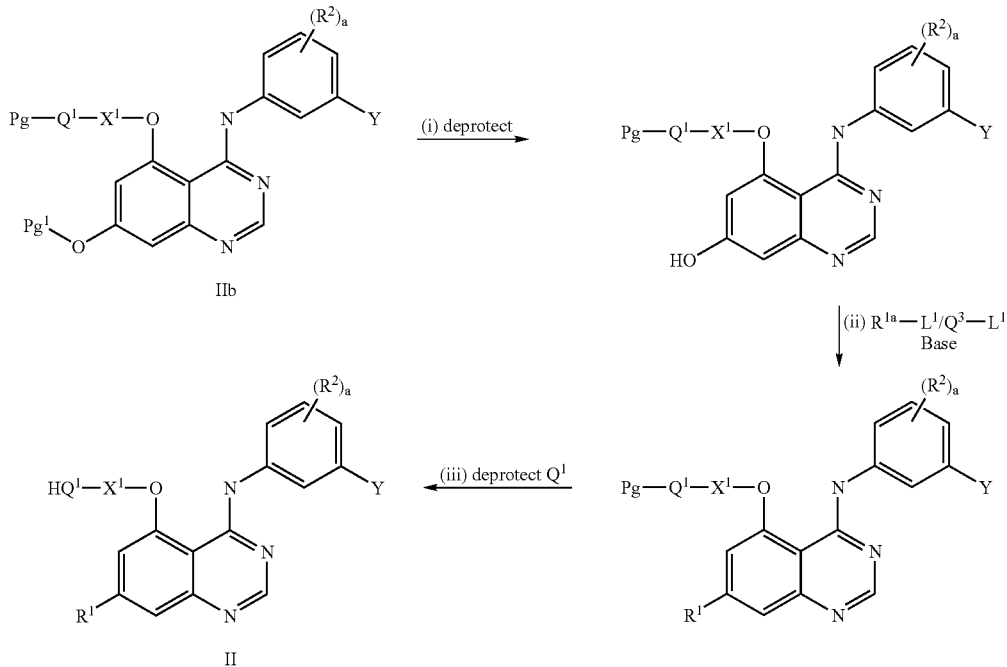

Notes for Reaction Scheme 1a:

$L^1$ is a suitable displaceable group as defined hereinafter in relation to Process (d);

Pg is a suitable amine protecting group as defined hereinbefore in relation to Reaction Scheme 1;

$Pg^1$ is a suitable hydroxy protecting group; and $R^1$, $R^2$, $X^1$, Y, $Q^1$, Z and a have any of the meanings defined hereinbefore, except any functional group is protected if necessary and any protecting groups present are removed either following a particular reaction step or at the end of Reaction Scheme 1a to give the compound of formula II.

Step (i)

$Pg^1$ is a suitable hydroxy protecting group, for example an aryl-lower alkyl group such as benzyl. The protecting group $Pg^1$ may be removed using standard methods well known in the art. For example, when $Pg^1$ is benzyl, the protecting group may be removed by hydrogenation. Suitable hydrogenation conditions are well known, for example by hydrogenation in the presence of a palladium catalyst.

Compounds of formula IIb may be prepared by standard processes known in the art, for example using the process described in Reaction Scheme 3.

Step (ii)

Carried out under analogous conditions to those used in Process (d) described herein.

Step (iii)

The protecting group Pg may be removed using standard conditions, for example when Pg is tert-butoxycarbonyl, be treatment with trifluoroacetic acid.

Compounds of the formula II wherein $R^1$ is not at the 7-position, may be prepared using analogous methods to those described above in Reaction Schemes 1 and 1a using appropriate starting materials.

Process (b)

Suitable displaceable groups represented by $L^1$ in the quinazoline of formula II include halogeno, or a sulfonyloxy group, for example chloro or bromo, methane sulfonyloxy or toluenesulfonyloxy, particularly halogeno such as chloro. The reaction is suitably performed in the presence of a suitable inert solvent or diluent, for example a solvent(s) or diluent(s) described above in relation to process (a) such as a chlorinated solvent, for example dichloromethane or a dipolar aprotic solvent such as N,N-dimethylformamide. Suitably the reaction is carried out at a temperature of, for example 0 to 180° C., particularly 20° C. to the reflux temperature of the solvent/diluent.

The reaction is conveniently carried out in the presence of a base. Suitable bases include, for example, those described above in relation to process (a) such as a carbonate, for example cesium carbonate, or a tertiary amine, for example diisopropylethylamine. Alternatively, an excess of the amine or the compound of the formula $Q^2H$ may be used to provide the required basic conditions.

The amines and compounds of the formula $Q^2H$ used in process (b) are commercially available compounds or they are known in the literature, or they can be can be prepared by standard processes known in the art.

The quinazoline of the formula III may be obtained by conventional procedures. For example a quinazoline of the formula III wherein m is 1, $R^1$ is (1-6C)alkoxy and is located at the 7-position may be prepared as described in Reaction Scheme 2:

Reaction Scheme 2

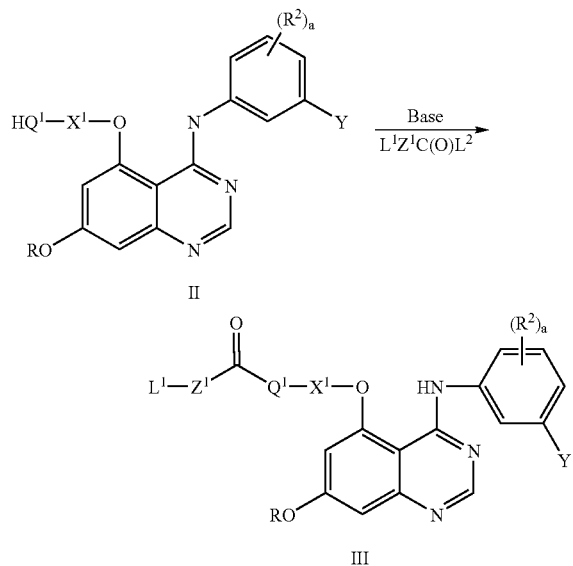

Notes for Reaction Scheme 2:

$L^1$ and $L^2$ are displaceable groups;

R is (1-6C)alkyl; and $R^2$, $X^1$, Y, $Q^1$, $Z^1$ and a have any of the meanings defined hereinbefore, except any functional group is protected if necessary and any protecting groups present are removed following the reaction to give the compound of formula III.

Suitable displaceable groups represented by $L^1$ and $L^2$ are as hereinbefore described for $L^1$ in process (b), provided that $L^2$ is more labile than $L^1$. Suitably, $L^1$ and $L^2$ are both halogeno, for example both are chloro.

The reaction is conveniently carried out in the presence of a base. Suitable bases include, for example those described above in relation to process (a), such as an organic amine, for example di-isopropylethylamine. The reaction is suitably performed in the presence of a suitable inert solvent or diluent, for example a solvent(s) or diluent(s) described above in relation to process (a) such as a methylene chloride. Suitably the reaction is carried out at a temperature of, for example 0 to 180° C., particularly 20° C. to the reflux temperature of the solvent/diluent.

Compound of the formula $L^1Z^1C(O)L^2$ used as the starting material in Reaction Scheme 2 are commercially available compounds or they are known in the literature, or they can be can be prepared by standard processes known in the art. The compound of the formula II used as a starting material in Reaction Scheme 2 may be prepared using conventional methods, for example the process described in Reaction Scheme 1.

In a variant to Process (b) the reaction may be telescoped starting from the compound of formula II by reacting the compound of the formula $L^1Z^1C(O)L^2$ and a compound of formula II followed by reaction with a suitable amine or the compound of the formula $Q^2H$ as described above. Such a process avoids the need to isolate the intermediate compound of the formula III.

Process (c)

The cleavage reaction may conveniently be carried out by any of the many procedures known for such a transformation. The cleavage reaction of a compound of the formula I wherein $R^1$ is a (1-6C)alkoxy group may be carried out, for example, by treatment of the quinazoline derivative with an alkali metal (1-6C)alkylsulfide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide, or by reaction with an organic or inorganic acid, for example trifluoroacetic acid. Such reactions are suitably carried out in the presence of a suitable inert solvent or diluent as defined hereinbefore. A preferred cleavage reaction is the treatment of a quinazoline derivative of the formula I with pyridine hydrochloride. The cleavage reactions are suitably carried out at a temperature in the range, for example, from 10 to 150° C., for example from 25 to 80° C.

Process (d)

Suitable displaceable groups represented by $L^1$ are as hereinbefore defined in relation to process (b), for example $L^1$ is halogeno such as chloro or bromo. Suitable bases are as hereinbefore defined in relation to process (a), for example an alkali or alkaline earth metal carbonate, for example sodium carbonate, potassium carbonate, cesium carbonate, calcium carbonate. The reaction is suitably carried out under analogous conditions and in the presence of the solvents described above for process (b).

The compounds of the formulae $R^{1a}-L^1$ and $Q^3-L^1$ used as the starting materials in Process (d) are commercially available compounds or they are known in the literature, or they can be can be prepared by standard processes known in the art.

The compound of formula IV used in process (d) may be prepared using conventional techniques, for example by cleavage of an alkoxy group from another compound of formula I using process (c).

Alternatively, the compound of formula IV may be prepared as described in Reaction Scheme 3:

Reaction Scheme 3

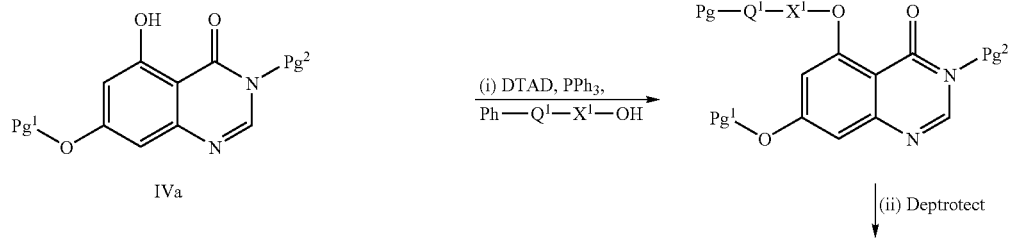

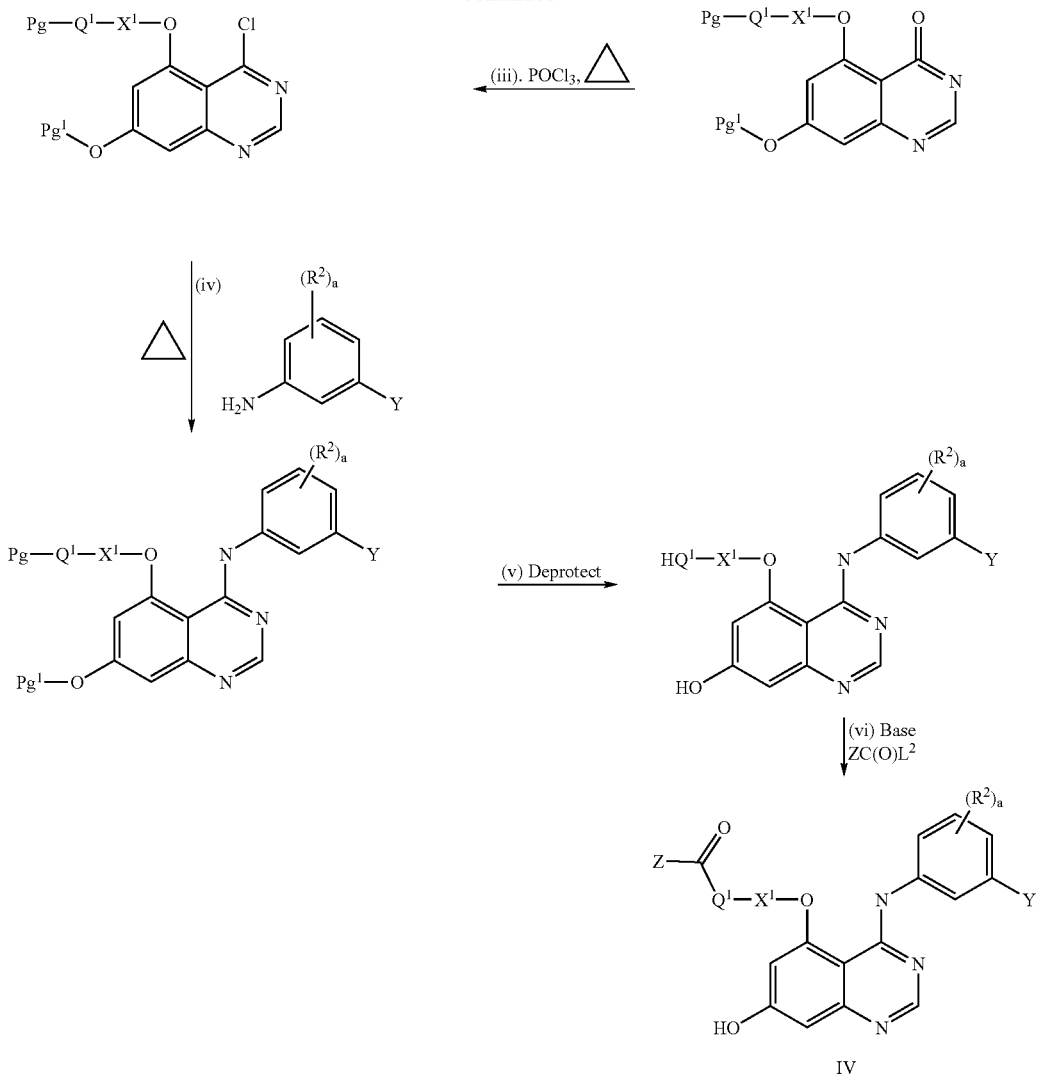

Notes for Reaction Scheme 3

Pg and $Pg^2$ are suitable amine protecting groups;

$Pg^1$ is a suitable hydroxy protecting group;

$L^2$ is a suitable displaceable group, for example halogeno such as chloro; and $R^1$, $R^2$, $X^1$, Y, $Q^1$, Z and a have any of the meanings defined hereinbefore, except any functional group is protected if necessary and any protecting groups present are removed either following a particular reaction step or at the end of Reaction Scheme 3 to give the compound of formula IV.

Step (i): The reaction is carried out under Mitsunobu conditions as described herein in relation to Reaction Scheme 1 (step (v)).

Suitable hydroxy protecting groups represented by $Pg^1$ are as defined above in relation to Reaction Scheme 1a, for example benzyl.

Suitable amino protecting groups represented by $Pg^2$ are as well known in the art and include for example lower alkanoyloxyalkyl groups such as pivaloyloxymethyl. Suitable amino protecting groups represented by Pg are as hereinbefore defined, for example tert-butoxycarbonyl.

Compounds of formula IVa used as the starting material in Reaction Scheme 3 are known and can be prepared using conventional methods, for example as described in Example 15[8] of WO01/94341.

Step (ii): The protecting group $Pg^2$ may be removed using standard conditions. For example when $Pg^2$ is a lower alkanoyloxyalkyl group, by treatment with methanolic ammonia.

Step (iii): Halogenation under analogous conditions to those used in step (i) of Reaction Scheme 1. Alternative halogenation agents to the $POCl_3$ shown in Reaction Scheme 3 may be used if desired. Such halogenation agents are well known and include, for example thionyl chloride.

Step (iv): Aniline coupling using analogous conditions to those used in Step (ii) of Reaction Scheme 1.

Step (v): Deprotection to remove Pg and $Pg^1$ using standard techniques well known in the art. For example by treatment with trifluoroacetic acid.

Step (vi): Analogous conditions to those used in Reaction Scheme 2. Compounds of the formula ZC(O)L² are commercially available compounds or they are known in the literature, or they can be can be prepared by standard processes known in the art.

Process (e)

Suitably the coupling reaction is carried out under Mitsunobu conditions using an analogous procedure to that described above in step (iv) of Reaction Scheme 1.

The compounds of the formulae $R^{1a}OH$ and $Q^3OH$ used as the starting materials in Process (e) are commercially available compounds or they are known in the literature, or they can be can be prepared by standard processes known in the art.

The quinazoline derivative of the formula I may be obtained from the above processes in the form of the free base or alternatively it may be obtained in the form of a salt, for example in process (b) an acid addition salt may be produced with the acid of the formula H—L¹ when L¹ is, for example halogeno such as chloro. When it is desired to obtain the free base from a salt of the compound of formula I, the salt may be treated with a suitable base, for example, an alkali or alkaline earth metal carbonate or hydroxide, for example sodium carbonate, potassium carbonate, calcium carbonate, sodium hydroxide or potassium hydroxide, or by treatment with ammonia for example using a methanolic ammonia solution such as 7N ammonia in methanol.

The protecting groups used in the processes above may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example alkyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example alkyl); lower alkanoyl groups (for example acetyl); lower alkoxycarbonyl groups (for example tert-butoxycarbonyl); lower alkenyloxycarbonyl groups (for example alkyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example alkyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); lower alkanoyloxyalkyl groups (for example pivaloyloxymethyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl. For example a tert butoxycarbonyl protecting group may be removed from an amino group by an acid catalysed hydrolysis using trifluoroacetic acid.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the oxidation of alkylthio to alkylsulfinyl or alkylsulfonyl; the substitution of an NH or OH group in $R^1$ by the reaction with an optionally substituted alkyl halide or an optionally substituted alkyltosylate. An analogous procedure may be used to introduce optionally substituted (2-6C)alkenyloxy or (2-6C)alkynyloxy groups into $R^1$.

When a pharmaceutically-acceptable salt of a quinazoline derivative of the formula I is required, for example an acid-addition salt, it may be obtained by, for example, reaction of said quinazoline derivative with a suitable acid using a conventional procedure.

As mentioned hereinbefore some of the compounds according to the present invention may contain one of more chiral centers and may therefore exist as stereoisomers (for example when $Q^1$ is pyrrolidin-2-yl). Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free for other stereoisomers, for example containing less than 20%, particularly less than 10% and more particularly less than 5% by weight of other stereoisomers.

In the section above relating to the preparation of the compound of formula I, the expression "inert solvent" refers to a solvent which does not react with the starting materials, reagents, intermediates or products in a manner which adversely affects the yield of the desired product.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

Biological Assays

The following assays may be used to measure the effects of the compounds of the present invention as inhibitors of the erbB-tyrosine kinases, as inhibitors in-vitro of the proliferation of KB cells (human naso-pharangeal carcinoma cells) and H16N-2 cells, and as inhibitors in vivo on the growth in nude mice of xenografts of LoVo tumour cells (colorectal adenocarcinoma).

a) Protein Tyrosine Kinase Phosphorylation Assays

This test measures the ability of a test compound to inhibit the phosphorylation of a tyrosine containing polypeptide substrate by EGFR tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM $MgCl_2$, 1 mM ethylene glycol-bis(β-aminoethyl ether) N',N',N',N'-tetraacetic acid (EGTA), plus protease inhibitors and then cleared by centrifugation.

Constitutive kinase activity of the recombinant protein was determined by its ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 kg of peptide in a 100 μl phosphate buffered saline (PBS) solution and incubated at 4° C. overnight). Plates were washed in PBS-T (phosphate buffered saline with 0.5% Tween 20) then in 50 mM HEPES pH 7.4 at room temperature to remove any excess unbound synthetic peptide. EGFR, ErbB2 or ErbB4 tyrosine kinase activity was assessed by incubation in peptide coated plates for 20 minutes at 22° C. in 100 mM HEPES pH 7.4, adenosine trisphosphate (ATP) at Km concentration for the respective enzyme, 10 mM $MnCl_2$, 0.1 mM $Na_3VO_4$, 0.2 mM DL-dithiothreitol (DTT), 0.1% Triton X-100 with test compound in DMSO (final concentration of 2.5%). Reactions were terminated by the removal of the liquid components of the assay followed by washing of the plates with PBS-T.

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (BRP) conjugated sheep anti-mouse secondary antibody (NXA931 from Amersham) for 60 minutes at room temperature. After further washing, HRP activity in each well of the plate was measured calorimetrically using 22'-Azino-di-[3-ethylbenzthiazoline sulfonate (6)] diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) KB Cell Proliferation Assay

This assay measures the ability of a test compound to inhibit the EGF driven proliferation of KB cells (human nasopharangeal carcinoma obtained from the American Type Culture Collection (ATCC)).

KB cells were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.25 \times 10^3$ cells per well of a 96 well plate in DMEM containing 2.5% charcoal stripped serum, 2 mM glutamine and non-essential amino acids at 37° C. in 7.5% $CO_2$ and allowed to settle for 4 hours.

Following adhesion to the plate, the cells are treated with or without EGF (final concentration of 1 ng/ml) and with or without compound at a range of concentrations in dimethyl-sulfoxide (DMSO) (1% final) in a final volume of 200 μl before incubation for 4 days at 37° C. in 7.5% $CO_2$. Following the incubation period, cell numbers were determined by addition of 50 μl of 3-(4,5-Dimethylthiazol-2-yl)-2,5-diphenyltetrazolium bromide (MTT) (stock 5 mg/ml) and incubated at 37° C. in a 7.5% $CO_2$ air incubator for 2 hours. MTT solution was then removed from the cells by aspiration, which were then allowed to air dry and were dissolved upon the addition of 100 μl of DMSO.

Absorbance of this solubilised cells was read at 540 nM to quantify cell biomass. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) H16N-2 Cell Proliferation Assay

This assay measures the ability of a test compound to inhibit heregulin β or EGF driven proliferation of H16N-2 cells. These non-neoplastic epithelial cells respond in a proliferative manner to stimulation with either EGF or heregulin β (Ram, G. R. and Ethier, S. P. (1996) *Cell Growth and Differentiation,* 7, 551-561) were isolated human mammary tissue (Band, V. and Sager, R. Tumour progression in breast cancer. In: J. S. Rhim and A. Dritschilo (eds.), *Neoplastic Transformation in human Cell Culture*, pp 169-178. Clifton, N.J.: Humana Press, 1991) and were obtained from the Dana-Farber Cancer Institute, 44 Binney Street, Boston, Mass. 02115.

H16N-2 cells were routinely cultured in culture medium (a 1:1 mix of Gibco F12 and Ham's αMEM media containing 1% foetal calf serum, 10 mM HEPES, 1 μg/ml Insulin, 12.5 ng/ml EGF, 2.8 μM Hydrocortisone, 2 nM Estradiol 5 μM Ascorbic Acid, 10 μg/ml Transferrin, 0.1 mM Phosphoethanolamine, 15 nM Sodium Selenite, 2 mM Glutamine, 10 nM Tri-iodo-thrynoine, 35 μg/ml Bovine pituitary Extract and 0.1 mM Ethanolamine) at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.0 \times 10^3$ cells per well of a 96 well plate in the above media at 37° C. in 7.5% $CO_2$ and allowed to settle for 72 hours.

Following this, the cells were starved of serum for 24 hours upon the addition of starvation medium (a 1:1 mix of Gibco F12 and Ham's αMEM media containing, 10 mM HEPES, 2 nM Estradiol, 5 μM Ascorbic Acid, 10 μg/ml Transferrin, 0.1 mM Phosphoethanolamine, 15 nM Sodium Selenite, 2 mM Glutamine, and 0.1 mM Ethanolamine) and incubated at 37° C. in 7.5% $CO_2$. The cells were then treated with or without compound at a range of concentrations in dimethylsulfoxide (DMSO) (1% final) for two hours before the addition of exogenous ligand (at a final concentration of 100 ng/ml of heregulin β or 5 ng/ml of EGF) and incubation with both ligand and compound in a total volume of 200 μl for 4 days at 37° C. in 7.5% $CO_2$. Following the incubation period, cell numbers were determined by addition of 50 μl of 3-(4,5-Dimethylthiazol-2-yl)-2,5-diphenyltetrazolium bromide (MIT) (stock 5 mg/ml) and incubated at 37° C. in a 7.5% $CO_2$ air incubator for 2 hours. MT solution was then removed from the cells by aspiration, which were then allowed to air dry and were dissolved upon the addition of 100 μl of DMSO.

Absorbance of this solubilised cells was read at 540 nm to quantify cell biomass. Inhibition of proliferation was expressed as an $IC_{50}$ value. This was determined by calculation of the concentration of compound that was required to give 50% inhibition of proliferation. The range of proliferation was calculated from the positive (vehicle plus ligand) and negative (vehicle minus ligand) control values.

(d) Clone 24 Phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% $CO_2$ air incubator at 37° C. Cells were harvested from T75 stock flasks by washing once in PBS (phosphate buffered saline, pH7.4, Gibco No. 10010-015) and harvested using 2 mls of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of $1 \times 10^4$ cells per well (in 100 ul) into clear bottomed 96 well plates (Packard, No. 6005182).

3 days later, Growth Medium was removed from the wells and replaced with 100 ul Assay Medium (phenol red free DMEM, 2 mM glutamine, 1.2 mg/ml G418) either with or without erbB inhibitor compound. Plates were returned to the incubator for 4 hrs and then 20 μl of 20% formaldehyde solution in PBS was added to each well and the plate was left at room temperature for 30 minutes. This fixative solution was removed with a multichannel pipette, 100 μl of PBS was added to each well and then removed with a multichannel pipette and then 50 μl PBS was added to each well. Plates were then sealed and stored for up to 2 weeks at 4° C.

Immunostaining was performed at room temperature. Wells were washed once with 200 μl PBS/Tween 20 (made by adding 1 sachet of PBS/Tween dry powder (Sigma, No. P3563) to 1 L of double distilled $H_2O$) using a plate washer then 200 μl Blocking Solution (5% Marvel dried skimmed milk (Nestle) in PBS/Tween 20) was added and incubated for 10 minutes. Blocking Solution was removed using a plate washer and 200 μl of 0.5% Triton X-100/PBS was added to permeabalise the cells. After 10 minutes, the plate was washed with 200 μl PBS/Tween 20 and then 200 μl Blocking Solution was added once again and incubated for 15 minutes. Following removal of the Blocking Solution with a plate washer, 30 μl of rabbit polyclonal anti-phospho ErbB2 IgG antibody (epitope phospho-Tyr 1248, SantaCruz, No. SC-12352-R), diluted 1:250 in Blocking Solution, was added to each well and incubated for 2 hours. Then this primary antibody solution was removed from the wells using a plate washer followed by two 200 μl PBS/Tween 20 washes using a plate washer. Then 30 μl of Alexa-Fluor 488 goat anti-rabbit IgG secondary antibody (Molecular Probes, No. A-1008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by two 200 μl PBS/Tween 20 washes using a plate washer. Then 100 μl PBS was added to each plate, incubated for 10 minutes and then removed using a plate washer. Then a further 100 μl PBS was added to each plate and then, without prolonged incubation, removed using a plate washer. Then 50 μl of PBS was added to each well and plates were resealed with black backing tape and stored for up to 2 days at 4° C. before analysis.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an $IC_{50}$ value. This was determined by calculation of the concentration of compound that was required to give 50% inhibition of erbB2 phosphorylation signal.

e) In Vivo Xenograft Assay

This assay measures the ability of a test compound to inhibit the growth of a LoVo tumour (colorectal adenocarcinoma obtained from the ATCC) in Female Swiss athymic mice (Alderley Park, nu/nu genotype).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. LoVo tumour cell (colorectal adenocarcinoma obtained from the ATCC) xenografts were established in the hind flank of donor mice by sub cutaneous injections of $1 \times 10^7$ freshly cultured cells in 100 µl of serum free media per animal. On day 5 post-implant, mice were randomised into groups of 7 prior to the treatment with compound or vehicle control that was administered once daily at 0.1 ml/10 g body weight. Tumour volume was assessed twice weekly by bilateral Vernier caliper measurement, using the formula (length×width)×√(length×width)×(π/6), where length was the longest diameter across the tumour, and width was the corresponding perpendicular. Growth inhibition from start of study was calculated by comparison of the mean charges in tumour volume for the control and treated groups, and statistical significance between the two groups was evaluated using a Students t test.

Although the pharmacological properties of the compounds of the formula I vary with structural change as expected, in general activity possessed by compounds of the formula I, may be demonstrated at the following concentrations or doses in one or more of the above tests (a), (b), (c) and (d):—

Test (a):—$IC_{50}$ in the range, for example, 0.001-10 µM;
Test (b):—$IC_{50}$ in the range, for example, 0.001-10 µM;
Test (c):—$IC_{50}$ in the range, for example, 0.001-10 µM;
Test (d):—$IC_{50}$ in the range, for example, 0.001-10 µM;
Test (e):—activity in the range, for example, 1-200 mg/kg/day;

No physiologically unacceptable toxicity was observed in Test (e) at the effective dose for compounds tested of the present invention. Accordingly no untoward toxicological effects are expected when a compound of formula I, or a pharmaceutically-acceptable salt thereof, as defined hereinbefore is administered at the dosage ranges defined hereinafter.

By way of example, Table A illustrates the activity of representative compounds according to the invention. Column 2 of Table A shows $IC_{50}$ data from Test (a) for the inhibition of EGFR tyrosine kinase protein phosphorylation; column 3 shows $IC_{50}$ data from Test (a) for the inhibition of erbB2 tyrosine kinase protein phosphorylation; and column 4 shows $IC_{50}$ data for inhibition of proliferation of KB cells in test (b) described above:

TABLE A

| Example Number | $IC_{50}$ (nM) Test (a): Inhibition of EGFR tyrosine kinase protein phosphorylation | $IC_{50}$ (nM) Test (a): Inhibition of erbB2 tyrosine kinase protein phosphorylation | $IC_{50}$ (nM) Test (b): EGFR driven KB cell proliferation assay |
|---|---|---|---|
| 2 | 70 | 1852 | 141 |
| 3 | 9 | 275 | 91 |
| 4 | 39 | 252 | 138 |
| 6 | 57 | 1631 | 130 |
| 13 | 1 | 358 | 28 |
| 16 | 1 | 52 | 128 |
| 18 | 8 | 85 | 99 |
| 22 | 1 | 61 | 75 |
| 23 | 56 | 1727 | 288 |
| 25 | 32 | 1910 | 156 |
| 31 | 42 | 532 | 112 |
| 32 | 18 | 215 | 118 |

According to a further aspect of the invention there is provided a pharmaceutical composition which comprises a quinazoline derivative of the formula I, or a pharmaceutically-acceptable thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a quinazoline derivative of the formula I will naturally vary according to the nature and severity of the conditions, the age and sex of the animal or patient and the route of administration, according to well known principles of medicine.

In using a quinazoline derivative of the formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used.

Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

We have found that the compounds of the present invention possess anti-proliferative properties such as anti-cancer properties that are believed to arise from their erbB family receptor tyrosine kinase inhibitory activity, particularly inhibition of the EGF receptor (erbB1) tyrosine kinase. Furthermore, certain of the compounds according to the present invention possess substantially better potency against the EGF receptor tyrosine kinase, than against other tyrosine kinase enzymes, for example erbB2. Such compounds possess sufficient potency against the EGF receptor tyrosine kinase that they may be used in an amount sufficient to inhibit EGF receptor tyrosine kinase whilst demonstrating little, or significantly lower, activity against other tyrosine kinase enzymes such as erbB2. Such compounds are likely to be useful for the selective inhibition of EGF receptor tyrosine kinase and are likely to be useful for the effective treatment of, for example EGF driven tumours.

Accordingly, the compounds of the present invention are expected to be useful in the treatment of diseases or medical conditions mediated alone or in part by erbB receptor tyrosine kinases (especially EGF receptor tyrosine kinase), i.e. the compounds may be used to produce an erbB receptor tyrosine kinase inhibitory effect in a warm-blooded animal in need of such treatment. Thus the compounds of the present invention provide a method for the treatment of malignant cells characterised by inhibition of one or more of the erbB family of receptor tyrosine kinases. Particularly the compounds of the invention may be used to produce an anti-proliferative and/or pro-apoptotic and/or anti-invasive effect mediated alone or in part by the inhibition of erbB receptor tyrosine kinases. Particularly, the compounds of the present invention are expected to be useful in the prevention or treatment of those tumours that are sensitive to inhibition of one or more of the erbB receptor tyrosine kinases, such as EGF and/or erbB2 and/or erbB4 receptor tyrosine kinases (especially EGF receptor tyrosine kinase) that are involved in the signal transduction steps which drive proliferation and survival of these tumour cells. Accordingly the compounds of the present invention are expected to be useful in the treatment of psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval tumours. According to this aspect of the invention there is provided a quinazoline derivative of the formula I, or a pharmaceutically acceptable salt thereof, for use as a medicament.

According to a further aspect of the invention there is provided a compound of the formula I, or a pharmaceutically acceptable salt thereof, for use in the production of an anti-proliferative effect in a warm-blooded animal such as man.

Thus according to this aspect of the invention there is provided the use of a quinazoline derivative of the formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative of the formula I, or a pharmaceutically acceptable salt thereof, as hereinbefore defined.

According to a further aspect of the present invention there is provided the use of a quinazoline derivative of the formula I, or a pharmaceutically-acceptable salt thereof, as defined hereinbefore in the manufacture of a medicament for use in the treatment of a disease state or medical condition (for example a cancer as mentioned herein) mediated alone or in part by one or more erbB receptor tyrosine kinases (such as EGFR and/or erbB2 and/or erbB4, especially EGFR).

According to a further feature of this aspect of the invention there is provided a method for treating a disease or medical condition (for example a cancer as mentioned herein) mediated alone or in part by one or more erbB receptor tyrosine kinases (such as EGFR and/or erbB2 and/or erbB4, especially EGFR) in a warm-blooded animal, such as man, in need of such treatment, which comprises administering to said animal an effective amount of a quinazoline derivative of the formula I, or a pharmaceutically-acceptable salt thereof, as defined hereinbefore.

According to a further aspect of the invention there is provided a quinazoline derivative of the formula I, or a pharmaceutically acceptable salt thereof, for use in the treatment of a disease or medical condition (for example a cancer as mentioned herein) mediated alone or in part by one or more erbB receptor tyrosine kinases (such as EGFR and/or erbB2 and/or erbB4, especially EGFR).

According to a further aspect of the invention there is provided the use of a quinazoline derivative of the formula I, or a pharmaceutically-acceptable salt thereof, as defined hereinbefore in the manufacture of a medicament for use in the prevention or treatment of those tumours which are sensitive to inhibition of one or more of the erbB receptor tyrosine kinases, such as EGFR and/or erbB2 and/or erbB4 (especially EGFR), that are involved in the signal transduction steps which lead to the proliferation of tumour cells.

According to a further feature of this aspect of the invention there is provided a method for the prevention or treatment of those tumours which are sensitive to inhibition of one or more of the erbB family of receptor tyrosine kinases, such as EGFR and/or erbB2 and/or erbB4 (especially EGFR), that are involved in the signal transduction steps which lead to the proliferation and/or survival of tumour cells in a warm-blooded animal, such as man, in need of such treatment, which comprises administering to said animal an effective amount of a quinazoline derivative of the formula I, or a pharmaceutically-acceptable salt thereof, as defined hereinbefore.

According to a further feature of this aspect of the invention there is provided a compound of the formula I, or a pharmaceutically acceptable salt thereof, for use in the prevention or treatment of those tumours which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further aspect of the invention there is provided the use of a quinazoline derivative of the formula I, or a pharmaceutically-acceptable salt thereof, as defined hereinbefore in the manufacture of a medicament for use in providing a EGFR and/or erbB2 and/or erbB4 (especially a EGFR) tyrosine kinase inhibitory effect.

According to a further feature of this aspect of the invention there is provided a method of treatment for providing a EGFR and/or an erbB2 and or an erbB4 (especially a EGFR) tyrosine kinase inhibitory effect in a warm-blooded animal, such as man, in need of such treatment, which comprises administering to said animal an effective amount of a quinazoline derivative of the formula I, or a pharmaceutically-acceptable salt thereof, as defined hereinbefore.

According to a further feature of this aspect of the invention there is provided a compound of the formula I, or a pharmaceutically acceptable salt thereof, for use in providing a EGFR and/or erbB2 and/or erbB4 (especially a EGFR) tyrosine kinase inhibitory effect.

According to a further feature of the present invention there is provided the use of a quinazoline derivative of the formula I, or a pharmaceutically-acceptable salt thereof, as defined hereinbefore in the manufacture of a medicament for use in providing a selective EGFR tyrosine kinase inhibitory effect.

According to a further feature of this aspect of the invention there is provided a method of treatment for providing a selective EGFR tyrosine kinase inhibitory effect in a warm-blooded animal, such as man, in need of such treatment, which comprises administering to said animal an effective amount of a quinazoline derivative of the formula I, or a pharmaceutically-acceptable salt thereof, as defined hereinbefore.

According to a further feature of this aspect of the invention there is provided a compound of the formula I, or a pharmaceutically acceptable salt thereof, for use in providing a selective EGFR tyrosine kinase inhibitory effect.

By "a selective EGFR kinase inhibitory effect" is meant that the quinazoline derivative of formula I is more potent against EGF receptor tyrosine kinase than it is against other kinases. In particular some of the compounds according to the invention are more potent against EGF receptor kinase than it is against other tyrosine kinases such as other erbB receptor tyrosine kinases, particularly erbB2. Particularly a selective EGFR kinase inhibitor according to the invention is at least 5 times, preferably at least 10 times more potent against EGFR tyrosine kinase driven proliferation than it is against erbB2 receptor tyrosine kinase driven proliferation. The relative potency against EGFR and erbB2 may be determined by comparison of the relative $IC_{50}$ values obtained in suitable assays, such as an in-vitro cellular assay, for example by comparison of the $IC_{50}$ values obtained from the H16N-2 assay described above under heregulin 0 and EGF driven proliferative conditions. Alternatively by comparison of the $IC_{50}$ values from the KB cell proliferation assay (test (b) above) and the Clone 24 phospho-erbB2 cell assay (test (c) above).

According to a further aspect of the present invention there is provided the use of a quinazoline derivative of the formula I, or a pharmaceutically-acceptable salt thereof, as defined hereinbefore in the manufacture of a medicament for use in the treatment of a cancer, for example a cancer selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer.

According to a further feature of this aspect of the invention there is provided a method for treating a cancer, for example a cancer selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer in a warm-blooded animal, such as man, in need of such treatment, which comprises administering to said animal an effective amount of a quinazoline derivative of the formula I, or a pharmaceutically-acceptable salt thereof, as defined hereinbefore.

According to a further aspect of the invention there is provided a quinazoline derivative of the formula I, or a pharmaceutically acceptable salt thereof, for use in the treatment of a cancer, for example a cancer selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer.

As mentioned above the size of the dose required for the therapeutic or prophylactic treatment of a particular disease will necessarily be varied depending upon, amongst other things, the host treated, the route of administration and the severity of the illness being treated.

The anti-proliferative treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbB2 antibody trastuzumab [Herceptin™] and the anti-erbb1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as
N-(3-chloro-4-fluorophenyl)-7-methoxy-6-(3-morpholino propoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the formula I as defined hereinbefore and an additional anti-tumour agent as defined hereinbefore for the conjoint treatment of cancer.

Although the compounds of the formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

In the above pharmaceutical composition, process, method, use and medicament manufacture features of the present invention, the alternative and preferred embodiments of the compounds of the invention described herein also apply.

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulfate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by LC and/or analytical LC-MS, and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (NAB) or electrospray (ESP); values for m/z are given; generally, only ions which indicate the parent mass are reported; and unless otherwise stated, the mass ion quoted is $(MH)^+$ which refers to the protonated mass ion; reference to $M^+$ is to the mass ion generated by loss of an electron; and reference to $M-H^+$ is to the mass ion generated by loss of a proton;

(xi) unless stated otherwise compounds containing an asymmetrically substituted carbon and/or sulfur atom have not been resolved;

(xii) where a synthesis is described as being analogous to that described in a previous example the amounts used are the millimolar ratio equivalents to those used in the previous example;

(xiii) the following abbreviations have been used:
THF tetrahydrofuran;
DMF N,N-dimethylformamide;
DMA N,N-dimethylacetamide;
DCM dichloromethane;
DMSO dimethylsulfoxide;

IPA Isopropyl alcohol;
ether diethyl ether; and
HPLC high pressure liquid chromatography.

EXAMPLE 1

2-{(2S)-2-[({4-[3-Chloro-4-fluoroanilino]-7-methoxyquinazolin-5-yl}oxy)methyl]pyrrolidin-1-yl}-2-oxoethanol

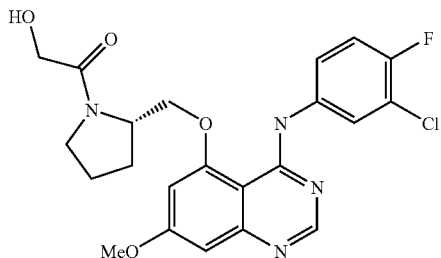

(Process (a))

Glycolic acid (20 mg) and O-(7-azabenzotriazol-1-yl)-N,N,N',N'-tetramethyluronium hexafluorophosphate (HATU, 109 mg) were added sequentially, each in one portion, to a stirred solution of N-(3-chloro-4-fluorophenyl)-7-methoxy-5-[(2S)-pyrrolidin-2-ylmethoxy]-quinazolin-4-amine (96 mg) and N,N-diisopropylethylamine (83 µl) in DCM (3 ml) at room temperature under a nitrogen atmosphere. The reaction mixture was stirred for 16 hours 30 minutes and then diluted with DCM (10 ml) and washed with saturated aqueous sodium hydrogen carbonate and water. The organic layer was dried (MgSO$_4$) and concentrated in vacuo to leave a yellow oil, which was purified by column chromatography using 0-10% methanol in dichloromethane as eluent to give the title compound as a white solid (55 mg, 50%); NMR Spectrum (DMSO-d6) 9.90 (s, 1H), 8.42 (s, 1H), 8.15 (dd, 1H), 7.70-7.60 (m, 1H), 7.40 (t, 1H), 6.88 (d, 1H), 6.78 (d, 1H), 4.65-4.53 (m, 2H), 4.40 (dd, 1H), 4.17 (dd, 1H), 4.03 (d, 1H), 3.90 (s, 3H), 3.45-3.35 (m, 3H), 2.10-1.82 (m, 4H); Mass spectrum MH$^+$ 461.

The N-(3-chloro-4-fluorophenyl)-7-methoxy-5-[(2S)-pyrrolidin-2-ylmethoxy]-quinazolin-4-amine used as starting material was prepared as follows:

DMF (12 ml) was added dropwise over 5 minutes to a slurry of 5,7-difluoroquinazolin-4(3H)-one (15 g) (obtained as described in WO01/94341 Example 4, foot note 5) in thionyl chloride (120 ml) at room temperature under a nitrogen atmosphere and the grey mixture was heated at 110° C. for 16 hours. The reaction mixture was cooled to room temperature and concentrated in vacuo. There was thus obtained 4-chloro-5,7-difluoro-quinazoline as a brown solid (16.5 g) which was used without further purification.

3-Chloro-4-fluoroaniline (12 g) and 1N HCl in dioxane (40 ml) were added sequentially, each in one portion, to a mixture of 4-chloro-5,7-difluoroquinazoline (16.5 g) in IPA (250 ml) and the mixture was stirred at 80° C. under a nitrogen atmosphere for 17 hours. The reaction mixture was cooled to 0° C. and the precipitated solid was filtered and dried to leave N-(3-chloro-4-fluorophenyl)-5,7-difluoroquinazolin-4-amine as a green solid (18.2 g, 71%); Mass spectrum MH$^+$ 310.

Methanol (6.5 ml) and potassium tert-butoxide (18 g) were added sequentially, each in one portion, to a mixture of N-(3-chloro-4-fluorophenyl)-5,7-difluoroquinazolin-4-amine (13.8 g) in THF (270 ml) at room temperature under a nitrogen atmosphere. The mixture was heated at 75° C. for 18 hours 30 minutes and then cooled to room temperature and concentrated in vacuo to leave a brown solid. The solid was cooled to 0° C. and cold water was added and then the precipitate was filtered and dried to leave N-(3-chloro-4-fluorophenyl)-5,7-dimethoxyquinazolin-4-amine as a light brown solid (10.4 g, 69%); Mass spectrum MH$^+$ 334.

Pyridine hydrochloride (2.33 g) was added in one portion to a stirred mixture of N-(3-chloro-4-fluorophenyl)-5,7-dimethoxyquinazolin-4-amine (6.4 g) in pyridine (75 ml) at room temperature. The reaction mixture was stirred at 115° C. under a nitrogen atmosphere for 23 hours and then the brown solution was cooled to room temperature and the yellow precipitate was filtered and washed with ice cold water to leave a light yellow solid. The solid was taken up in 7N ammonia in methanol and stirred at room temperature for 10 minutes. The solution was filtered and the filtrate was concentrated in vacuo to leave 4-[(3-chloro-4-fluorophenyl)-amino]-7-methoxyquinazolin-5-ol as a light brown solid (4.2 g, 68%); Mass spectrum MH$^+$ 320.

tert-Butyl (2S)-(−)-2-(hydroxymethyl)pyrrolidine-1-carboxylate (840 mg) and a solution of di-tert-butyl azodicarboxylate (1.32 g) in DCM (10 ml) were added sequentially, each in one portion, to a stirred mixture of 4-[(3-chloro-4-fluorophenyl)-amino]-7-methoxyquinazolin-5-ol (1.22 g) and triphenylphosphine (1.50 g) in DCM (50 ml) at 0° C. under a nitrogen atmosphere. The mixture was warmed to room temperature and stirred for 17 hours. The mixture was filtered, concentrated in vacuo, and purified by column chromatography using 0-10% methanol in DCM as eluent to give tert-butyl (2S)-2-[({4-[3-chloro-4-fluoro-anilino]-7-methoxyquinazolin-5-yl}oxy)methyl]pyrrolidine-1-carboxylate as a thick yellow oil (1.6 g, containing 6% triphenylphosphine oxide); Mass spectrum MH$^+$ 503.

Trifluoroacetic acid (25 ml) was added in one portion to tert-butyl (2S)-2-[({4-[3-chloro-4-fluoro-anilino]-7-methoxyquinazolin-5-yl}oxy)methyl]pyrrolidine-1-carboxylate (1.6 g) and the solution was stirred at room temperature for 1 hour 30 minutes. The solution was then concentrated in vacuo and azeotroped three times with ether to leave an orange oil. 7N Ammonia in methanol (5 ml) was added and the mixture was stirred for 10 minutes. The mixture was then concentrated in vacuo to leave an orange oil and purified by column chromatography using 0-10% methanol in DCM as eluent to give N-(3-chloro-4-fluorophenyl)-7-methoxy-5-[(2S)-pyrrolidin-2-ylmethoxy]-quinazolin-4-amine as a light yellow solid (1.15 g, 75% over two steps); Mass spectrum MH$^+$ 403.

EXAMPLE 2

N-(3-Chloro-4-fluorophenyl)-5-({(2S)-1-[(dimethylamino)acetyl]pyrrolidin-2-yl}methoxy)-7-methoxyquinazolin-4-amine (Process (a))

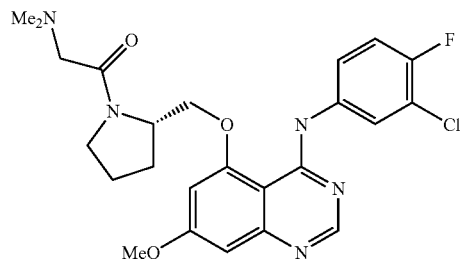

The procedure described in Example 1 was repeated using N-(3-chloro-4-fluoro-phenyl)-7-methoxy-5-[(2S)-pyrrolidin-2-ylmethoxy]-quinazolin-4-amine (96 mg) and N,N-dimethylglycine (27 mg) to give the title compound as a white solid in 73% yield; NMR Spectrum (DMSO-d6) 9.90 (s, 1H), 8.40 (s, 1H), 8.15 (dd, 1H), 7.72-7.62 (m, 1H), 7.40 (t, 1H), 6.88 (d, 1H), 6.78 (d, 1H), 4.66-4.58 (m, 1H), 4.40 (dd, 1H), 4.19 (dd, 1H), 3.90 (s, 3H), 3.66-3.40 (m, 2H), 3.20-3.06 (m, 2H), 2.40 (s, 6H), 2.10-1.82 (m, 4H); MH+ 488.

EXAMPLE 3

2-{(2R)-2-[({4-[3-Chloro-4-fluoroanilino]-7-methoxyquinazolin-5-yl}oxy)methyl]pyrrolidin-1-yl}-2-oxoethanol (Process (a))

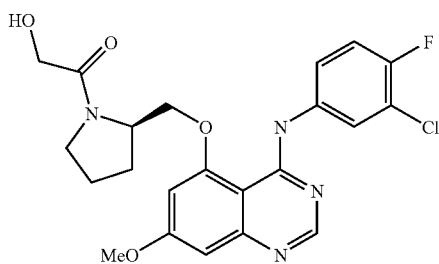

The procedure described in Example 1 was repeated using N-(3-chloro-4-fluorophenyl)-7-methoxy-5-[(2R)-pyrrolidin-2-ylmethoxy]-quinazolin-4-amine (90 mg) and glycolic acid (19 mg) to give the title compound in 47% yield; NMR Spectrum (DMSO-d6) 9.90 (s, 1H), 8.42 (s, 1H), 8.15 (dd, 1H), 7.70-7.60 (m, 1H), 7.40 (t, 1H), 6.90 (d, 1H), 6.78 (d, 1H), 4.65-4.53 (m, 2H), 4.42-4.37 (m, 1M), 4.20-4.11 (m, 1H), 4.03 (d, 1H), 3.90 (s, 3H), 3.45-3.35 (m, 3H), 2.10-1.82 (m, 41); Mass spectrum MH+ 461.

The N-(3-chloro-4-fluorophenyl)-7-methoxy-5-[(2R)-pyrrolidin-2-ylmethoxy]-quinazolin-4-amine used as starting material was prepared in 79% yield by reacting 4-[(3-chloro-4-fluorophenyl)-amino]-7-methoxy-quinazolin-5-ol (obtained as described in Example 1, preparation of starting materials) and tert-butyl (2R)-(+)-2-(hydroxymethyl)pyrrolidine-1-carboxylate using an analogous procedure to that described in the preparation of N-(3-chloro-4-fluorophenyl)-7-methoxy-5-[(2S)-pyrrolidin-2-ylmethoxy]-quinazolin-4-amine in Example 1; Mass spectrum MH+ 403.

EXAMPLE 4

N-(3-Chloro-4-fluorophenyl)-5-({(2R)-1-[dimethylamino)acetyl]pyrrolidin-2-yl}methoxy)-7-methoxyquinazolin-4-amine (Process (a))

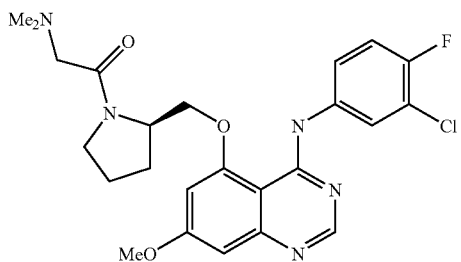

The procedure described in Example 1 was repeated using N-(3-chloro-4-fluorophenyl)-7-methoxy-5-[(2R)-pyrrolidin-2-ylmethoxy]-quinazolin-4-amine (90 mg) (obtained as described in Example 3, preparation of starting materials) and N,N-dimethylglycine (25 mg) to give the title compound as a white solid in 53% yield; NMR Spectrum (DMSO-d6) 9.90 (s, 1H), 8.40 (s, 1H), 8.15 (dd, 1H), 7.72-7.62 (m, 1H), 7.40 (t, 1H), 6.86 (d, 1H), 6.78 (d, 1H), 4.64-4.56 (m, 1H), 4.38 (dd, 1H), 4.18 (dd, 1H), 3.90 (s, 3H), 3.58-3.50 (m, 2H), 3.15 (q, 2H), 2.20 (s, 6H), 2.10-1.82 (m, 4H); Mass spectrum MH+ 488.

EXAMPLE 5

2-{3-[({4-[3-Chloro-4-fluoroanilino]-7-methoxyquinazolin-5-yl}oxy)methyl]pyrrolidin-1-yl}-2-oxoethanol (Process (a))

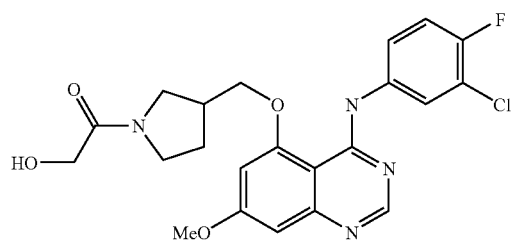

The procedure described in Example 1 was repeated using N-(3-chloro-4-fluoro-phenyl)-7-methoxy-5-(pyrrolidin-3-ylmethoxy)quinazolin-4-amine (100 mg) and glycolic acid (21 mg) to give the title product in 45% yield; NMR spectrum (DMSO-d6 at 373 K) 9.69 (s, 1H), 8.52 (s, 1H), 8.21-8.20 (m, 1H), 7.66-7.63 (m, 1H), 7.40 (t, 1H), 6.90 (d, 1H), 6.83 (d, 1H), 4.41-4.39 (m, 2H), 4.20-4.10 (m, 1H), 4.05-4.00 (m, 2H), 3.97 (s, 3H), 3.73 (dd, 1H), 3.61-3.58 (m, 1H), 3.51-3.47 (m, 1H), 3.42 (dd, 1H), 2.26-2.14 (br m, 1H), 2.00-1.87 (br m, 1H); Mass spectrum MH+ 461.

The N-(3-chloro-4-fluoro-phenyl)-7-methoxy-5-(pyrrolidin-3-ylmethoxy)quinazolin-4-amine used as starting material was prepared in 80% yield by reacting 4-[(3-chloro-4-fluorophenyl)-amino]-7-methoxy-quinazolin-5-ol (obtained as described in Example 1, preparation of starting materials) and tert-butyl 3-(hydroxymethyl)pyrrolidine-1-carboxylate using an analogous procedure to that described in the preparation of N-(3-chloro-4-fluorophenyl)-7-methoxy-5-[(2S)-pyrrolidin-2-ylmethoxy]-quinazolin-4-amine in Example 1; NMR spectrum (CDCl3) 9.83 (s, 1H, 8.56 (s, 1H), 7.89 (dd, 1H), 7.46-7.41 (m, 1H), 7.15 (t, 1H), 6.86 (d, 1H), 6.50 (d, 1H), 4.15-4.12 (m, 2H), 3.93 (s, 3H), 3.50 (s, 1H), 3.20 (dd, 1H), 3.10-3.02 (m, 1H), 3.00-2.91 (m, 2H), 2.82-2.76 (m, 1H), 2.17-2.05 (m, 1H), 1.77-1.65 (m, 1H); Mass spectrum MH+ 403.

EXAMPLE 6

N-(3-Chloro-4-fluorophenyl)-7-methoxy-5-{[(2S)-1-(pyrrolidin-1-ylacetyl)pyrrolidin-2-yl]methoxy}quinazolin-4-amine (Process (b))

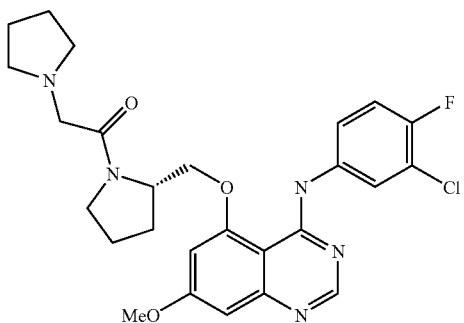

Chloroacetyl chloride (21 μl) was added in one portion to a stirred solution of N-(3-chloro-4-fluorophenyl)-7-methoxy-5-[(2S)-pyrrolidin-2-ylmethoxy]-quinazolin-4-amine (96 mg) (obtained as described in Example 1, preparation of starting materials) and N,N-diisopropylethylamine (83 μl) in DCM (3 ml) at room temperature. The reaction mixture was stirred for 40 minutes and then pyrrolidine (80 μl) was added in one portion and the reaction mixture was stirred for 15 hours 30 minutes under a nitrogen atmosphere. The reaction mixture was diluted with DCM (10 ml) and washed with saturated aqueous sodium hydrogen carbonate and water. The organic layer was dried (MgSO$_4$) and concentrated in vacuo to leave a yellow oil, which was purified by column chromatography using 0-10% methanol in DCM as eluent to give the title compound as a white solid (75 mg, 61%); NMR Spectrum (DMSO-d6) 9.90 (s, 1H), 8.40 (s, 1H), 8.10 (dd, 1H), 7.72-7.62 (m, 1), 7.39 (t, 1H), 6.82 (d, 1H), 6.78 (d, 1H), 4.62-4.54 (m, 1H), 4.34 (dd, 1H), 4.16 (dd, 1H), 3.90 (s, 3H), 3.58-3.48 (m, 2H), 3.28-3.16 (m, 2H), 2.48 (br s, 4H), 2.10-1.82 (m, 4H), 1.6 (br s, 4H); Mass spectrum MH$^+$ 514.

EXAMPLE 7

N-(3-Chloro-4-fluorophenyl)-7-methoxy-5-{[(2S)-1-(morpholin-4-ylacetyl)pyrrolidin-2-yl]methoxy}quinazolin-4-amine (Process (b))

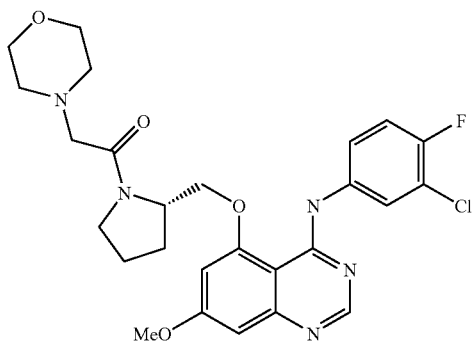

The procedure described in Example 6 was repeated using N-(3-chloro-4-fluoro-phenyl)-7-methoxy-5-[(2S)-pyrrolidin-2-ylmethoxy]-quinazolin-4-amine and morpholine to give the title compound as a white solid in 38% yield; NMR Spectrum (DMSO-d6) 9.90 (s, 1H), 8.40 (s, 1H), 8.10 (dd, 1H), 7.72-7.62 (m, 1), 7.39 (t, 1H), 6.82 (d, 1H), 6.78 (d, 1H), 4.62-4.54 (m, 1H), 4.34 (dd, 1H), 4.16 (dd, 1H), 3.90 (s, 3H), 3.58-3.50 (m, 2H), 3.50-3.42 (m, 4H), 3.10 (q, 2H), 2.40 (m, 4H), 2.08-1.82 (m, 4H); Mass spectrum MH$^+$ 530.

EXAMPLE 8

N-(3-Chloro-4-fluorophenyl)-7-methoxy-5-({(2S)-1-[(4-methylpiperazin-1-yl)acetyl]pyrrolidin-2-yl}methoxy)quinazolin-4-amine (Process (b))

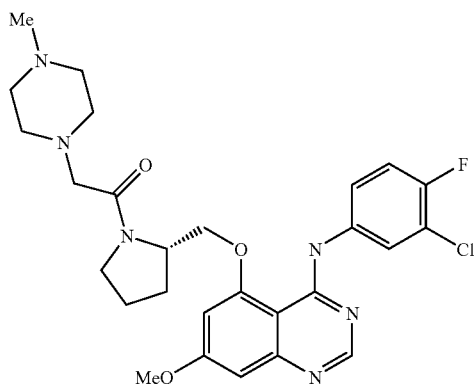

The procedure described in Example 6 was repeated using N-(3-chloro-4-fluoro-phenyl)-7-methoxy-5-[(2S)-pyrrolidin-2-ylmethoxy]-quinazolin-4-amine and N-methylpiperazine to give the title compound as a white solid in 36% yield; NMR Spectrum (DMSO-d6) 9.90 (s, 1H), 8.40 (s, 1H), 8.15 (dd, 1H), 7.72-7.62 (m, 1), 7.40 (t, 1H), 6.88 (d, 1H), 6.78 (d, 1H), 4.60-4.52 (m, 1H), 4.34 (dd, 1H), 4.16 (dd, 1H), 3.88 (s, 3H), 3.58-3.50 (m, 2H), 3.08 (q, 2H), 2.46-2.20 (m, 8H), 2.15 (s, 3H), 2.05-1.82 (m, 4H); Mass spectrum MH$^+$ 543.

EXAMPLE 9

(3S)-1-(2-{(2S)-2-[({4-[3-Chloro-4-fluoroanilino]-7-methoxyquinazolin-5-yl}oxy)methyl]pyrrolidin-1-yl}-2-oxoethyl)pyrrolidin-3-ol (Process (b))

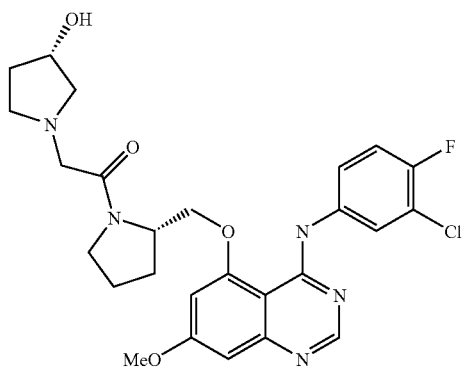

The procedure described in Example 6 was repeated using N-(3-chloro-4-fluoro-phenyl)-7-methoxy-5-[(2S)-pyrrolidin-2-ylmethoxy]-quinazolin-4-amine and (S)-3-pyrrolidinol to give the title compound as a white solid in 38% yield; Mass spectrum MH⁺ 530.

EXAMPLE 10

N-(3-Chloro-4-fluorophenyl)-7-methoxy-5-[((2S)-1-{[(2-methoxyethyl)(methyl)amino]-acetyl}pyrrolidin-2-yl)methoxy]quinazolin-4-amine

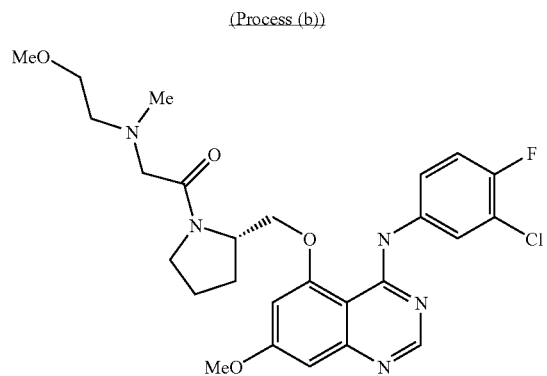

(Process (b))

The procedure described in Example 6 was repeated using N-(3-chloro-4-fluoro-phenyl)-7-methoxy-5-[(2S)-pyrrolidin-2-ylmethoxy]-quinazolin-4-amine and N-(2-methoxyethyl)methylamine to give the title compound as a white solid in 34% yield; NMR Spectrum (DMSO-d6) 9.90 (s, 1H), 8.40 (s, 1H), 8.10 (dd, 1H), 7.72-7.62 (m, 1H), 7.40 (t, 1H), 6.84 (d, 1H), 6.78 (d, 1H), 4.63-4.57 (m, 1H), 4.35 (dd, 1H), 4.15 (dd, 1H), 3.87 (s, 3H), 3.54 (t, 2), 3.32 (t, 2H), 3.30-3.15 (m, 2H), 3.15 (s, 3H), 2.56 (t, 2H), 2.20 (s, 3H), 2.04-1.82 (m, 4H); Mass spectrum MH⁺ 532.

EXAMPLE 11

N-(3-Chloro-4-fluorophenyl)-7-methoxy-5-[((2S)-1-{[(2-hydroxyethyl)(methyl)amino]-acetyl}pyrrolidin-2-yl)methoxy]quinazolin-4-amine

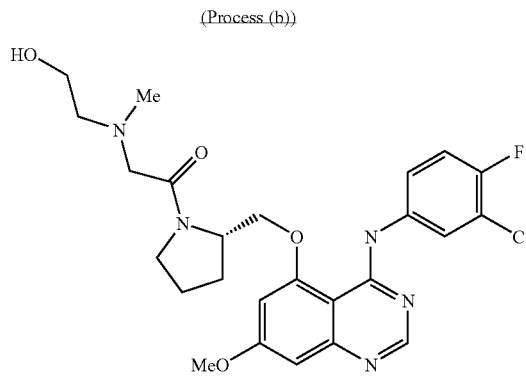

(Process (b))

The procedure described in Example 6 was repeated using N-(3-chloro-4-fluoro-phenyl)-7-methoxy-5-[(2S)-pyrrolidin-2-ylmethoxy]-quinazolin-4-amine and 2-(methylamino) ethanol to give the title compound as a white solid in 39% yield; NMR Spectrum (DMSO-d6) 9.90 (s, 1H), 8.40 (s, 1H), 8.13 (dd, 1H), 7.70-7.62 (m, 1H), 7.40 (t, 1H), 6.85-6.77 (m, 2H), 4.62-4.54 (m, 1H), 4.40-4.28 (m, 2H), 4.14 (dd, 1H), 3.90 (s, 3H), 3.55 (t, 2H), 3.44-3.37 (m, 2H), 3.24-3.10 (m, 2H), 2.54-2.40 (m, 2H), 2.20 (s, 3H), 2.10-1.82 (m, 4H); Mass spectrum MH⁺ 518.

EXAMPLE 12

N-(3-Chloro-4-fluorophenyl)-7-methoxy-5-{[(2R)-1-(methoxyacetyl)pyrrolidin-2-yl]methoxy}quinazolin-4-amine

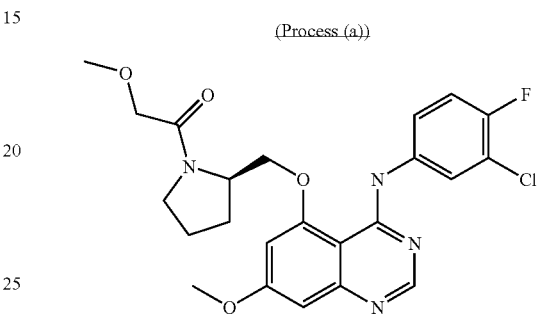

(Process (a))

Methoxyacetic acid (27 mg) and 4-(4,6-dimethoxy[1.3.5]triazin-2-yl)-4-methylmorpholinium chloride hydrate (103 mg) were added sequentially, each in one portion, to a stirred mixture of N-(3-chloro-4-fluorophenyl)-7-methoxy-5-[(2R)-pyrrolidin-2-ylmethoxy]-quinazolin-4-amine (100 mg) in DCM (2 ml) at room temperature. The reaction mixture was stirred for 1 hour and then diluted with DCM (10 ml) and washed with saturated aqueous sodium hydrogen carbonate. The organic layer was dried (MgSO₄) and concentrated in vacuo to leave a yellow solid, which was triturated with 1:1 ether/hexanes and filtered to give the title compound as a white solid (97 mg, 82%); NMR Spectrum (DMSO-d6) 9.90 (br s, 1H), 8.40 (s, 1H), 8.15 (m, 1H), 7.65 (m, 1H), 7.40 (m, 1H), 6.80 (m, 2H), 4.60 (m, 1H), 4.50 (m, 1H), 4.25 (m, 1H), 4.0 (m, 3H), 3.95 (s, 3H), 3.50 (m, 2l), 3.20 (m, 2H), 2.0-1.85 (m, 4H); Mass spectrum MH⁺ 475.

The N-(3-chloro-4-fluorophenyl)-7-methoxy-5-[(2R)-pyrrolidin-2-ylmethoxy]-quinazolin-4-amine used as starting material was prepared as described in Example 3.

EXAMPLE 13

5-{[(2R)-1-Acetylpyrrolidin-2-yl]methoxy}-N-(3-chloro-4-fluorophenyl)-7-methoxyquinazolin-4-amine

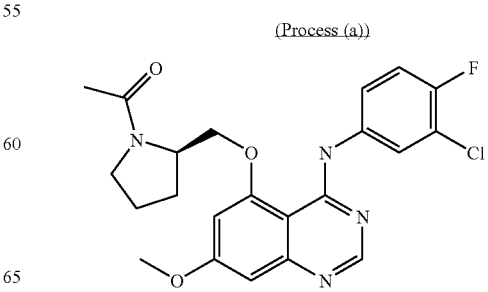

(Process (a))

N,N-Diisopropylethylamine (52 μl) and acetyl chloride (21 μl) were added sequentially, each in one portion, to a stirred mixture of N-(3-chloro-4-fluorophenyl)-7-methoxy-5-[(2R)-pyrrolidin-2-ylmethoxy]-quinazolin-4-amine (100 mg) in DCM (2 ml) at room temperature. The reaction mixture was stirred for 1 hour and then diluted with DCM (10 ml) and washed with saturated aqueous sodium hydrogen carbonate. The organic layer was dried (MgSO$_4$) and concentrated in vacuo to leave a yellow solid, which was purified by column chromatography using 24% methanol in DCM as eluent, followed by trituration with ether to give the title compound as a white solid (92 mg, 83%); NMR Spectrum (DMSO-d6) 9.90 (br s, 1H), 8.40 (s, 1H), 8.15 (m, 1H), 7.65 (m, 1H), 7.40 (m, 1H), 6.80 (m, 2H), 4.60 (m, 1H), 4.50 (m, 1H), 4.25 (m, 1H), 3.95 (s, 3H), 3.50 (m, 1H), 3.30 (s, 3H), 2.0-1.85 (m, 5H); Mass spectrum MH$^+$ 445.

The N-(3-chloro-4-fluorophenyl)-7-methoxy-5-[(2R)-pyrrolidin-2-ylmethoxy]-quinazolin-4-amine used as starting material was prepared as described in Example 3.

EXAMPLE 14

N-(3-Chloro-4-fluorophenyl)-7-methoxy-5-{[(2R)-1-(morpholin-4-ylacetyl)pyrrolidin-2-yl]methoxy}quinazolin-4-amine (Process (b))

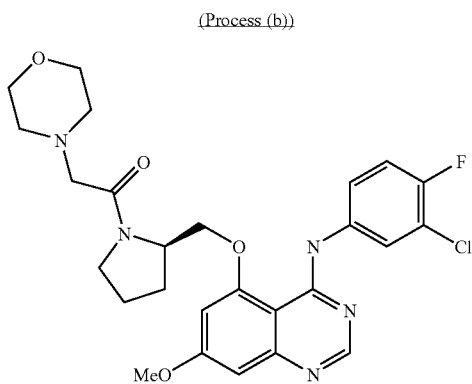

Chloroacetyl chloride (77 μl) was added in one portion to a stirred solution of N-(3-chloro(fluorophenyl)-7-methoxy-5-[(2R)-pyrrolidin-2-ylmethoxy]-quinazolin-4-amine (300 mg) and N,N-diisopropylethylamine (168 μl) in DCM (4 ml) at room temperature. The reaction mixture was stirred for 1 hour and then was split into two equal portions. Morpholine (2 ml) was added to one portion and the reaction mixture was stirred at room temperature for 2 hours. The reaction mixture was diluted with DCM (10 ml) and washed with saturated aqueous sodium hydrogen carbonate. The organic layer was dried (MgSO$_4$) and concentrated in vacuo to leave a yellow oil, which was purified by column chromatography using 2-10% methanol in DCM with 1% 7 N ammonia in methanol as eluent to give the title compound as a white solid (142 mg, 72%); NMR Spectrum (DMSO-d6 at 373 K) 9.80 (br s, 1H), 8.40 (s, 1H), 8.15 (m, 1H), 7.65 (m, 1H), 7.33 (m, 1H), 6.80 (m, 2H), 4.60 (m, 1H), 4.50 (m, 1H), 4.25 (m, 1H), 3.95 (s, 3H), 3.60-3.45 (m, 6H), 3.20-3.0 (m, 2H), 2.40 (m, 4H), 2.10-1.85 (m, 4H); Mass spectrum MH$^+$ 530.

The N-(3-chloro-4-fluorophenyl)-7-methoxy-5-[(2R)-pyrrolidin-2-ylmethoxy]-quinazolin-4-amine used as starting material was prepared as described in Example 3.

EXAMPLE 15

N-(3-Chloro-4-fluorophenyl)-7-methoxy-5-({(2R)-1-[(4-methylpiperazin-1-yl)acetyl]pyrrolidin-2-yl}methoxy)quinazolin-4-amine (Process (b))

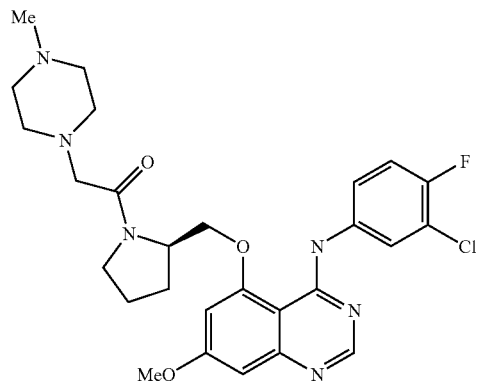

The procedure described in Example 14 was repeated using N-(3-chloro-4-fluoro-phenyl)-7-methoxy-5-[(2R)-pyrrolidin-2-ylmethoxy]-quinazolin-4-amine and 4-methylpiperazine to give the title compound as a white solid in 88% yield; NMR Spectrum (DMSO-d6 at 373 K); 9.80 (br s, 1H), 8.40 (s, 1H), 8.15 (m, 1H), 7.65 (m, 1H), 7.33 (m, 1H), 6.80 (m, 2H), 4.60 (m, 1H), 4.50 (m, 1H), 4.25 (m, 1H), 3.95 (s, 3H), 3.70 (m, 1H), 3.50 (m, 1H), 3.20-3.0 (m, 2H), 2.45 (m, 4H), 2.25 (m, 41), 2.10 (m, 3H), 2.0-1.85 (m, 4); Mass spectrum MH$^+$ 543.

EXAMPLE 16

2-[(2R)-2-({[4-[3-Chloro-4-fluoroanilino]-7-(2-hydroxyethoxy)quinazolin-5-yl]oxy}methyl)pyrrolidin-1-yl]-2-oxoethanol (Process (d))

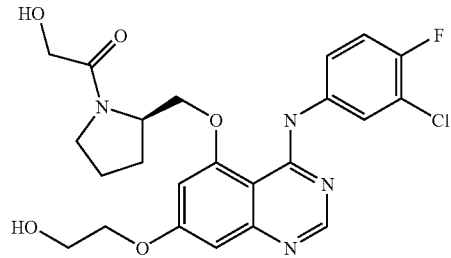

2-Bromoethanol (51 μl) and potassium carbonate (86 mg) were added to a mixture of 4-[3-chloro-4-fluoroanilino]-5-{[(2R)-1-glycoloylpyrrolidin-2-yl]methoxy}-quinazolin-7-ol (70 mg) in DMF and the reaction mixture was heated at 70° C. for 16 hours. The reaction mixture was cooled to room temperature and then water (5 ml) was added to leave a white precipitate. The precipitate was filtered, washed with water and then purified by column chromatography using 2-5% methanol in DCM as eluent. The product was purified further by acidic reverse phase HPLC, and then the combined fractions were reduced to a third of the initial concentration, basified with sodium carbonate and extracted with ethyl acetate. The organic layer was dried (Na$_2$SO$_4$) and concentrated in vacuo to give the title compound as a white solid (35 mg, 45%); NMR Spectrum (DMSO-d6 at 373 K) 9.80 (br s, 1H), 8.40 (s, 1H), 8.15 (m, 1H), 7.65 (m, 1M, 7.33 (m, 1H), 6.80 (m, 2H), 4.60 (m, 1H), 4.50 (m, 1H), 4.30-4.10 (m, 4H), 4.0 (m, 2H), 3.75 (m, 2H), 3.60 (m, 1H), 3.50-3.37 (m, 2H), 2.10-1.85 (m, 4H); Mass spectrum MH$^+$ 491.

The 4-[3-chloro-4-fluoroanilino]-5-{[(2R)-1-glycoloylpyrrolidin-2-yl]-methoxy}-quinazolin-7-ol used as starting material was prepared as follows:

Di-tert-butyl azodicarboxylate (11.0 g) was added portionwise, over 5 minutes, to a stirred solution of [7-(benzyloxy)-5-hydroxy-4-oxoquinazolin-3(4H)-yl]methyl pivalate (12.2 g) (obtained as described in WO01/94341 Example 15, foot note [8]), tert-butyl (2R)-(−)-2-(hydroxymethyl)pyrrolidine-1-carboxylate (7.4 g) and triphenylphosphine (11.7 g) in DCM (100 ml) at 0° C. under a nitrogen atmosphere. The mixture was warmed to room temperature and stirred for 16 hours. The mixture was concentrated in vacuo to leave the crude tert-butyl (2R)-2-{[(7-(benzyloxy)-3-{[(2,2-dimethylpropanoyl)oxy]methyl}-4-oxo-3,4-dihydroquinazolin-5-yl)oxy]methyl}pyrrolidine-1-carboxylate, which was used without further purification; Mass spectrum MH$^+$ 566.

The crude tert-butyl (2R)-2-{[(7-(benzyloxy)-3-{[(2,2-dimethylpropanoyl)oxy]-methyl}4-oxo-3,4-dihydroquinazolin-5-yl)oxy]methyl}pyrrolidine-1-carboxylate (assumed 18 g) was dissolved in 7N ammonia in methanol and stirred at room temperature for 16 hours. The reaction mixture was concentrated in vacuo and purified by column chromatography using 0-10% methanol in DCM as eluent to give a mixture of two products. The mixture was dissolved in DCM, washed with 20% aqueous sodium hydroxide solution (2x) and then dried (MgSO$_4$) and concentrated in vacuo to leave tert-butyl (2R)-2-({[7-(benzyloxy)-4-oxo-3,4-dihydroquinazolin-5-yl]oxy}methyl)pyrrolidine-1-carboxylate as a beige foam (6.8 g, 48% for the two steps); Mass spectrum MH$^+$ 452.

Phosphorous oxychloride (520 µl) was added dropwise to a mixture of tert-butyl (2R)-2-({[7-(benzyloxy)-4-oxo-3,4-dihydroquinazolin-5-yl]oxy}methyl)pyrrolidine-1-carboxylate (500 mg) and N,N-diisopropylethylamine (52 µl) in DCM (10 ml) and the reaction mixture was heated at 50° C. for 62 hours. The reaction mixture was concentrated in vacuo and then water and saturated aqueous sodium carbonate (cooled to 4° C.) was added. The aqueous mixture was then extracted with DCM and the organic layer was dried (MgSO$_4$) and concentrated in vacuo to leave tert-butyl (2R)-2-({[7-(benzyloxy)-4-chloroquinazolin-5-yl]oxy}methyl) pyrrolidine-1-carboxylate as a brown oil, which was used without further purification.

The crude tert-butyl (2R)-2-({[7-(benzyloxy)-4-chloroquinazolin-5-yl]oxy}methyl)-pyrrolidine-1-carboxylate was taken up in THF (5 ml) and 3-chloro-4-fluoroaniline (160 mg) and N,N-diisopropylethylamine (580 µl) were each added in one portion and the solution was heated at 70° C. for 18 hours. The reaction mixture was cooled to room temperature and concentrated in vacuo to leave a thick brown oil. Purification by flash chromatography, using 1.5% methanol in DCM as eluent, gave the tert-butyl (2R)-2-[({7-(benzyloxy)-4-[3-chloro-4-fluoroanilino]quinazolin-5-yl}oxy)methyl]pyrrolidine-1-carboxylate as a beige foam (350 mg, 54% over 2 steps); Mass spectrum MH$^+$ 481.

tert-Butyl (2R)-2-[({7-(benzyloxy)-4-[3-chloro-4-fluoroanilino]quinazolin-5-yl}oxy)methyl]pyrrolidine-1-carboxylate (1.5 g) was taken up in trifluoroacetic acid (15 ml) and the solution was heated at 70° C. for 18 hours. The solution was cooled to room temperature and then concentrated in vacuo to leave a brown residue. Saturated aqueous sodium hydrogen carbonate was added to the residue and the aqueous mixture was extracted with ethyl acetate. The layers were separated and the organic layer was dried (MgSO$_4$) and concentrated in vacuo to leave a brown oil. Purification by flash chromatography, using 5:1:84 methanol:7N ammonia in methanol:DCM→20:1:79 methanol:7N ammonia in methanol:DCM as eluent, followed by trituration with ether gave 4-[3-chloro-4-fluoro-anilino]-5-[(2R)-pyrrolidin-2-yl-methoxy]quinazolin-7-ol as an off-white solid (200 mg, 20%); NMR Spectrum (DMSO-d6) 10.40 (brs, 1H), 8.40 (s, 1H), 8.15 (m, 1H), 7.95 (m, 1H), 7.40 (m, 1H), 6.75 (m, 2H), 4.30 (m, 1H), 4.05 (m, 1H), 3.60-3.50 (m, 1H), 3.0-2.80 (m, 2H), 1.95-1.80 (m, 1H), 1.75-1.65 (m, 2H), 1.50-1.40 (m, 1H); Mass spectrum MH$^+$ 391.

Glycolic acid (50 mg) and O-(7-azabenzotriazol-1-yl)-N,N,N',N'-tetramethyluronium hexafluorophosphate (HATU, 250 mg) were added sequentially, each in one portion, to a stirred solution of 4-[3-chloro-4-fluoro-anilino]-5-[(2R)-pyrrolidin-2-ylmethoxy]quinazolin-7-ol (197 mg) and N,N-diisopropylethylamine (177 µl) in DCM (4 ml) at room temperature. The reaction mixture was stirred for 60 hours and then an additional portion of glycolic acid (20 mg) and O-(7-azabenzotriazol-1-yl)-N,N,N',N'-tetramethyluronium hexafluorophosphate (HATU, 100 mg) were added and the mixture was stirred for a further 5 hours. The reaction mixture was then diluted with DCM (10 ml) and washed with saturated aqueous sodium hydrogen carbonate. The organic layer was dried (MgSO$_4$) and concentrated in vacuo to leave a yellow oil, which was purified by column chromatography using 5% methanol in DCM as eluent to give the 4-[3-chloro-4-fluoro-anilino]-5-{[(2R)-1-glycoloylpyrrolidin-2-yl]-methoxy}-quinazolin-7-ol as a grey solid (96 mg, 42%); NMR Spectrum (DMSO-d6 at 373 K) 10.10 (brs, 1H), 9.60 (brs, 1H), 8.40 (s, 1H), 8.15 (m, 1H), 7.65 (m, 1H), 7.40 (m, 1H), 6.70 (s, 2H), 4.60 (m, 1H), 4.40 (m, 1H), 4.20 (m, 1H), 4.05 (m, 2H), 3.55-3.40 (m, 2H), 2.15-1.85 (m, 4H); Mass spectrum MH$^+$ 449.

EXAMPLE 17

2-[(2R)-2-({[4-[3-Chloro-4-fluoroanilino]-7-(2-methoxyethoxy)quinazolin-5-yl]oxy}methyl)pyrrolidin-1-yl]-2-oxoethanol

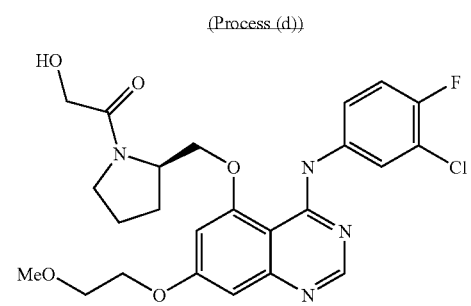

2-Bromoethyl methyl ether (22 μl) and potassium carbonate (43 mg) were added to a mixture of 4-[3-chloro-4-fluoroanilino]-5-{[(2R)-1-glycoloylpyrrolidin-2-yl]-methoxy}-quinazolin-7-ol (70 mg) in DMF and the reaction mixture was heated at 40° C. for 16 hours. The reaction mixture was cooled to room temperature and then water (5 ml) was added to leave a white precipitate. The precipitate was filtered, washed with water and then purified by column chromatography using 2-5% methanol in DCM as eluent to give the title compound as a white solid (51 mg, 64%); NMR Spectrum (DMSO-d6 at 373 K) 9.80 (br s, 1H), 8.40 (s, 1H), 8.15 (m, 1H), 7.65 (m, 1H), 7.33 (m, 1H), 6.80 (m, 2H), 4.60 (m, 1H), 4.50 (m, 1H), 4.30-4.10 (m, 4H), 4.0 (m, 2H), 3.75 (t, 2H), 3.50-3.37 (m, 2H), 3.35 (s, 3H), 2.10-1.85 (m, 4H); Mass spectrum MH+ 505.

The 4-[3-chloro-4-fluoroanilino]-5-{[(2R)-1-glycoloylpyrrolidin-2-yl]-methoxy}-quinazolin-7-ol used as starting material was prepared as described in Example 16.

EXAMPLE 18

2-[(2R)-2-({[4-[3-Chloro-4-fluoroanilino]-7-(2-ethoxyethoxy)quinazolin-5-yl]oxy}methyl)pyrrolidin-1-yl]-2-oxoethanol (Process (d))

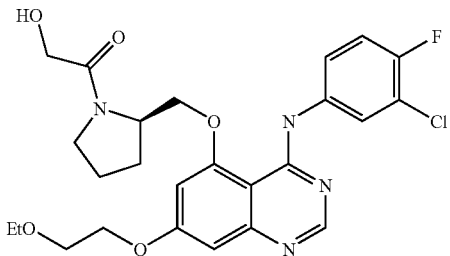

The procedure described in Example 17 was repeated using 4-[3-chloro-4-fluoro-anilino]-5-{[(2R)-1-glycoloylpyrrolidin-2-yl]-methoxy}-quinazolin-7-ol (70 mg) and 2-bromoethyl ethyl ether (26 μl) to give the title compound as a white solid in 48% yield; NMR Spectrum (DMSO-d6 at 373 K) 9.80 (br s, 1H), 8.40 (s, 1H), 8.15 (m, 1H), 7.65 (m, 1H), 7.33 (m, 1H), 6.80 (m, 2H), 4.60 (m, 1H), 4.50 (m, 1H), 4.30-4.10 (m, 4H), 4.0 (m, 2H), 3.75 (t, 2H), 3.55 (q, 2H), 3.48-3.37 (m, 2H), 2.10-1.85 (m, 4H), 1.15 (t, 3H); Mass spectrum MH+ 519.

EXAMPLE 19

2-{(2R)-2-[({4-[3-Chloro-4-fluoroanilino]-7-ethoxyquinazolin-5-yl}oxy)methyl]-pyrrolidin-1-yl}-2-oxoethanol (Process (a))

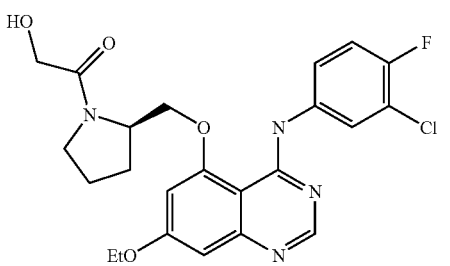

Glycolic acid (22 mg) and O-(7-azabenzotriazol-1-yl)-N,N,N',N'-tetramethyluronium hexafluorophosphate (HATU, 110 mg) were added sequentially, each in one portion, to a stirred solution of N-(3-chloro-4-fluorophenyl)-7-ethoxy-5-[(2R)-pyrrolidin-2-ylmethoxy]-quinazolin-4-amine (81 mg) and N,N-diisopropylethylamine (68 μl) in DCM (2.5 ml) at room temperature. The reaction mixture was stirred for 16 hours and then concentrated in vacuo to leave a brown residue. The residue was taken up in a 7:2:1 mixture of DMSO: acetonitrile:water, filtered and then purified by reverse phase HPLC. The fractions containing the required product were combined, basified by the addition of potassium carbonate and then extracted with DCM. The organic layer was dried (MgSO4) and then concentrated in vacuo to give the title compound as a white solid (36 mg, 39%); NMR Spectrum (DMSO-d6 at 373 K) 9.80 (br s, 1H), 8.40 (s, 1H), 8.15 (m, 1H), 7.65 (m, 1H), 7.33 (m, 1H), 6.80 (m, 2H), 4.60 (m, 1H), 4.50 (m, 1H), 4.30-4.10 (m, 4H), 4.0 (m, 2H), 3.50-3.40 (m, 2H), 2.10-1.85 (m, 4H), 1.40 (t, 3H); Mass spectrum MH+ 475.

The N-(3-chloro-4-fluorophenyl)-7-ethoxy-5-[(2R)-pyrrolidin-2-ylmethoxy]-quinazolin-4-amine used as starting material was prepared as follows:

A mixture of tert-butyl (2R)-2-[({7-(benzyloxy)-4-[3-chloro-4-fluoroanilino]-quinazolin-5-yl}oxy)methyl]pyrrolidine-1-carboxylate (230 mg) (obtained as described in Example 16) and 5% palladium on carbon in ethanol (5 ml) was stirred under hydrogen (5 bar pressure) at 25° C. for 16 hours. The mixture was then filtered and concentrated in vacuo to leave the tert-butyl (2R)-2-[({4-[3-chloro-4-fluoroanilino]-7-hydroxyquinazolin-5-yl}oxy)methyl]pyrrolidine-1-carboxylate as a light brown oil, which was used without further purification.

The crude tert-butyl (2R)-2-[({4-[3-chloro-4-fluoroanilino]-7-hydroxy-quinazolin-5-yl}oxy)methyl]pyrrolidine-1-carboxylate (120 mg) was dissolved in DMA (1 ml), and bromoethane (27 μl) and potassium carbonate (68 mg) were each added in one portion. The reaction mixture was heated at 40° C. for 16 hours and then cooled to room temperature. Trifluoroacetic acid (0.5 ml) was then added and the reaction mixture was stirred for 4 hours at room temperature. Further trifluoroacetic acid (1 ml) was added and the reaction mixture was stirred at room temperature for 16 hours. The reaction mixture was then poured onto saturated aqueous sodium hydrogen carbonate and then extracted with ethyl acetate. The organic layer was dried (MgSO4) and then concentrated in vacuo to leave a green oil. Purification by flash chromatography, using 2-5% methanol in DCM as eluent, gave the N-(3-chloro-4-fluorophenyl)-7-ethoxy-5-[(2R)-pyrrolidin-2-ylmethoxy]quinazolin-4-amine as a pale green solid (83 mg, 52% over three steps); NMR Spectrum (DMSO-d6) 10.2 (s, 1H), 9.50 (s, 1H), 8.30-8.20 (m, 1H), 7.90-7.80 (m, 1H), 7.50-7.40 (m, 1H), 6.80-6.70 (m, 1H), 4.50-4.40 (m, 1H), 4.30-4.20 (m, 1H), 4.30-4.10 (m, 3H), 3.90-3.80 (m, 1H), 3.15-3.05 (m, 2H), 2.10-2.00 (m, 1H), 1.90-1.80 (m, 2H), 1.70-1.60 (m, 1H), 1.40 (t, 3H); Mass spectrum MH+ 417.

EXAMPLE 20

(3S,5R)-5-[({4-[3-Chloro-4-fluoroanilino]-7-methoxyquinazolin-5-yl}oxy)methyl]-1-glycoloylpyrrolidin-3-ol

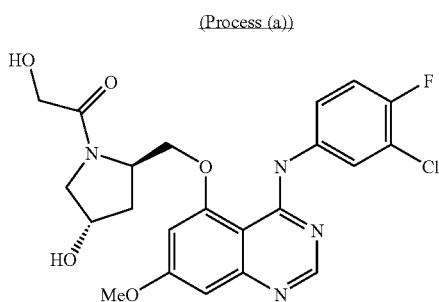

(Process (a))

O-(7-Azabenzotriazol-1-yl)-N,N,N',N'-tetramethyluronium hexafluorophosphate (HATU, 171 mg) was added in one portion to a stirred solution of (3S,5R)-5-[({4-[3-chloro-4-fluoroanilino]-7-methoxyquinazolin-5-yl}oxy)methyl] pyrrolidin-3-ol (157 mg), N,N-diisopropylethylamine (131 µl) and glycolic acid (31 µl) in DCM (5 ml), under an atmosphere of nitrogen. The reaction mixture was stirred at room temperature for 4 hours and then diluted with DCM and saturated aqueous sodium hydrogen carbonate was added. The organic layer was separated, dried ($Na_2SO_4$) and then concentrated in vacuo to leave the crude product as a yellow waxy solid. Purification by column chromatography, using 0 to 10% methanol in DCM as eluent, gave the title compound as a white solid (144 mg, 80%); NMR spectrum (DMSO-d6) 10.17 (s, 1H), 8.53 (s, 1H), 8.14 (dd, 1H), 7.74-7.69 (m, 1H), 7.47 (t, 1H), 6.92 (d, 1H), 6.83 (d, 1H), 5.14-5.10 (m, 1H), 4.71-4.67 (m, 1H), 4.50-4.44 (m, 1H), 4.40-4.38 (m, 1H), 4.28-4.23 (m, 1H), 4.06-4.03 (m, 2H), 3.95 (s, 3H), 3.53-3.48 (m, 2H), 2.05-2.02 (m, 2H); Mass spectrum $MH^+$ 477.

The (3S,5R)-5-[({4-[3-chloro-4-fluoroanilino]-7-methoxyquinazolin-5-yl}oxy)methyl]pyrrolidin-3-ol used as starting material was prepared as follows:

Di-tert-butylazodicarboxylate (DTAD, 623 mg) was added in one portion to a mixture of 4-[(3-chloro-4-fluorophenyl)-amino]-7-methoxy-quinazolin-5-ol (578 mg, prepared as described in Example 1, preparation of starting materials), tert-butyl (2R,4S)-4-{[tert-butyl(dimethyl)silyl]oxy}-2-(hydroxymethyl)pyrrolidine-1-carboxylate (750 mg), and triphenylphosphine (710 mg) in DCM (100 ml) at room temperature, under an atmosphere of nitrogen. The reaction mixture was stirred at room temperature for 24 hours and then concentrated in vacuo to leave a brown oil. Purification by column chromatography, using 0-50% ethyl acetate in hexane as eluent, gave tert-butyl (2R,4S)-4-{[tert-butyl-(dimethyl)silyl]-oxy}-2-[({4-[3-chloro-4-fluoroanilino]-7-methoxyquinazolin-5-yl}oxy)methyl]-pyrrolidine-1-carboxylate as a white solid (671 mg, 59%); NMR spectrum (DMSO-d6) 8.46 (s, 1H), 8.03 (br s, 1H), 7.67 (br s, 1H), 7.43 (t, 1H), 6.85-6.81 (m, 2H), 4.57-4.20 (m, 4H), 3.94 (s, 3H), 3.47-3.40 (m, 2H), 2.10-2.00 (m, 2H), 1.33 (m, 10H), 0.86 (s, 9H), 0.07 (s, 6H); Mass Spectrum $MH^+$ 633.

tert-Butyl (2R,4S)-4-{[tert-butyl(dimethyl)silyl]oxy}-2-[({4-[3-chloro-4-fluoro-anilino]-7-methoxyquinazolin-5-yl}oxy)methyl]pyrrolidine-1-carboxylate (636 mg) was dissolved in trifluoroacetic acid (30 ml) and stirred at room temperature for 72 hours. The reaction mixture was then concentrated in vacuo, and excess water was added, followed by the careful addition of saturated aqueous sodium hydrogen carbonate. The mixture was extracted with 3% methanol in DCM and the organic layer was separated, dried ($Na_2SO_4$) and concentrated in vacuo to leave a light brown foam. Trituration with cold acetonitrile gave (3S,5R)-5-[({4-[3-chloro-4-fluoroanilino]-7-methoxy-quinazolin-5-yl}oxy)methyl]-pyrrol 3-ol as an off-white solid (370 mg, 88%); NMR spectrum (DMSO-d6) 10.50-10.00 (br, 1H), 8.49 (s, 1M), 8.25 (dd, 1H), 7.90-7.84 (m, 1H), 7.44 (t, 1H), 6.82 (d, 1H), 6.76 (d, 1H), 4.92 (br s, 1H), 4.38 (dd, 1H), 4.32 (br s, 1H), 3.92-3.86 (m, 4H), 3.77-3.23 (br s, 1H), 3.09 (dd, 1H), 2.83 (d, 1H), 1.88 (dd, 1H), 1.74-1.65 (m, 1H); Mass spectrum $MH^+$ 419.

The tert-butyl (2R,4S)-4-{[tert-butyl(dimethyl)silyl]oxy}-2-(hydroxymethyl)-pyrrolidine-1-carboxylate used as starting material was prepared as follows:

(Trimethylsilyl)diazomethane (2N solution in hexane, 2.9 ml) was added dropwise over 5 minutes to a stirred solution of (4S)-1-(tert-butoxycarbonyl)-4-hydroxy-D-proline (1.0 g) in DCM (20 ml) and methanol (5 ml) at room temperature until a permanent faint yellow colour persisted. The reaction mixture was concentrated in vacuo and purified by column chromatography, using 0-50% ethyl acetate in hexane as eluent, to give 1-tert-butyl 2-methyl (2R,4S)-4-hydroxypyrrolidine-1,2-dicarboxylate as a clear oil (1.03 g, 97%); NMR spectrum ($CDCl_3$) 4.90-4.37 (m, 2H), 3.73 (s, 3H), 3.64 (dd, 1H), 3.53-3.43 (m, 1H), 2.34-2.27 (m, 1H), 2.12-1.97 (m, 2H), 1.46 (s, 3H), 1.41 (s, 6H).

tert-Butyldimethylsilyl triflate (1.44 ml) was added to a stirred solution of 1-tert-butyl 2-methyl (2R,4S)-4-hydroxy-pyrrolidine-1,2-dicarboxylate (1.03 g) and triethylamine (1.76 ml) in DCM (50 ml) at room temperature, under an atmosphere of nitrogen. The reaction mixture was stirred for 2 hours and then the mixture was washed with saturated aqueous potassium hydrogensulfate, dried ($Na_2SO_4$), and concentrated in vacuo to give a clear oil. Purification by column chromatography, using 0-30% ethyl acetate in hexane as eluent, gave 1-tert-butyl 2-methyl (2R,4S)-4-{[tert-butyl (dimethyl)silyl]oxy}pyrrolidine-1,2-dicarboxylate as a clear oil (891 mg, 59%); NMR spectrum ($CDCl_3$) 4.43-4.32 (m, 2H), 3.75-3.72 (m, 2H), 3.65-3.56 (m, 1H), 3.43-3.31 (m, 1H), 2.21-2.15 (m, 1H), 2.07-1.98 (m, 1H), 1.47 (s, 3H), 1.42 (s, 6H), 0.88 (s, 9H), 0.07 (s, 6H).

Lithium borohydride (2M solution in THF, 6.19 ml) was added dropwise to a stirred solution of 1-tert-butyl 2-methyl (2R,4S)-4-{[tert-butyl(dimethyl)silyl]oxy}pyrrolidine-1,2-dicarboxylate (891 mg) in ether (100 ml) at 0° C. under an atmosphere of nitrogen. The mixture was allowed to warm to room temperature and stirred for 3 hours. A saturated solution of potassium hydrogencarbonate (5 ml) was added slowly, followed by water (20 ml). The ether layer was separated, and the aqueous layer washed with DCM (3x). The combined organic layers were dried ($Na_2SO_4$) and concentrated in vacuo to give tert-butyl (2R,4S)-4-{[tert-butyl(dimethyl)silyl]oxy}-2-(hydroxymethyl)pyrrolidine-1-carboxylate as a clear oil (750 mg, 88%), which was used without further purification; NMR spectrum ($CDCl_3$) 4.82 (d, 1H), 4.26-4.28 (m, 1H), 4.13-4.15 (m, 1H), 3.67-3.73 (m, 1H), 3.55 (ddd, 1H), 3.42-3.46 (m, 1H), 3.35 (dd, 1H), 1.92-2.01 (m, 1H), 1.48 (s, 9H), 0.91-0.97 (m, 1H), 0.88 (s, 9H), 0.07 (s, 6M).

EXAMPLE 21

(3S,5R)-5-[({4-[3-Chloro-4-fluoroanilino]-7-methoxyquinazolin-5-yl}oxy)methyl]-1-(N,N-dimethylglycyl)pyrrolidin-3-ol

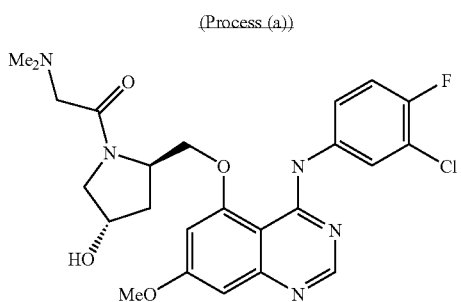

(Process (a))

The procedure described in Example 20 was repeated using (3S,5R)-5-[({4-[3-chloro-4-fluoroanilino]-7-methoxyquinazolin-5-yl}oxy)methyl]pyrrolidin-3-ol (185 mg) with N,N-dimethylglycine (50 mg) to give the title compound as a white solid in 73% yield; NMR spectrum (DMSO-d6) 9.93 (s, 1H), 8.45 (s, 1H), 8.15 (dd, 1H), 7.76-7.70 (m, 1H), 7.45 (t, 1H), 6.83 (s, 2H), 5.09-5.08 (m, 1H), 4.70-4.66 (m, 1H), 4.45-4.40 (m, 2H), 4.28-4.23 (m, 1H), 3.93 (s, 3H), 3.62-3.49 (m, 2H), 3.20 (d, 1H), 3.00 (d, 1H), 2.21 (s, 6H), 2.06-2.02 (m, 2H); Mass spectrum MH+ 504.

EXAMPLE 22

(3S,5R)-1-Acetyl-5-[({4-[3-chloro-4-fluoroanilino]-7-methoxyquinazolin-5-yl}oxy)methyl]pyrrolidin-3-ol

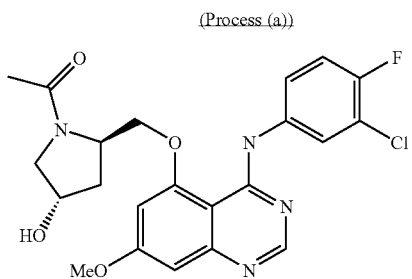

(Process (a))

The procedure described in Example 20 was repeated using (3S,5R)-5-[({4-[3-chloro-4-fluoroanilino]-7-methoxyquinazolin-5-yl}oxy)methyl]pyrrolidin-3-ol (120 mg) with acetic acid (18 µl) to give the title compound as a white solid in 59% yield; NMR spectrum (DMSO-d6) 9.95 (s, 1H), 8.46 (s, 1H), 8.16-8.14 (m, 1H), 7.73-7.70 (m, 1H), 7.46 (t, 1H), 6.85 (s, 1H), 6.84 (s, 1H), 5.10 (m, 1H), 4.67-4.63 (m, 1H), 4.47-4.38 (m, 2H), 4.26-4.21 (m, 1H), 3.94 (s, 3H), 3.59 (dd, 1H), 3.41 (dd, 1H), 2.11-2.05 (m, 2H), 2.00 (s, 3H); Mass spectrum MH+ 461.

EXAMPLE 23

(3S,5R)-5-[({4-[3-Chloro-4-fluoroanilino]-7-methoxyquinazolin-5-yl}oxy)methyl]-1-(methoxyacetyl)pyrrolidin-3-ol

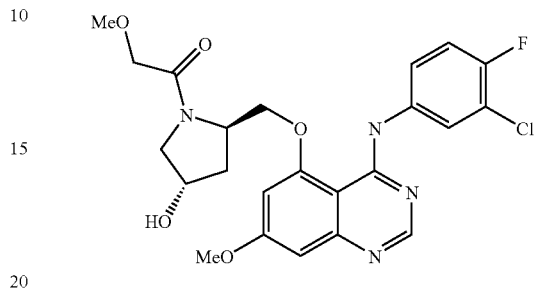

(Process (a))

The procedure described in Example 20 was repeated using (3S,5R)-5-[({4-[3-chloro-4-fluoroanilino]-7-methoxyquinazolin-5-yl}oxy)methyl]pyrrolidin-3-ol (120 mg) with methoxyacetic acid (24 µl) to give the title compound as a white solid in 60% yield; NMR spectrum (DMSO-d6) 9.96 (s, 1H), 8.45 (s, 1H), 8.17-8.14 (m, 1H), 7.76-7.72 (m, 1H), 7.45 (t, 1H), 6.83 (s, 2H), 5.10 (m, 1H), 4.73-4.69 (m, 1H), 4.47-4.38 (m, 2H), 4.25 (dd, 1H), 4.10-3.98 (m, 2H), 3.94 (s, 3H), 3.51 (dd, 1H), 3.40 (s, 1H), 3.29 (s, 3H), 2.05-2.02 (m, 2H); Mass spectrum MH+ 491.

EXAMPLE 24

(3S,5R)-5-[({4-[3-Chloro-4-fluoroanilino]-7-methoxyquinazolin-5-yl}oxy)methyl]-1-[(4-methylpiperazin-1-yl)acetyl]pyrrolidin-3-ol

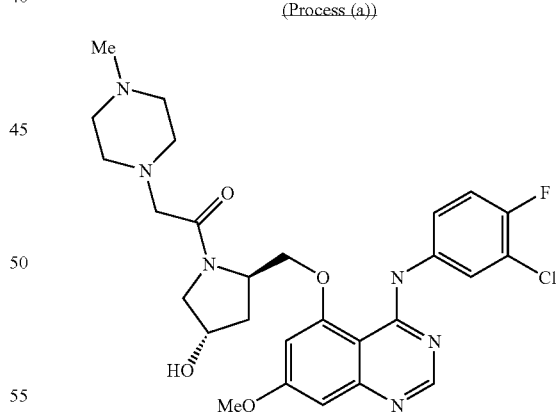

(Process (a))

The procedure described in Example 20 was repeated using (3S,5R)-5-[({4-[3-chloro-4-fluoroanilino]-7-methoxyquinazolin-5-yl}oxy)methyl]pyrrolidin-3-ol (120 mg) with N-methylpiperazin-1-ylacetic acid (50 mg). Purification by column chromatography, using 0 to 10% 7N ammonia in methanol in DCM as eluent, gave the title compound as a white solid (82 mg, 51%); NMR spectrum (CDCl3) 9.62 (s, 1H), 8.51 (s, 1H), 7.86-7.82 (m, 1H), 7.55-7.50 (m, 1H), 7.16-7.10 (m, 1H), 6.84 (br s, 1H), 6.54 (br s, 1H), 4.90-4.80 (m, 1H), 4.51 (m, 1H), 4.37-4.33 (m, 1H), 4.20-4.10 (m, 1H), 3.90 (s, 3H), 3.86-3.80 (m, 1H), 3.54-3.50 (m, 1H), 3.21 (d, 1H), 3.02 (d, 1H), 2.69-2.17 (br m, 13H), 2.05-1.90 (m, 1H); Mass spectrum MH+ 559.

EXAMPLE 25

(3R,5S)-5-[({4-[3-Chloro-4-fluoroanilino]-7-methoxyquinazolin-5-yl}oxy)methyl]1-glycoloylpyrrolidin-3-ol

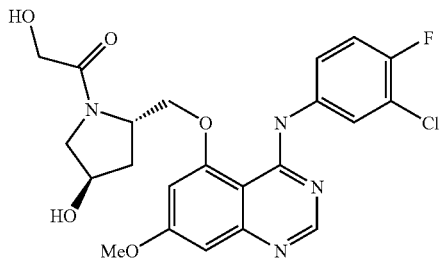

(Process (a))

The procedure described in Example 20 was repeated using (3R,5S)-5-[({4-[3-chloro-4-fluoroanilino]-7-methoxyquinazolin-5-yl}oxy)methyl]pyrrolidin-3-ol (209 mg) with glycolic acid (42 mg) to give the title compound as a white solid in 53% yield; NMR spectrum (DMSO-d6) 10.17 (s, 1H), 8.53 (s, 1H), 8.14 (dd, 1H), 7.74-7.69 (m, 1H), 7.47 (t, 1H), 6.92 (d, 1H), 6.83 (d, 1H), 5.14-5.10 (m, 1H), 4.71-4.67 (m, 1H), 4.50-4.44 (m, 1H), 4.40-4.38 (m, 1H), 4.28-4.23 (m, 1H), 4.06-4.03 (m, 2H), 3.95 (s, 3H), 3.53-3.48 (m, 3H), 2.05-2.02 (m, 2H); Mass spectrum MH+ 477.

The (3R,5S)-5-[({4-[3-chloro-4-fluoroanilino]-7-methoxyquinazolin-5-yl}oxy)methyl]pyrrolidin-3-ol used as starting material was prepared as follows:

Di-tert-butylazodicarboxylate (DTAD, 692 mg) was added in one portion to a mixture of 4-[3-chloro-4-fluoroanilino]-7-methoxyquinazolin-5-ol (640 mg), tert-butyl (2S,4R)-4-{[tert-butyl(dimethyl)silyl]oxy}-2-(hydroxymethyl)-pyrrolidine-1-carboxylate (830 mg), and triphenylphosphine (788 mg) in DCM (50 ml) at room temperature, under an atmosphere of nitrogen. The reaction mixture was stirred at room temperature for 24 hours and then concentrated in vacuo to leave a brown oil. Purification by column chromatography, using 0-50% ethyl acetate in hexane as eluent, gave tert-butyl (2S,4R)-4-{[tert-butyl(dimethyl)silyl]-oxy}-2-[({4-[3-chloro-4-fluoroanilino]-7-methoxyquinazolin-5-yl}oxy)methyl]-pyrrolidine-1-carboxylate as a white solid (884 mg, 70%); Mass spectrum MH+ 633.

tert-Butyl (2S,4R)-4-{[tert-butyl(dimethyl)silyl]oxy}-2-[({4-[3-chloro-4-fluoroanilino]-7-methoxyquinazolin-5-yl}oxy)methyl]pyrrolidine-1-carboxylate (860 mg) was dissolved in trifluoroacetic acid (40 ml) and stirred at room temperature for 24 hours. The reaction mixture was then concentrated in vacuo, and excess water was added, followed by the careful addition of saturated aqueous sodium hydrogen carbonate. The mixture was extracted with 3% methanol in DCM and the organic layer was separated, dried (Na2SO4) and concentrated in vacuo to leave a light brown foam. Trituration with cold acetonitrile gave (3R,5S)-5-[({4-[3-chloro-4-fluoroanilino]-7-methoxy-quinazolin-5-yl}oxy)methyl]-pyrrolidin-3-ol as an off-white solid (394 mg, 69%); NMR spectrum (DMSO-d6) 10.50-10.00 (br, 1H), 8.49 (s, 1H), 8.25 (dd, 1H), 7.90-7.84 (m, 1H), 7.44 (t, 1H), 6.82 (d, 1H), 6.76 (d, 1H), 4.92 (br s, 1H), 4.38 (dd, 1H), 4.32 (br s, 1H), 3.92-3.86 (m, 4H), 3.77-3.23 (br s, 1H), 3.09 (dd, 1H), 2.83 (d, 1H), 1.88 (dd, 1H), 1.74-1.65 (m, 1H); Mass spectrum MH+ 419.

The tert-butyl (2S,4R)-4-{[tert-butyl(dimethyl)silyl]oxy}-2-(hydroxymethyl)-pyrrolidine-1-carboxylate used as a starting material is commercially available or can be prepared using an analogous process to that described in Example 20 for the preparation of tert-butyl (2R,4S)-4-{[tert-butyl(dimethyl)silyl]oxy}-2-(hydroxymethyl)-pyrrolidine-1-carboxylate but using (4R)-1-(tert-butoxycarbonyl)-4-hydroxy-L-proline.

EXAMPLE 26

(3R,5S)-5-[({4-[3-Chloro-4-fluoroanilino]-7-methoxyquinazolin-5-yl}oxy)methyl]-1-dimethylglycyl)pyrrolidin-3-ol

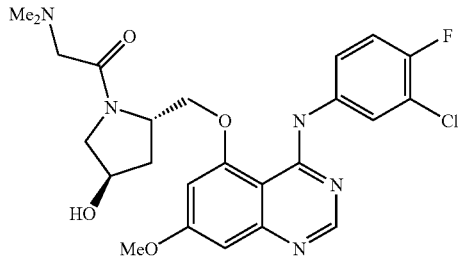

(Process (a))

The procedure described in Example 25 was repeated using (3R,5S)-5-[({4-[3-chloro-4-fluoroanilino]-7-methoxyquinazolin-5-yl}oxy)methyl]pyrrolidin-3-ol (185 mg) with N,N-dimethylglycine (50 mg) to give the title compound as a white solid in 65% yield; NMR spectrum (DMSO-d6) 9.93 (s, 1H), 8.45 (s, 1H), 8.15 (dd, 1H), 7.76-7.70 (m, 1H), 7.45 (t, 1H), 6.83 (s, 2H), 5.09-5.08 (m, 1H), 4.70-4.66 (m, 1H), 4.45-4.40 (m, 2H), 4.28-4.23 (m, 1H), 3.93 (s, 3H), 3.62-3.49 (m, 2H), 3.20 (d, 1H), 3.00 (d, 1H), 2.21 (s, 6H), 2.06-2.02 (m, 2H); Mass spectrum MH+ 504.

EXAMPLE 27

(3R,5S)-1-Acetyl-5-[({4-[3-chloro-4-fluoroanilino]-7-methoxyquinazolin-5-yl}oxy)methyl]pyrrolidin-3-ol

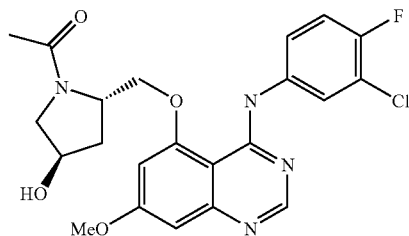

(Process (a))

The procedure described in Example 25 was repeated using (3R,5S)-5-[({4-[3-chloro-4-fluoroanilino]-7-methoxyquinazolin-5-yl}oxy)methyl]pyrrolidin-3-ol (209 mg) with acetic acid (32 µl) to give the title compound as a white solid in 92% yield; NMR spectrum (DMSO-d6) 9.98 (s, 1H), 8.47 (s, 1H), 8.16-8.14 (m, 1H), 7.73-7.70 (m, 1H) 6.84 (s, 1H), 5.10 (m, 1H), 4.67-4.63 (m, 1H), 4.47-4.38 (m, 2H), 4.26-4.21 (m, 1H), 3.94 (s, 3H), 3.59 (dd, 1H), 3.41 (dd, 1H), 2.11-2.05 (m, 2H), 2.00 (s, 3H); Mass spectrum MH+ 461.

EXAMPLE 28

(3R,5S)-5-[({4-[3-Chloro-4-fluoroanilino]-7-methoxyquinazolin-5-yl}oxy)methyl]-1-(methoxyacetyl)pyrrolidin-3-ol

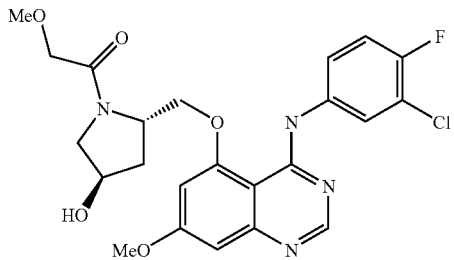

The procedure described in Example 25 was repeated using (3R,5S)-5-[({4-[3-chloro-4-fluoroanilino]-7-methoxyquinazolin-5-yl}oxy)methyl]pyrrolidin-3-ol (209 mg) with methoxyacetic acid (42 µl) to give the title compound as a white solid in 91% yield; NMR spectrum (DMSO-d6) 9.96 (s, 1H), 8.45 (s, 1H), 8.17-8.14 (m, 1H), 7.76-7.72 (m, 1H), 7.45 (t, 1H), 6.83 (s, 2H), 5.10 (m, 1H), 4.73-4.69 (m, 1H), 4.47-4.38 (m, 2H), 4.25 (dd, 1H), 4.10-3.98 (m, 2H), 3.94 (s, 3H), 3.51 (dd, 1H), 3.40 (s, 1H), 3.29 (s, 3H), 2.05-2.02 (m, 2H); Mass spectrum MH+ 491.

EXAMPLE 29

(3R,5S)-5-[({4-[3-Chloro-4-fluoroanilino]-7-methoxyquinazolin-5-yl}oxy)-methyl]-1-[(4-methylpiperazin-1-yl)acetyl]pyrrolidin-3-ol

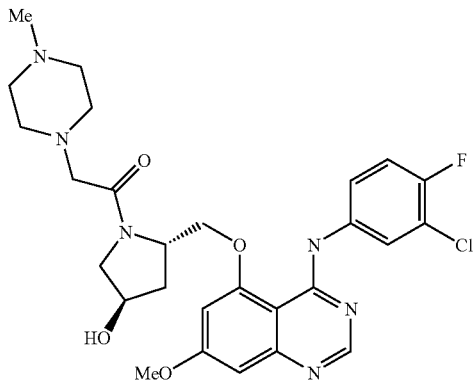

The procedure described in Example 25 was repeated using (3R,5S)-5-[({4-[3-chloro-4-fluoroanilino]-7-methoxyquinazolin-5-yl}oxy)methyl]pyrrolidin-3-ol (210 mg) with N-methylpiperazin-1-ylacetic acid (84 mg). Purification by column chromatography, using 0 to 10% 7N ammonia in methanol in DCM, gave the title compound as a white solid in 72% yield; NMR spectrum (DMSO-d6) 9.91 (s, 1H), 8.45 (s, 1H), 8.14 (dd, 1H), 7.75-7.70 (m, 1H), 7.45 (t, 1H), 6.82 (s, 2H), 5.05 (m, 1H), 4.68-4.64 (m, 1H), 4.43-4.26 (m, 3H), 3.93 (s, 3H), 3.56 (m, 2H), 3.18 (d, 1H), 3.00 (d, 1H), 2.38 (br, 4H), 2.22 (br, 4H), 2.13 (s, 3H), 2.07-2.05 (m, 2H); Mass spectrum MH+ 559.

EXAMPLE 30

(3S,5S)-5-[({4-[3-Chloro-4-fluoroanilino]-7-methoxyquinazolin-5-yl}oxy)methyl]-1-glycoloylpyrrolidin-3-ol

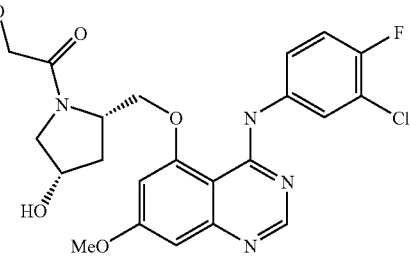

The procedure described in Example 20 was repeated using (3S,5S)-5-[({4-[3-chloro-4-fluoroanilino]-7-methoxyquinazolin-5-yl}oxy)methyl]pyrrolidin-3-ol (157 mg) with glycolic acid (31 mg) to give the title compound as a white solid in 81% yield; NMR spectrum (DMSO-d6) 10.01 (s, 1H), 8.48 (s, 1H), 8.22 (dd, 1H), 7.74-7.69 (m, 1H), 7.43 (t, 1H), 6.84 (d, 1H), 6.78 (d, 1H), 5.29-5.28 (m, 1H), 4.73-4.68 (m, 1H), 4.64-4.59 (m, 2H), 4.44-4.42 (m, 1H), 4.34-4.31 (m, 1H), 4.06-4.05 (m, 2H), 3.93 (s, 3H), 3.64 (dd, 1H), 3.45 (s, 1H), 2.25-2.12 (m, 1H), 1.99-1.95 (m, 1H); Mass spectrum MH+ 477.

The (3S,5S)-5-[({4-[3-chloro-4-fluoroanilino]-7-methoxyquinazolin-5-yl}oxy)methyl]pyrrolidin-3-ol used as starting material was prepared as follows:

Di-tert-butylazodicarboxylate (DTAD, 1.38 g) was added in one portion to a mixture of 4-[3-chloro-4-fluoroanilino]-7-methoxyquinazolin-5-ol (1.28 g), tert-butyl (2S,4S)-4-{[tert-butyl(dimethyl)silyl]oxy}-2-(hydroxymethyl)-pyrrolidine-1-carboxylate (1.66 g), and triphenylphosphine (1.58 g) in DCM (100 ml) at room temperature, under an atmosphere of nitrogen. The reaction mixture was stirred at room temperature for 28 hours and then concentrated in vacuo to leave a brown oil. Purification by column chromatography, using 0-50% ethyl acetate in hexane as eluent, gave tert-butyl (2S,4S)-4-{[tert-butyl(dimethyl)silyl]-oxy}-2-[({4-[3-chloro-4-fluoroanilino]-7-methoxyquinazolin-5-yl}oxy)methyl]-pyrrolidine-1-carboxylate as a white solid (1.13 g, 45%); Mass spectrum MH+ 633.

tert-Butyl (2S,4S)-4-{[tert-butyl(dimethyl)silyl]oxy}-2-[({4-[3-chloro-4-fluoro-anilino]-7-methoxyquinazolin-5-yl}oxy)methyl]pyrrolidine-1-carboxylate (1.13 g) was dissolved in trifluoroacetic acid (50 ml) and stirred at room temperature for 72 hours. The reaction mixture was then concentrated in vacuo, and excess water was added, followed by the careful addition of saturated aqueous sodium hydrogen carbonate. The mixture was extracted with 3% methanol in DCM and the organic layer was separated, dried (Na$_2$SO$_4$) and concentrated in vacuo to leave a pink solid. Trituration with cold acetonitrile gave (3S,5S)-5[({4-[3-chloro-4-fluoroanilino]-7-methoxy-quinazolin-5-yl}oxy)methyl]pyrrolidin-3-ol as a brown solid (380 mg, 51%); NMR spectrum (DMSO-d6) 10.38-10.54 (br s, 1H), 8.52 (s, 1H), 8.36 (dd, 1H), 7.94-7.99 (m, 1H), 7.43 (t, 1H), 6.84 (d, 1H), 6.79 (d, 1H), 4.75 (d, 1H), 4.41 (dd, 1H), 4.26-4.34 (m, 1H), 4.17 (t, 1H), 3.94 (s, 3H), 3.54-3.73 (m, 1H), 2.96 (dd, 1H), 2.79 (dd, 1H), 2.11-2.20 (m, 1H), 1.41-1.49 (m, 1H); Mass spectrum MH$^+$ 419.

The tert-butyl (2S,4S)-4-{[tert-butyl(dimethyl)silyl]oxy}-2-(hydroxymethyl)-pyrrolidine-1-carboxylate used as starting material was prepared in an analogous method to tert-butyl (2R,4S)-4-({[tert-butyl(dimethyl)silyl]oxy}-2-(hydroxymethyl)-pyrrolidine-1-carboxylate described in Example 20, preparation of starting materials, starting from 1-tert-butyl 2-methyl (2S,4S)-4-hydroxypyrrolidine-1,2-dicarboxylate (commercially available or can be prepared using an analogous process to that described in Example 20 for the preparation of 1-tert-butyl 2-methyl (2R,4S)-4-hydroxypyrrolidine-1,2-dicarboxylate but using (4S)-1-(tert-butoxycarbonyl)-4-hydroxy-L-proline.

EXAMPLE 31

(3S,5S)-5-[({4-[3-Chloro-4-fluoroanilino]-7-methoxyquinazolin-5-yl}oxy)methyl]-1-(N,N-dimethylglycyl)pyrrolidin-3-ol (Process (a))

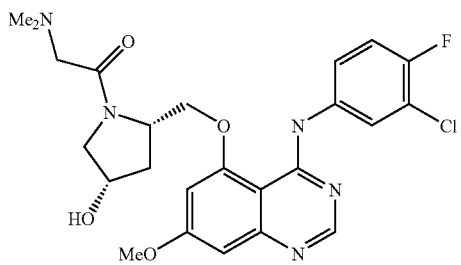

The procedure described in Example 30 was repeated using (3S,5S)-5-[({4-[3-chloro-4-fluoroanilino]-7-methoxyquinazolin-5-yl}oxy)methyl]pyrrolidin-3-ol (157 mg) with N,N-dimethylglycine (43 mg) to give the title compound as a white solid in 83% yield; NMR spectrum (DMSO-d6) 10.03 (s, 1H), 8.46 (s, 1H), 8.19 (dd, 1H), 7.76-7.71 (m, 1H), 7.43 (t, 1H), 6.83 (d, 1H), 6.75 (d, 1H), 5.27-5.26 (m, 1H), 4.72-4.67 (m, 1H), 4.61-4.56 (m, 1H), 4.41-4.40 (m, 1H), 4.34-4.29 (m, 1H), 3.93 (s, 3H), 3.78 (dd, 1H), 3.52 (br d, 1H), 3.14 (d, 1H), 2.99 (d, 1H), 2.26-2.17 (m, 7H), 1.95-1.90 (m, 1H); Mass spectrum MH$^+$ 50

EXAMPLE 32

(3R,5R)-5-[({4-[3-Chloro-4-fluoroanilino]-7-methoxyquinazolin-5-yl]oxy)methyl]-1-glycoloylpyrrolidin-3-ol (Process (a))

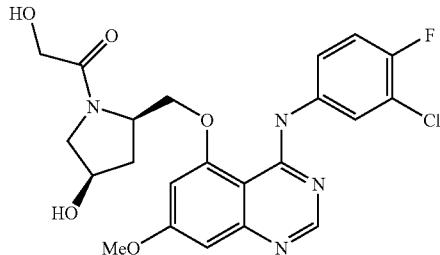

The procedure described in Example 20 was repeated using (3R,5R)-5-[({4-[3-chloro-4-fluoroanilino]-7-methoxyquinazolin-5-yl}oxy)methyl]pyrrolidin-3-ol (209 mg) with glycolic acid (42 mg) to give the title compound as a white solid in 46% yield; NMR spectrum (DMSO-d6) 10.01 (s, 1H), 8.48 (s, 1H), 8.22 (dd, 1H), 7.74-7.69 (m, 1H), 7.43 (t, 1H), 6.84 (d, 1H), 6.78 (d, 1H), 5.29-5.28 (m, 1H), 4.73-4.68 (m, 1H), 4.64-4.59 (m, 2H), 4.44-4.42 (m, 1H), 4.34-4.31 (m, 1H), 4.06-4.05 (m, 2H), 3.93 (s, 3H), 3.64 (dd, 1H), 3.45 (s, 1H), 2.25-2.12 (m, 1H), 1.99-1.95 (m, 1M); Mass spectrum MH$^+$ 477.

The (3R,5R)-5-[({4-[3-chloro-4-fluoroanilino]-7-methoxyquinazolin-5-yl}-oxy)methyl]pyrrolidin-3-ol used as starting material was prepared as follows:

Di-tert-butylazodicarboxylate (DTAD, 914 mg) was added in one portion to a mixture of 4-[3-chloro-4-fluoroanilino]-7-methoxyquinazolin-5-ol (848 mg), tert-butyl (2R,4R)-4-{[tert-butyl(dimethyl)silyl]oxy}-2-(hydroxymethyl)-pyrrolidine-1-carboxylate (1.10 g), and triphenylphosphine (1.04 g) in DCM (100 ml) at room temperature, under an atmosphere of nitrogen. The reaction mixture was stirred at room temperature for 24 hours and then concentrated in vacuo to leave a brown oil. Purification by column chromatography, using 0-50% ethyl acetate in hexane as eluent, gave tert-butyl (2R,4R)-4-{[tert-butyl(dimethyl)silyl]-oxy}-2-[({4-[3-chloro-4-fluoroanilino]-7-methoxy-quinazolin-5-yl}oxy)methyl]-pyrrolidine-1-carboxylate as a white solid (839 mg, 50%); Mass spectrum MH$^+$ 633.

tert-Butyl (2R,4R)-4-{[tert-butyl(dimethyl)silyl]oxy}-2-[({4-[3-chloro-4-fluoro-anilino]-7-methoxyquinazolin-5-yl}oxy)methyl]pyrrolidine-1-carboxylate (839 mg) was dissolved in trifluoroacetic acid (50 ml) and stirred at room temperature for 72 hours. The reaction mixture was then concentrated in vacuo, and excess water was added, followed by the careful addition of saturated aqueous sodium hydrogen carbonate. The mixture was extracted with 3% methanol in DCM and the organic layer was separated, dried (Na$_2$SO$_4$) and concentrated in vacuo to leave a green solid. Trituration with cold acetonitrile gave (3R,5R)-5-[({4-[3-chloro-4-fluoroanilino]-7-methoxy-quinazolin-5-yl}oxy)methyl]pyrrolidin-3-ol as grey solid (540 mg, 98%); NMR spectrum (DMSO-d6) 10.54-10.02 (br s, 1H), 8.48 (s, 1H), 8.32 (dd, 1H), 7.93-7.88 (m, 1H), 7.38 (t, 1H), 6.79 (d, 1H), 6.69 (d, 1H), 5.05-4.74 (br s, 1H), 4.40-4.32 (m, 2H), 4.16 (t, 1H), 3.91 (s, 3H), 3.80-3.40 (br m, 21), 2.98 (dd, 1H), 2.86 (dd, 1H), 2.22-2.14 (m, 1H), 1.52-1.44 (m, 1H); Mass spectrum MH+ 419.

The tert-butyl (2R,4R)-4-{[tert-butyl(dimethyl)silyl]oxy}-2-(hydroxymethyl)-pyrrolidine-1-carboxylate used as starting material was prepared in an analogous method to tert-butyl (2R,4S)-4-{[tert-butyl(dimethyl)silyl]oxy}-2-(hydroxymethyl)-pyrrolidine-1-carboxylate described in Example 20, preparation of starting materials, starting from (4R)-1-(tert-butoxycarbonyl)-4-hydroxy-D-proline). This gave tert-butyl (2R,4R)-4-{[tert-butyl(dimethyl)silyl]oxy}-2-(hydroxy-methyl)-pyrrolidine-1-carboxylate as a clear oil in 39% over three steps; NMR spectrum (CDCl$_3$) 4.57 (d, 1H), 4.32-4.25 (m, 1H), 4.10-4.00 (m, 1H), 3.83-3.51 (m, 3H), 3.39-3.23 (m, 1H), 2.26-2.18 (m, 1H), 1.48 (s, 9H), 0.97-0.90 (m, 10H), 0.09 (s, 6H).

EXAMPLE 33

(3R,5R)-5-[({4-[3-Chloro-4-fluoroanilino]-7-methoxyquinazolin-5-yl}oxy)-methyl]-1-(N,N-dimethylglycyl)pyrrolidin-3-ol

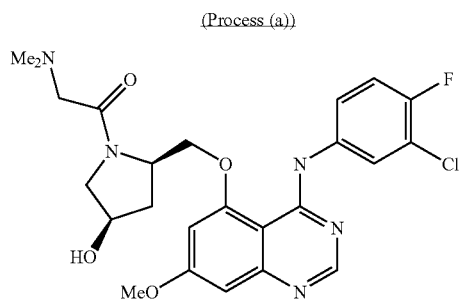

(Process (a))

The procedure described in Example 32 was repeated using (3R,5R)-5-[({4-[3-chloro-4-fluoroanilino]-7-methoxyquinazolin-5-yl}oxy)methyl]pyrrolidin-3-ol (209 mg) with N,N-dimethylglycine (57 mg) to give the title compound as a white solid in 72% yield; NMR spectrum (DMSO-d6) 10.03 (s, 1H), 8.46 (s, 1H), 8.19 (dd, 1H), 7.76-7.71 (m, 1H), 7.43 (t, 1H), 6.83 (d, 1H), 6.75 (d, 1H), 5.27-5.26 (m, 1H), 4.72-4.67 (m, 1H), 4.61-4.56 (m, 1H), 4.41-4.40 (m, 1H), 4.34-4.29 (m, 1H), 3.93 (s, 3H), 3.78 (dd, 1H), 3.52 (br d, 1H), 3.14 (d, 1H), 2.99 (d, 1H), 2.26-2.17 (m, 7H), 1.95-1.90 (m, 1H); Mass spectrum MH+ 504.

The invention claimed is:

1. A quinazoline derivative of the formula I:

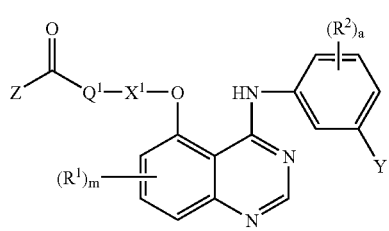

I wherein:
X$^1$ is C(R$^3$)$_2$, wherein each R$^3$, which may be the same or different, is selected from hydrogen and (1-4C)alkyl;

Q$^1$ is pyrrolidinyl;
and wherein Q$^1$ is linked to the group X$^1$—O by a ring carbon atom,
and wherein the group of the formula ZC(O) is at the 1-position of Q$^1$;

Z is selected from (1-4C)alkyl, halogeno-(1-4C)alkyl, hydroxy-(1-4C)alkyl, (1-4C)alkoxy-(1-4C)alkyl, amino-(1-4C)alkyl, (1-4C)alkylamino-(1-4C)alkyl and di-[(1-4C)alkyl]amino-(1-4C)alkyl, or Z is Q$^2$, wherein Q$^2$ is heterocyclyl or heterocyclyl-(1-4C)alkyl, and wherein any CH$_2$ or CH$_3$ group within a Z group, other than a CH$_2$ group within a heterocyclyl ring, optionally bears on each said CH$_2$ or CH$_3$ group one or more halogeno or (1-6C)alkyl substituents or a substituent selected from hydroxy, cyano, amino, carboxy, carbamoyl, formyl, mercapto, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within Q$^1$ or Z optionally bears one or more substituents, which may be the same or different selected from halogeno, trifluoromethyl, cyano, nitro, hydroxy, amino, carboxy, carbamoyl, sulfamoyl, formyl, mercapto, (1-6C)alkyl, (2-6C)alkenyl, (2-6C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, and N-(1-6C)alkyl-(1-6C)alkanesulfonylamino, or from a group of the formula:

—X$^2$—R$^4$ wherein X$^2$ is a direct bond or is selected from O, CO and N(R$^5$), wherein R$^5$ is hydrogen or (1-6C)alkyl, and R$^4$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl, (2-6C)alkanoyloxy-(1-6C)alkyl and (1-6C)alkoxycarbonyl-(1-6C)alkyl, and wherein any heterocyclyl group within $Q^1$ or Z optionally bears 1 or 2 oxo or thioxo substituents;

m is 0, 1 or 2 and $R^1$ when present is located at the 6- and/or 7-position;

each $R^1$ group, which may be the same or different, is selected from hydroxy, (1-6C)alkoxy, (2-6C)alkenyloxy, (2-6C)alkynyloxy, or from a group of the formula:

—$Q^3$—$X^3$— wherein $X^3$ is a direct bond or is O, and $Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, or $(R^1)_m$ is (1-3C)alkylenedioxy, and wherein adjacent carbon atoms in any (2-6C)alkylene chain within a $R^1$ substituent are optionally separated by the insertion into the chain of a group selected from O, S, SO, $SO_2$, $N(R^6)$, CO, $CH(OR^6)$, $CON(R^6)$, $N(R^6)CO$, $SO_2N(R^6)$, $N(R^6)SO_2$, $CH=CH$ and $C\equiv C$ wherein $R^6$ is hydrogen or (1-6C)alkyl, and wherein any $CH_2=CH-$ or $HC\equiv C-$ group within a $R^1$ substituent optionally bears at the terminal $CH_2=$ or $HC\equiv$ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

—$Q^4$—$X^4$— wherein $X^4$ is a direct bond or is selected from CO and $N(R^7)CO$, wherein $R^7$ is hydrogen or (1-6C)alkyl, and $Q^4$ is heterocyclyl or heterocyclyl-(1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—$X^5$—$Q^5$ wherein $X^5$ is a direct bond or is selected from O, S, SO, $SO_2$, $N(R^8)$, CO, $CH(OR^8)$, $CON(R^8)$, $N(R^8)CO$, $SO_2N(R^8)$, $N(R^8)SO_2$, $C(R^8)_2O$, $C(R^8)_2S$ and $C(R^8)_2N(R^8)$, wherein $R^8$ is hydrogen or (1-6C)alkyl, and $Q^5$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein any heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, formyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, and N-(1-6C)alkyl-(1-6C)alkanesulfonylamino, or from a group of the formula:

—$X^6$—$R^9$ wherein $X^6$ is a direct bond or is selected from O, $N(R^{10})$ and C(O), wherein $R^{10}$ is hydrogen or (1-6C)alkyl, and $R^9$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl N,N-di-[(1-6C)alkyl]carbamoyl-(1-6C)alkyl, (2-6C)alkanoyl-(1-6C)alkyl or (1-6C)alkoxycarbonyl-(1-6C)alkyl, and wherein any heterocyclyl group within a substituent on $R^1$ optionally bears 1 or 2 oxo or thioxo substituents;

Y is selected from halogeno, cyano, trifluoromethyl, (1-6C)alkyl, (2-6C)alkenyl, (2-6C)alkynyl and (1-6C)alkoxy;

each $R^2$, which may be the same or different, is selected from halogeno, cyano, nitro, hydroxy, amino, carboxy, carbamoyl, sulfamoyl, trifluoromethyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, N-(1-6C)alkylsulfamoyl, N,N-di-[(1-6C)alkyl]sulfamoyl; and a is 0, 1, 2, 3 or 4;

or a pharmaceutically acceptable salt thereof.

2. The quinazoline derivative of the formula I according to claim 1, or a pharmaceutically acceptable salt thereof, wherein each of $X^1$, $Q^1$, $R^1$, $R^2$, a, m and Y are as defined in claim 1; and Z is selected from halogeno-(1-4C)alkyl, hydroxy-(1-4C)alkyl, (1-4C)alkoxy-(1-4C)alkyl, amino-(1-4C)alkyl, (1-4C)alkylamino-(1-4C)alkyl and di-[(1-4C)alkyl]amino-(1-4C)alkyl, or Z is $Q^2$, wherein $Q^2$ is heterocyclyl or heterocyclyl-(1-4C)alkyl, and wherein the heterocyclyl in $Q^2$ contains at least 1 nitrogen heteroatom, and optionally 1 or 2 further heteroatoms selected from oxygen, nitrogen and sulfur, and wherein any $CH_2$ or $CH_3$ group within a Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, formyl, mercapto, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within $Q^1$ or Z optionally bears one or more substituents, which may be the same or different selected from halogeno, trifluoromethyl, cyano, nitro, hydroxy, amino, carboxy, carbamoyl, sulfamoyl, formyl, mercapto, (1-6C)alkyl, (2-6C)alkenyl, (2-6C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, and N-(1-6C)alkyl-(1-6C)alkanesulfonylamino, or from a group of the formula:

—$X^2$—$R^4$ wherein $X^2$ is a direct bond or is selected from O, CO and N($R^5$), wherein $R^5$ is hydrogen or (1-6C)alkyl, and $R^4$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl, (2-6C)alkanoyloxy-(1-6C)alkyl and (1-6C)alkoxycarbonyl-(1-6C)alkyl, and wherein any heterocyclyl group within $Q^1$ or Z optionally bears 1 or 2 oxo or thioxo substituents.

3. The quinazoline derivative of the formula I according to claim 1, or a pharmaceutically acceptable salt thereof, wherein $Q^1$ is pyrrolidin-2-yl substituted at the 1-position by the group of the formula ZC(O).

4. The quinazoline derivative of the formula I according to claim 1, or a pharmaceutically acceptable salt thereof, wherein Z is selected from hydroxy-(1-2C)alkyl, (1-4C)alkoxy-(1-2C)alkyl, amino-(1-2C)alkyl, (1-4C)alkylamino-(1-2C)alkyl and di-[(1-4C)alkyl]amino-(1-2C)alkyl, or Z is $Q^2$, wherein $Q^2$ is heterocyclyl or heterocyclyl-(1-2C)alkyl, and wherein the heterocyclyl in $Q^2$ is a fully saturated 4, 5, 6 or 7 membered monocyclic heterocyclyl group which contains at least 1 nitrogen heteroatom, and optionally 1 or 2 further heteroatoms selected from oxygen, nitrogen and sulfur, and wherein $Q^2$ is linked to the (1-2C)alkyl or C(O) group by a ring nitrogen, and wherein any $CH_2$ or $CH_3$ group within a Z group, other than a $CH_2$ group within a heterocyclyl ring, optionally bears on each said $CH_2$ or $CH_3$ group one or more (1-4C)alkyl substituents or a substituent selected from cyano, carbamoyl, formyl, (2-6C)alkenyl, (2-6C)alkynyl, N-(1-6C)alkylcarbamoyl, N,N-di-[(1-6C)alkyl]carbamoyl and (2-6C)alkanoyl, and wherein any $CH_2$ which is attached to 2 carbon atoms or a $CH_3$ group which is attached to a carbon atom within a Z group, other than a $CH_2$ group within a heterocyclyl ring, optionally bears on each said $CH_2$ or $CH_3$ group one or more halogeno substituents or a substituent selected from hydroxy, amino, mercapto, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyloxy, (2-6C)alkanoylamino and N-(1-6C)alkyl-(2-6C)alkanoylamino, and wherein any heterocyclyl group within Z optionally bears one or more substituents, which may be the same or different selected from halogeno, trifluoromethyl, cyano, nitro, hydroxy, amino, carbamoyl, formyl, (1-6C)alkyl, (2-6C)alkenyl, (2-6C)alkynyl, (1-6C)alkoxy, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, N-(1-6C)alkylsulfamoyl and N,N-di-[(1-6C)alkyl]sulfamoyl, or from a group of the formula:

—$X^2$—$R^4$ wherein $X^2$ is a direct bond or is selected from O, CO and N($R^5$), wherein $R^5$ is hydrogen or (1-4C)alkyl, and $R^4$ is halogeno-(1-6C)alkyl, hydroxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl and N,N-di-[(1-6C)alkyl]carbamoyl-(1-6C)alkyl, and wherein any heterocyclyl group within Z optionally bears 1 or 2 oxo substituents.

5. The quinazoline derivative of the formula I according to claim 1, or a pharmaceutically acceptable salt thereof, wherein Z is selected from (1-2C)alkyl, hydroxy-(1-2C)alkyl, amino-(1-2C)alkyl, (1-4C)alkylamino-(1-2C)alkyl and di-[(1-4C)alkyl]amino-(1-2C)alkyl, or Z is $Q^2$ wherein $Q^2$ is heterocyclyl-(1-2C)alkyl, and wherein the heterocyclyl in $Q^2$ is selected from pyrrolidin-1-yl, piperidino and piperazin-1-yl, and wherein $Q^2$ is linked to the (1-2C)alkyl group by a ring nitrogen, and wherein any heterocyclyl group within Z optionally bears one or more substituents, which may be the same or different selected from fluoro, chloro, hydroxy, (1-3C)alkyl, (1-3C)alkoxy, or from a group of the formula:

—$X^2$—$R^4$ wherein $X^2$ is a direct bond or is O, and $R^4$ is halogeno-(1-3C)alkyl, hydroxy-(1-3C)alkyl or (1-3C)alkoxy-(1-3C)alkyl, and wherein any heterocyclyl group within Z optionally bears an oxo substituent.

6. The quinazoline derivative of the formula I according to claim 1, or a pharmaceutically acceptable salt thereof, wherein $Q^1$—$X^1$ is selected from (2R)-pyrrolidin-2-ylmethyl and (2S)-pyrrolidin-2-ylmethyl, and wherein the group of the formula ZC(O) is attached at the 1-position of the pyrrolidin-2-yl group, Z is selected from methyl, hydroxymethyl, aminomethyl, (1-2C)alkylaminomethyl, di-[(1-2C)alkyl]aminomethyl and pyrrolidin-1-ylmethyl, and wherein any heterocyclyl group within Z or $Q^1$ optionally bears one or more substituents, which may be the same or different selected from hydroxy, (1-3C)alkyl and (1-3C)alkoxy, and wherein any heterocyclyl group within Z optionally bears an oxo substituent.

7. The quinazoline derivative of the formula I according to claim 1, or a pharmaceutically acceptable salt thereof, wherein m is 1 and $R^1$ is located at the 7-position.

8. The quinazoline derivative of the formula I according to claim 7, or a pharmaceutically acceptable salt thereof, wherein $R^1$ is selected from (1-4C)alkoxy, hydroxy-(1-4C)alkoxy and (1-4C)alkoxy(1-4C)alkoxy.

9. The quinazoline derivative of the formula I according to claim 1, or a pharmaceutically acceptable salt thereof, wherein the aniline at the 4-position in the quinazoline ring in formula I is selected from 3-chloro-4-fluoroanilino, 3-chloro-2-fluoroanilino, 2-fluoro-5-chloroanilino, 3-bromoanilino, 3-methylanilino and 3-ethynylanilino.

10. The quinazoline derivative of the formula I according to claim 1, or a pharmaceutically acceptable salt thereof, wherein:

m is 1 and $R^1$ is located at the 7-position and is selected from (1-4C)alkoxy, hydroxy-(1-4C)alkoxy, methoxy-(1-4C)alkoxy and ethoxy-(1-4C)alkoxy;

$Q^1-X^1$ is pyrrolidin-2-ylmethyl, and wherein $Q^1$ optionally bears one or more substituents, which may be the same or different selected from hydroxy and (1-3C)alkyl, and wherein $Q^1$ optionally bears an oxo substituent, and wherein the group of the formula ZC(O) is attached at the 1-position in $Q^1$;

Z is selected from hydroxymethyl, aminomethyl, methylaminomethyl, di-methylaminomethyl and pyrrolidin-1-ylmethyl, and wherein any heterocyclyl group within Z optionally bears 1 or 2 substituents, which may be the same or different selected from hydroxy, amino, methyl, ethyl, methoxy, methylamino and di-methylamino;

Y is halogeno;

each $R^2$, which may be the same or different, is selected from halogeno; and a is 0, 1 or 2;

or a pharmaceutically acceptable salt thereof.

11. The quinazoline derivative of the formula I according to claim 1 of the formula Ia:

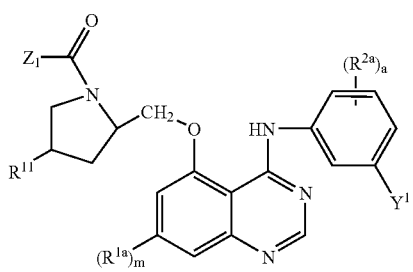

wherein:

m is 0 or m is 1 and $R^{1a}$ is selected from (1-4C)alkoxy, hydroxy-(1-4C)alkoxy and (1-4C)alkoxy(1-4C)alkoxy;

$R^{11}$ is selected from hydrogen, hydroxy, (1-4C)alkyl, (1-4C)alkoxy, hydroxy-(1-4C)alkyl, (1-4C)alkoxy-(1-4C)alkyl, hydroxy-(1-4C)alkoxy and (1-4C)alkoxy-(1-4C)alkoxy;

$Z^1$ is selected from (1-2C)alkyl, hydroxy-(1-2C)alkyl, (1-2C)alkoxy-(1-2C)alkyl, amino-(1-2C)alkyl, (1-4C)alkylamino-(1-2C)alkyl and di-[(1-4C)alkyl]amino-(1-2C)alkyl, or $Z^1$ is $Q^2$, wherein $Q^2$ is pyrrolidinyl-(1-2C)alkyl, and wherein any pyrrolidinyl group within $Z^1$ optionally bears one or more substituents, which may be the same or different selected from fluoro, chloro, hydroxy, (1-3C)alkyl, (1-3C)alkoxy, or from a group of the formula:

—$X^2$—$R^4$ wherein $X^2$ is a direct bond or is O, and $R^4$ is halogeno-(1-3C)alkyl, hydroxy-(1-3C)alkyl or (1-3C)alkoxy-(1-3C)alkyl, and wherein any pyrrolidinyl group within $Z^1$ optionally bears an oxo substituent;

$Y^1$ is selected from fluoro, chloro, bromo, cyano, methyl, ethyl, isopropyl, methoxy, ethoxy, vinyl, allyl, ethynyl, 1-propynyl and 2-propynyl;

each $R^{2a}$, which may be the same or different, is selected from fluoro, chloro, bromo, cyano, hydroxy, trifluoromethyl, (1-4C)alkyl, (2-4C)alkynyl and (1-4C)alkoxy; and a is 0, 1 or 2;

or a pharmaceutically acceptable salt thereof.

12. The quinazoline derivative of the formula Ia according to claim 11, or a pharmaceutically acceptable salt thereof wherein:

m is 1 and $R^{1a}$ is selected from methoxy, ethoxy, 2-hydroxyethoxy, 2-methoxyethoxy and 2-ethoxyethoxy;

$R^{11}$ is selected from hydrogen, hydroxy or methoxy;

$Z^1$ is selected from methyl, hydroxymethyl, aminomethyl, methylaminomethyl, dimethylaminomethyl and pyrrolidin-1-ylmethyl;

$Y^1$ is selected from fluoro, chloro, bromo and ethynyl;

$R^{2a}$ is selected from fluoro, chloro and bromo; and a is 0 or 1.

13. The quinazoline derivative of the formula Ia according to claim 1 selected from:

2-{(2R)-2-[({4-[3-Chloro-4-fluoroanilino]-7-methoxyquinazolin-5-yl}oxy)methyl]pyrrolidin-1-yl}-2-oxoethanol;

N-(3-chloro-4-fluorophenyl)-5-({(2R)-1-[(dimethylamino)acetyl]pyrrolidin-2-yl}methoxy)-7-methoxyquinazolin-4-amine;

N-(3-chloro-4-fluorophenyl)-7-methoxy-5-{[(2S)-1-(pyrrolidin-1-ylacetyl)pyrrolidin-2-yl]methoxy}quinazolin-4-amine;

(3S,5S)-5-[({4-[3-chloro-4-fluoroanilino]-7-methoxyquinazolin-5-yl}oxy)methyl]-1-(N,N-dimethylglycyl)pyrrolidin-3-ol;

(3S,5R)-5-[({4-[3-chloro-4-fluoroanilino]-7-methoxyquinazolin-5-yl}oxy)methyl]-1-glycoloylpyrrolidin-3-ol;

(3R,5R)-5-[({4-[3-chloro-4-fluoroanilino]-7-methoxyquinazolin-5-yl}oxy)methyl]-1-glycoloylpyrrolidin-3-ol;

(3R,5R)-5-[({4-[3-chloro-4-fluoroanilino]-7-methoxyquinazolin-5-yl}oxy)-methyl]-1-(N,N-dimethylglycyl)pyrrolidin-3-ol;

(3S,5R)-1-acetyl-5-[({4-[3-chloro-4-fluoroanilino]-7-methoxyquinazolin-5-yl}oxy)methyl]pyrrolidin-3-ol;

2-[(2R)-2-({[4-[3-chloro-4-fluoroanilino]-7-(2-hydroxyethoxy)quinazolin-5-yl]oxy}methyl)pyrrolidin-1-yl]-2-oxoethanol;

2-[(2R)-2-({[4-[3-chloro-4-fluoroanilino]-7-(2-ethoxyethoxy)quinazolin-5-yl]oxy}methyl)pyrrolidin-1-yl]-2-oxoethanol;

2-{(2R)-2-[({4-[3-chloro-4-fluoroanilino]-7-ethoxyquinazolin-5-yl}oxy)methyl]-pyrrolidin-1-yl}-2-oxoethanol; and N-(3-chloro-4-fluorophenyl)-7-methoxy-5-{[(2R)-1-(methoxyacetyl)pyrrolidin-2-yl]methoxy}quinazolin-4-amine;

and pharmaceutically acceptable salts thereof.

14. A process for the preparation of a quinazoline derivative of the formula I, or a pharmaceutically acceptable salt thereof, according to claim 1 which comprises:

Process (a) the coupling, conveniently in the presence of a suitable base, of a quinazoline of the formula II:

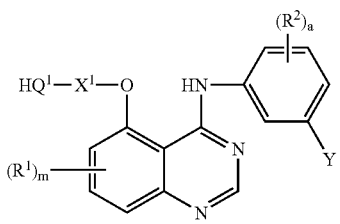

wherein $R^1$, $R^2$, $X^1$, Y, $Q^1$, a and m have any of the meanings defined in claim 1 except that any functional group is optionally protected, with a carboxylic acid of the formula Z—COOH, or a reactive derivative thereof, wherein Z has any of the meanings defined in claim 1 except that any functional group is optionally protected;

or

Process (b): for the preparation of those compounds of the formula I wherein Z is selected from amino-(1-4C)alkyl, (1-4C)alkylamino-(1-4C)alkyl, di-[(1-4C)alkyl]amino-(1-4C)alkyl, or Z is $Q^2$, wherein $Q^2$ is heterocyclyl-(1-4C)alkyl, and wherein the heterocyclyl in $Q^2$ contains at least 1 nitrogen heteroatom, and optionally 1 or 2 further heteroatoms selected from oxygen, nitrogen and sulfur, and wherein $Q^2$ is attached by a ring nitrogen atom, the reaction of a quinazoline of the formula III:

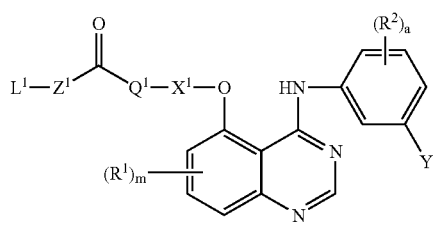

wherein $R^1$, $R^2$, $X^1$, Y, $Q^1$, a and m have any of the meanings defined in claim 1 except that any functional group is optionally protected, $Z^1$ is a direct bond or (1-4C)alkyl and $L^1$ is a displaceable group, with an amine or a compound of the formula $Q^2H$;

or

Process (c): for the preparation of those compounds of the formula I wherein $R^1$ is a hydroxy group, the cleavage of a quinazoline derivative of the formula I wherein $R^1$ is a or Process (d): for the preparation of those compounds of the formula I wherein m is 1 and $R^1$ is optionally substituted (1-6C)alkoxy, optionally substituted (2-6C)alkenyloxy, optionally substituted (2-6C)alkynyloxy or a group of the formula:

$Q^3—X^3—$ wherein $X^3$ is O, and $Q^3$ is as defined in claim 1 except that any functional group is optionally protected, the reaction, conveniently in the presence of a suitable base, of a quinazoline of the formula IV:

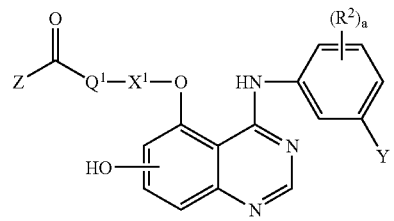

wherein $R^2$, $X^1$, Y, $Q^1$, Z and a have any of the meanings defined in claim 1 except that any functional group is optionally protected with a compound of the formula $R^{1a}—L^1$ or $Q^3—L^1$ wherein $Q^3$ is as defined in claim 1 except any functional group is optionally protected, $R^{1a}$ is selected from optionally substituted (1-6C)alkyl, optionally substituted (2-6C)alkenyl and optionally substituted (2-6C)alkynyl and L is a displaceable group;

or

Process (e): for the preparation of those compounds of the formula I wherein m is 1 and $R^1$ is optionally substituted (1-6C)alkoxy, optionally substituted (2-6C)alkenyloxy, optionally substituted (2-6C)alkynyloxy or a group of the formula:

$Q^3—X^3—$ wherein $X^3$ is O, and $Q^3$ is as defined in claim 1, the coupling of the a quinazoline of the formula IV as hereinbefore defined with an alcohol of the formula $R^{1a}OH$ or $Q^3OH$ wherein $Q^3$ is as defined in claim 1 except any functional group is optionally protected and $R^{1a}$ is as defined in process (d);

and thereafter, optionally:

(i) removing any protecting group that is present;

(ii) forming a pharmaceutically acceptable salt.

15. A pharmaceutical composition which comprises a quinazoline derivative of the formula I, or a pharmaceutically-acceptable salt thereof, as defined in claim 1 or claim 2 in association with a pharmaceutically-acceptable diluent or carrier.

16. A method for the treatment a cancer selected from breast, colorectal and head and neck cancer in a warm-blooded animal in need of such treatment, which comprises administering to said animal an effective amount of a quinazoline derivative of the formula I, or a pharmaceutically-acceptable salt thereof, as defined in claim 1 or claim 2.

* * * * *

UNITED STATES PATENT AND TRADEMARK OFFICE
CERTIFICATE OF CORRECTION

PATENT NO. : 7,659,279 B2  Page 1 of 1
APPLICATION NO. : 10/555085
DATED : February 9, 2010
INVENTOR(S) : Hennequin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1069 days.

Signed and Sealed this

Twenty-eighth Day of December, 2010

David J. Kappos
*Director of the United States Patent and Trademark Office*